United States Patent
King et al.

(10) Patent No.: US 11,986,999 B2
(45) Date of Patent: May 21, 2024

(54) MODIFIED 3D-PRINTED OBJECTS AND THEIR USES

(71) Applicant: Lung Biotechnology PBC, Silver Spring, MD (US)

(72) Inventors: Jamie King, Bedford, NH (US); Barbara Nsiah, Manchester, NH (US); Rebecca Duffy, Silver Spring, MD (US); Aman Kaur, Manchester, NH (US); Luis Alvarez, Lexington, MA (US)

(73) Assignee: Lung Biotechnology PBC, Silver Spring, MD (US)

( * ) Notice: Subject to any disclaimer, the term of this patent is extended or adjusted under 35 U.S.C. 154(b) by 0 days.

(21) Appl. No.: 17/738,698

(22) Filed: May 6, 2022

(65) Prior Publication Data

US 2022/0371268 A1    Nov. 24, 2022

Related U.S. Application Data

(60) Provisional application No. 63/185,302, filed on May 6, 2021.

(51) Int. Cl.
| | |
|---|---|
| *B29C 64/188* | (2017.01) |
| *B29L 31/00* | (2006.01) |
| *B33Y 10/00* | (2015.01) |
| *B33Y 40/20* | (2020.01) |
| *B33Y 70/00* | (2020.01) |
| *B33Y 80/00* | (2015.01) |

(52) U.S. Cl.
CPC ....... *B29C 64/188* (2017.08); *B29L 2031/753* (2013.01); *B33Y 10/00* (2014.12); *B33Y 40/20* (2020.01); *B33Y 70/00* (2014.12); *B33Y 80/00* (2014.12)

(58) Field of Classification Search
CPC .... B29C 64/188; B33Y 40/20; A61L 2430/06
See application file for complete search history.

(56) References Cited

U.S. PATENT DOCUMENTS

| | | | |
|---|---|---|---|
| 2009/0011486 A1* | 1/2009 | Bettinger | ............... C08J 9/0023 435/180 |
| 2013/0029030 A1* | 1/2013 | Larsen | ............... A61L 24/0036 427/2.31 |
| 2017/0307598 A1 | 10/2017 | Skardal et al. | |
| 2017/0354758 A1* | 12/2017 | Deng | ........................ A61K 9/06 |
| 2020/0040306 A1 | 2/2020 | Xu et al. | |
| 2020/0179563 A1 | 6/2020 | Bagley et al. | |

(Continued)

FOREIGN PATENT DOCUMENTS

| | | |
|---|---|---|
| CN | 105688279 A | 6/2016 |
| DE | 10 2019 132 211 B3 | 4/2021 |

(Continued)

OTHER PUBLICATIONS

U.S. Appl. No. 17/738,686, filed May 6, 2022, Melican et al.
(Continued)

*Primary Examiner* — Michael M. Robinson
(74) *Attorney, Agent, or Firm* — Foley & Lardner LLP

(57) ABSTRACT

Provided herein are methods which alter the mechanical and biological properties of polymeric materials. Also provided are compositions comprising the polymeric materials having said properties.

16 Claims, 53 Drawing Sheets

(56) References Cited

U.S. PATENT DOCUMENTS

2020/0324021 A1* 10/2020 Van Belleghem .. A61L 27/3641
2020/0339925 A1   10/2020 Miller et al.
2020/0347167 A1   11/2020 Alli et al.

FOREIGN PATENT DOCUMENTS

| WO | WO-2016/154070 A1 | 9/2016  |
|----|-------------------|---------|
| WO | WO-2017/031167 A1 | 2/2017  |
| WO | WO-2017/040156 A1 | 3/2017  |
| WO | WO-2017/066507 A1 | 4/2017  |
| WO | WO-2019/195256 A1 | 10/2019 |
| WO | WO-2019/226710 A8 | 11/2019 |
| WO | WO-2020/028720 A1 | 2/2020  |
| WO | WO-2020/182987 A1 | 9/2020  |

OTHER PUBLICATIONS

U.S. Appl. No. 17/738,694, filed May 6, 2022, Kaur et al.
U.S. Appl. No. 17/738,736, filed May 6, 2022, Melican et al.
U.S. Appl. No. 17/738,764, filed May 6, 2022, Kaur et al.
U.S. Appl. No. 17/738,833, filed May 6, 2022, Modaresifar et al.
Akentjew et al., "Rapid fabrication of reinforced and cell-laden vascular grafts structurally inspired by human coronary arteries," Nature Communications, Dec. 1, 2019, 10(1):1-15.
Ali et al., "A Photo-Crosslinkable Kidney ECM-Derived Bioink Accelerates Renal Tissue Formation," Advanced Healthcare Materials, Apr. 1, 2019, 8(7):e1800992, 10 pages.
Baek et al., "In situ assembly of the collagen-polyacrylamide interpenetrating network hydrogel: Enabling decoupled control of stiffness and degree of swelling," European Polymer Journal, Nov. 1, 2015, 72:413-422.
Bilisik et al., "3D fabrics for technical textile applications," in Non-woven Fabrics, Chapter 4, Intech, 2016, 81-141.
Calo et al., "Biomedical applications of hydrogels: A review of patents and commercial products," European Polymer Journal, Apr. 2015, 65:252-267.
Fukao et al., "Hydrogels toughened by biominerals providing energy-dissipative sacrificial bonds," J. Mater. Chem. B, 2020, 8:5184-5188.
Galliger et al., "3D bioprinting for lungs and hollow organs," Translational Research, May 14, 2019, 211:19-34.
Han, Hai-Chao, "Twisted Blood Vessels: Symptoms, Etiology and Biomechanical Mechanisms," J. Vasc. Res., May 2012 (online Mar. 14, 2012), 49(3):185-197.
Koobatian et al., "Surgical Technique for the Implantation of Tissue Engineered Vascular Grafts and Subsequent In Vivo Monitoring," J. Vis. Exp., Apr. 3, 2015, (98):52354, 1-11.
Marga et al., "Toward engineering functional organ modules by additive manufacturing," Biofabrication, Jun. 1, 2012, 4(2):022001, 13 pages.
Pashneh-Tala et al., "The Tissue-Engineered Vascular Graft-Past, Present and Future," Tissue Engineering: Part B, 2016 (online Oct. 7, 2015), 22(1):68-100.
Weigel et al., "Photopolymer formulations for uSL printing of hydrogel microstructures as swellable functional elements," Progress in Biomedical Optics and Imaging, SPIR—International Society for Optical Engineering, Mar. 5, 2021, 11637:116370A-1-116370A13.
Zhu et al., "Bioactive modification of poly(ethylene glycol) hydrogels for tissue engineering," Biomaterials, Jun. 1, 2010, 31(17):4639-4656.

* cited by examiner

300 μm channels, 200 μm walls oriented to have vertical pillars

FIG. 24
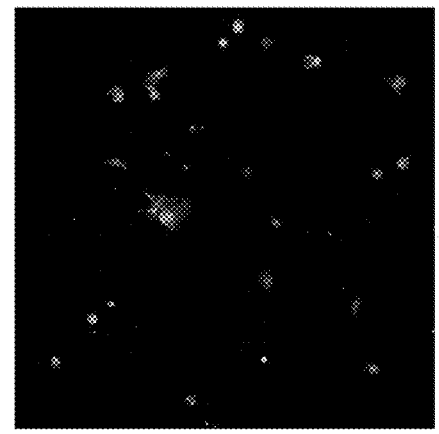
PBS
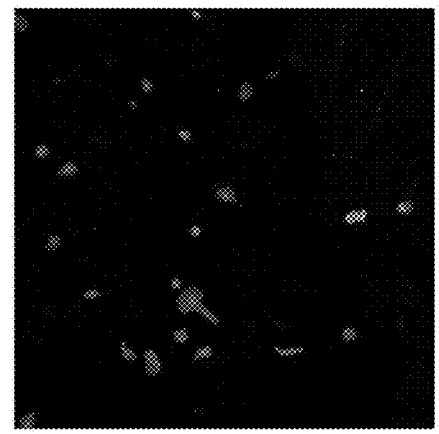
5U/mL Esterase
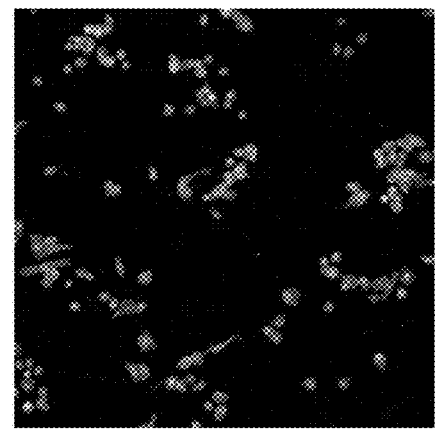
0.1M NaOH
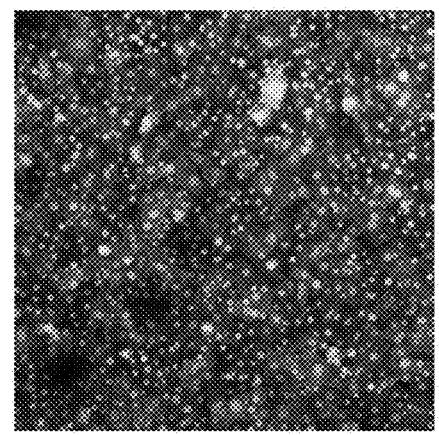
Glass Control
Day 7 SAEC

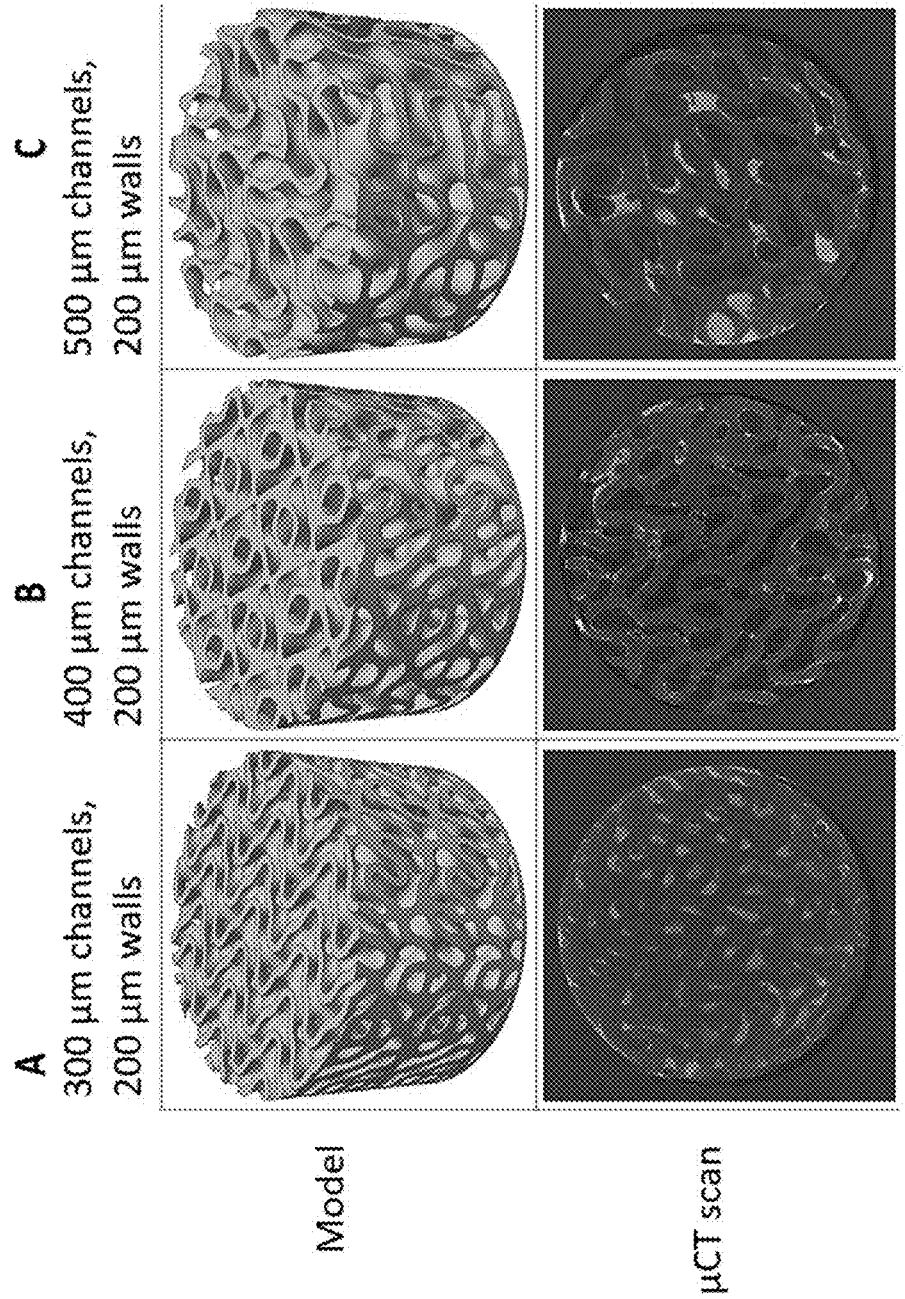

FIG. 44

| | | Compressive Mechanical Properties | | Tensile Mechanical Properties | | | Cell Attachment | | | Swelling | Migration |
|---|---|---|---|---|---|---|---|---|---|---|---|
| | | Ultimate Strain | Ultimate Stress | Ultimate Tensile Strain | Ultimate Tensile Strength | | LFN | PAEC | SAEC | | |
| Bioinks | Ink A | | | | | | | | | | TBD |
| | Ink B | | | | | | | | | | |
| | Ink C | | | | | | | | | | |
| | Ink D | | | | | | | TBD | | | |
| Treatment | NaOH | | | | | | | | | | |
| | Esterase | | | | | | | | | | |
| Structure | Fischer | | | | | | | | | | |
| | Solid | | | | | | | | | | |

Legend: Above / Meets

Ultimate Stress = 200 kPa  
Ultimate Strain = 40%  
Ultimate Tensile Stress = 100 kPa  
Ultimate Tensile Strain = 20%  
Cell Attachment = 40%  
Swelling = 20%

MODIFIED 3D-PRINTED OBJECTS AND THEIR USES

CROSS-REFERENCE TO RELATED APPLICATIONS

This application claims priority to U.S. Provisional Application No. 63/185,302, filed May 6, 2021, the entire contents of which are incorporated herein by reference.

BACKGROUND

The present disclosure involves using both chemical means and hydrolytic enzymes as a post processing treatment of 3D printed objects to tune their biocompatibility and mechanical properties. The premise of these treatments is that accelerated hydrolysis (via a base such as a hydroxide salt (NaOH or KOH), via an esterase enzyme, or proteolytic degradation via a protease) will result in creation of chemical moieties that are favorable to cell attachment. The effect of these treatments also results in a change in the crosslinking density of the material. The ability to conduct post processing of a 3D printed object and alter its properties provides an alternative to 3D printing a material with a starting material that has the already-desired properties or modifying the printing method itself to change the properties of a material.

The material may be used to provide polymeric scaffolds, which when activated by treatment as disclosed herein, attract cells into the scaffold which may then be used to grow tissues from congregated cells around the scaffolds.

SUMMARY

In one aspect, a method of modifying a polymeric scaffold comprising polymerized poly(ethyelene glycol) di(meth)acrylate moieties, polymerized poly(ethyelene glycol) di(meth)acrylamide moieties, polymerized poly(ethyelene glycol) (meth)acrylate/(methacrylamide) moieties, and mixtures thereof, the method comprising: providing the polymeric scaffold; contacting the scaffold with a hydrolysis agent or a proteolysis agent.

In one aspect, a method of increasing the affinity of a polymeric scaffold for cells, the polymeric scaffold comprising polymerized poly(ethyelene glycol) di(meth)acrylate moieties, polymerized poly(ethyelene glycol) di(meth)acrylamide moieties, polymerized poly(ethyelene glycol) (meth)acrylate/(methacrylamide) moieties, and mixtures thereof, wherein the method comprises providing the polymeric scaffold and contacting the polymeric scaffold with a hydrolysis agent or a proteolysis agent.

In some embodiments, the polymeric scaffold comprises polymerized poly(ethylene glycol) diacrylate moieties. In some embodiments, the polymerized poly(ethylene glycol) diacrylate moieties comprise PEGDA3400, PEGDA575, or a mixture thereof.

In some embodiments, the polymeric scaffold further comprises polymerized collagen. In some embodiments, the polymerized collagen comprises collagen-methacrylamide (colMA) moieties. In some embodiments, the polymeric scaffold further comprises polymerized hydroxypropyl acrylate (HPA). In some embodiments, the polymeric scaffold further comprises a polymerized UV initiator.

In some embodiments, the contacting step, the scaffold is contacted with a hydrolysis agent. In some embodiments, the hydrolysis agent comprises a hydroxide ion. In some embodiments, the concentration of the hydrolysis agent is about 1 mM to about 25 mM, about 25 mM to about 50 mM, about 50 mM to about 100 mM, about 100 mM to about 150 mM, about 150 mM to about 300 mM, about 300 mM to about 500 mM, about 500 mM to about 1 M, about 1 M to about 5 M, or about greater than 5 M.

In some embodiments, the scaffold is contacted with the hydrolysis agent for about 1 min to about 30 min, about 30 min to about 1 hr, about 1 hr to about 2.5 hr, about 2.5 hr to about 5 hr, about 5 hr to about 7.5 hr, about 7.5 hr to about 10 hr, about 10 hr to about 24 hr, about 24 hr to about 2 days, about 2 days to about 4 days, about 4 days to about 8 days, about 8 days to about 12 days, about 12 days to about 30 days, or greater than about 30 days.

In some embodiments, the contacting step, the scaffold is contacted with a proteolysis agent. In some embodiments, the proteolysis agent is selected from an esterase, collagenase, stromelysins, gelatinases, or a hydrolase. In some embodiments, the concentration of the proteolysis agent is about 0.1 U to about 1 U, about 1 U to about 2.5 U, about 2.5 U to about 5 U, about 5 U to about 7.5 U, about 7.5 U to about 10 U, about 10 U to about 15 U, or about greater than 15 U.

In some embodiments, the scaffold is contacted with the proteolysis agent for about 1 hr, about 1 hr to about 2.5 hr, about 2.5 hr to about 5 hr, about 5 hr to about 7.5 hr, about 7.5 hr to about 10 hr, about 10 hr to about 24 hr, about 24 hr to about 2 days, about 2 days to about 4 days, about 4 days to about 8 days, about 8 days to about 12 days, about 12 days to about 30 days, or greater than about 30 days.

In some embodiments, the scaffold is a 3D-printed scaffold. In some embodiments, the scaffold is solid. In some embodiments, the scaffold comprises channels and walls. In some embodiments, the channels have a width of about 200 μm to about 500 μm. In some embodiments, the walls have a width of about 150 μm to about 400 μm.

In some embodiments, the contacting the scaffold with a hydrolysis agent or a proteolysis agent increases affinity of the scaffold for cells. In some embodiments, the cells are selected from fibroblasts, endothelial cells, epithelial cells, and mixtures thereof.

In one aspect, a polymeric scaffold produced by the method of any embodiments herein is provided.

In one aspect, a composition is provided comprising a hydrolysis or proteolysis agent; and a polymeric scaffold comprising polymerized poly(ethyelene glycol) di(meth)acrylate moieties, polymerized poly(ethyelene glycol) di(meth)acrylamide moieties, polymerized poly(ethyelene glycol) (meth)acrylate/(methacrylamide) moieties, and mixtures thereof.

In some embodiments, the polymeric scaffold or the composition further comprises cells. In some embodiments, of the polymeric scaffold or the composition, the cells comprise Lung Fibroblast (LFN), Porcine Aorta Endothelial Cells (PAEC), Small Airway Epithelial Cells (SAEC), or mixtures thereof.

In one aspect, a method of increasing actin coverage of cells is provided, the method comprising contacting the cells with the polymeric scaffold or the composition of any embodiment herein. In some embodiments, the polymeric scaffold or the composition the cells are selected from fibroblasts, endothelial cells, epithelial cells, and mixtures thereof.

BRIEF DESCRIPTION OF THE DRAWINGS

FIG. 2A is a computer generated model, FIG. 2B is a brightfield image, and FIG. 2C is microCT scan of the disc.

FIG. 3A is quantification percent cell coverage, FIG. 3B is quantification cell spread and FIG. 3C is quantification cell density.

FIG. 5A is quantification percent cell coverage, FIG. 5B is quantification cell spread and FIG. 5C is quantification cell density.

FIG. 7A shows young's modulus, FIG. 7B shows ultimate strain, and FIG. 7C shows ultimate stress.

FIG. 8A shows young's modulus, FIG. 8B shows ultimate tensile strain, and FIG. 8C shows ultimate tensile stress.

FIG. 12A is quantification of percent cell coverage, FIG. 12B is quantification of cell spreading and FIG. 12C is quantification of cell density.

FIG. 14A is quantification of percent cell coverage, FIG. 14B is quantification of cell spreading and FIG. 14C is quantification of cell density.

FIG. 17A shows Ultimate tensile strain, FIG. 17B shows ultimate tensile stress. The tensile mechanical properties were obtained using the tensile strains displacement vs tensile stress plots obtained in FIGS. 15A, 15B, 15C, and 15D.

FIG. 19A is quantification of cell spreading, FIG. 19B is quantification of cell spreading and FIG. 19C is quantification of percent cell coverage.

FIG. 21A is quantification of cell spreading, FIG. 21B is quantification of cell density and FIG. 21C is quantification of percent cell coverage.

FIG. 23A is quantification of cell spreading, FIG. 23B is quantification of cell density and FIG. 23C is quantification of percent cell coverage.

FIG. 24 shows attachment of human of small airway epithelial cells to printed Fischer disc made of Ink A, treated with NaOH, esterase, and PBS, and on glass control slides, after day 7.

FIG. 25A is quantification of cell spreading, FIG. 25B is quantification of cell density and FIG. 25C is quantification of percent cell coverage.

FIG. 26A shows Young's modulus, FIG. 26B shows ultimate strain, FIG. 26C shows ultimate stress.

FIG. 30A shows Young's modulus, FIG. 30B shows ultimate strain, FIG. 30C shows ultimate stress.

FIGS. 36A-36C show models (top row) and microCT scan images (bottom row) of discs made of Ink A having 300 µm channels and 200 µm walls (FIG. 36A), 400 µm channels and 200 µm walls (FIG. 36B), 500 µm channels and 200 µm walls (FIG. 36C).

FIG. 37A shows Young's modulus, FIG. 37B shows ultimate strain, FIG. 37C shows ultimate stress.

FIG. 38A shows Young's modulus, FIG. 38B shows ultimate strain, FIG. 38C shows ultimate stress.

FIG. 40A shows Young's modulus, FIG. 40B shows ultimate strain, FIG. 40C shows ultimate stress.

FIG. 41A shows Young's modulus, FIG. 41B shows ultimate strain, FIG. 41C shows ultimate stress.

FIG. 42A shows Young's modulus, FIG. 42B shows ultimate strain, FIG. 42C shows ultimate stress.

FIG. 43A shows percent actin area, FIG. 43B shows actin area, and FIG. 43C shows cell density.

FIG. 44 shows a table showing whether inks, treatments, and structures that are above, meet, or below the threshold for compressive mechanical properties (ultimate strain and ultimate stress), tensile mechanical properties (ultimate tensile strain and ultimate tensile stress), cell attachment (LFN, PAEC, and SAEC), and swelling. The threshold for each tested parameter is outlined at the bottom.

FIG. 49A shows the sample clamped into the device and FIG. 49B shows the sample broken by application of force by the device.

DETAILED DESCRIPTION

Figure 1:
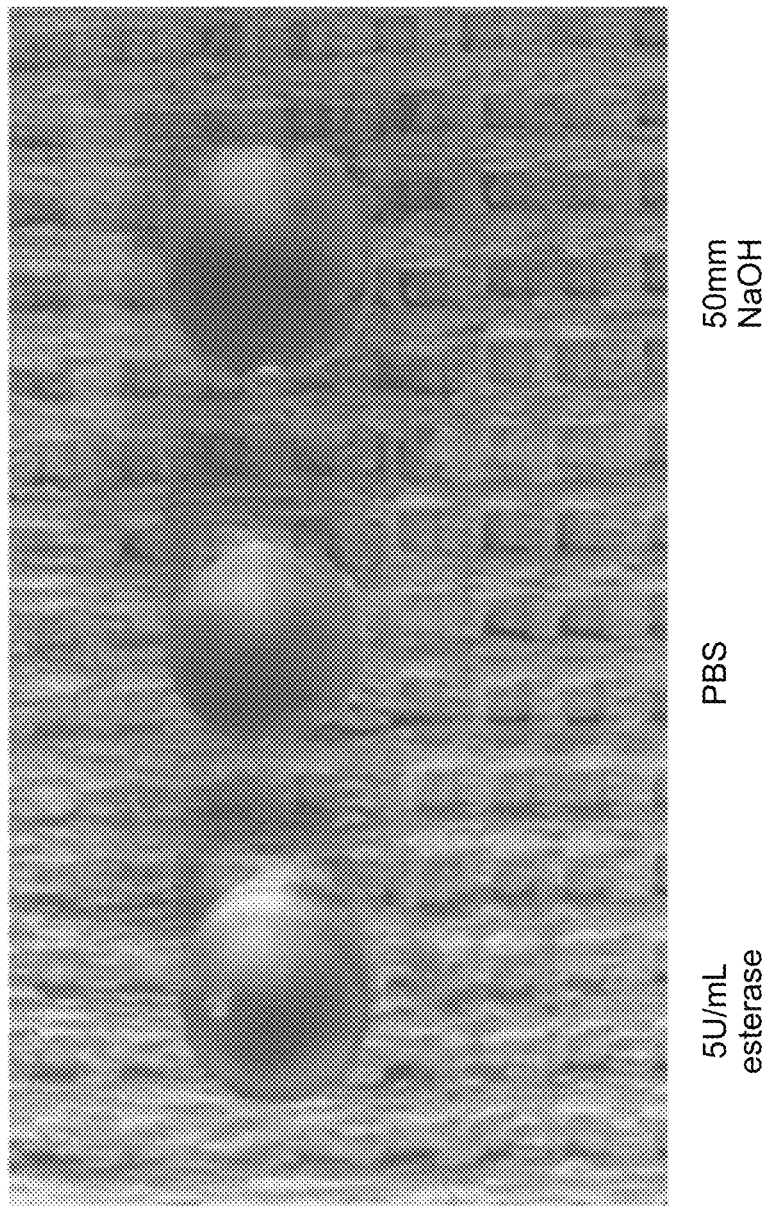
FIG. 1 shows printed discs of Ink A treated with, from left to right, 5 U/mL cholesterol esterase, PBS, or 50 mM NaOH.
Figure 2A:
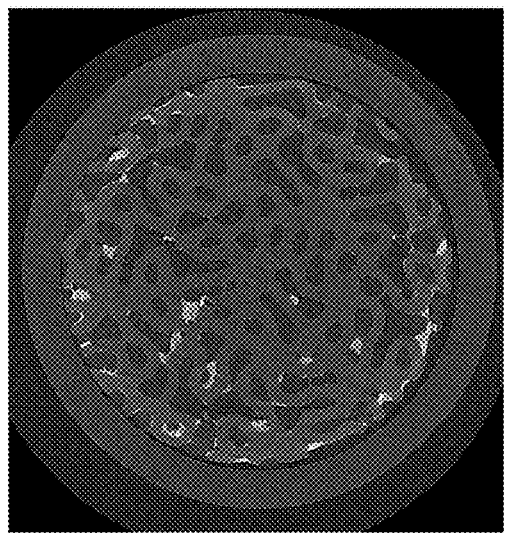
FIGS. 2A-2C are printed fischer discs containing vertical pillars within the disc.
Figure 2B:
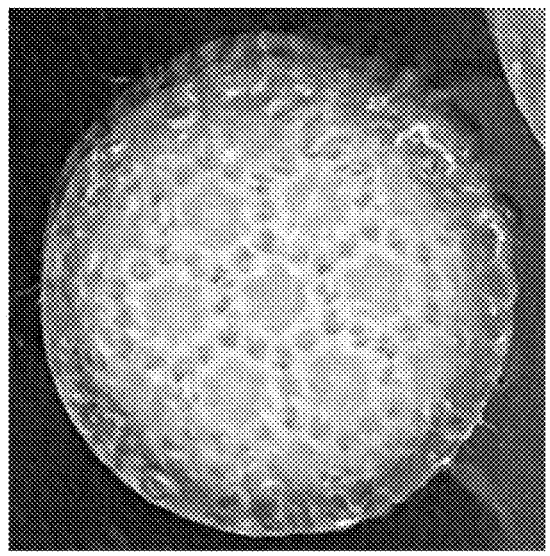
Figure 2C:
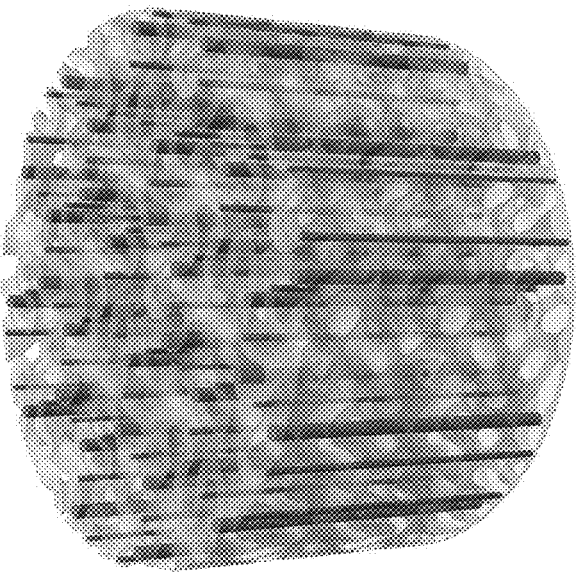
Figures 3A, 3B, 3C:
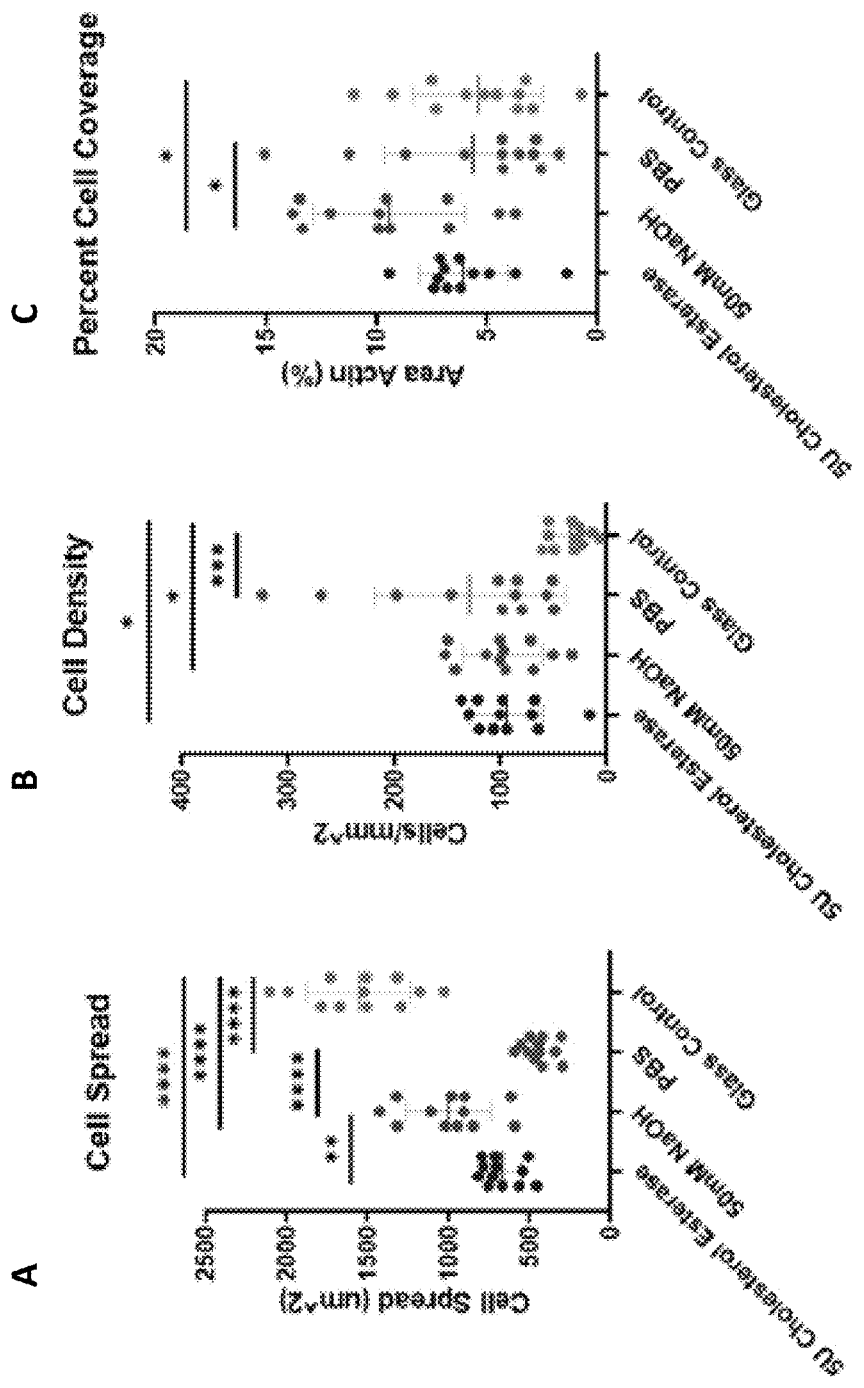
FIGS. 3A-3C are human lung fibroblast cells attached to printed discs made of Ink A following treatment with esterase, NaOH, PBS, and to glass control, after 1 day of culture.
Figure 4A:
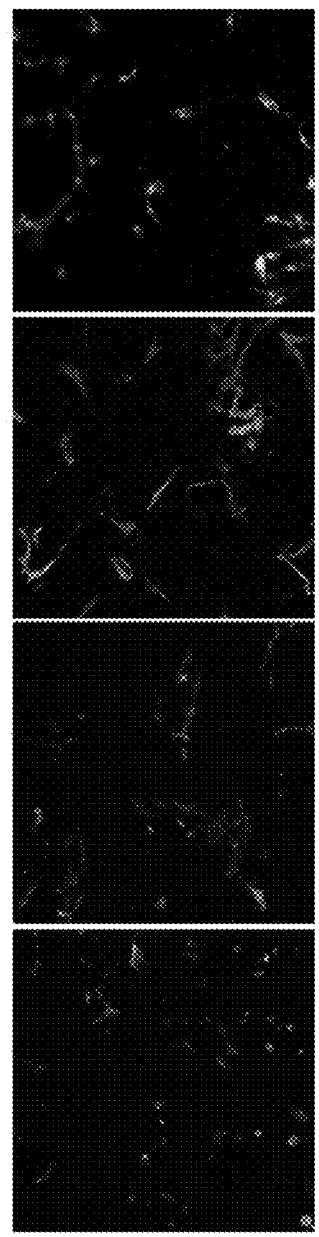
FIGS. 4A-4B are human lung fibroblast cells attached to printed discs made of Ink A following treatment with esterase, NaOH, and PBS, and to glass control after day 1 (FIG. 4A) and day 4 of culture (FIG. 4B).
Figure 4B:
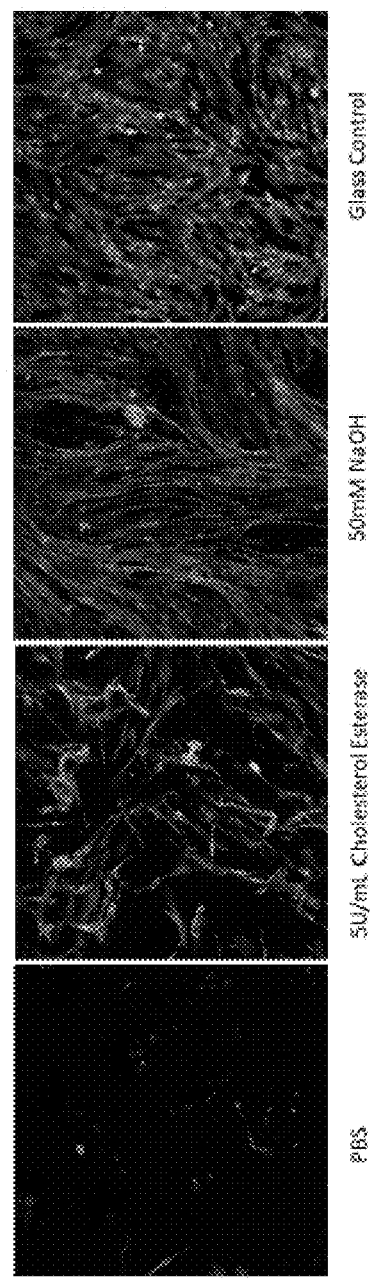
Figures 5A, 5B, 5C:
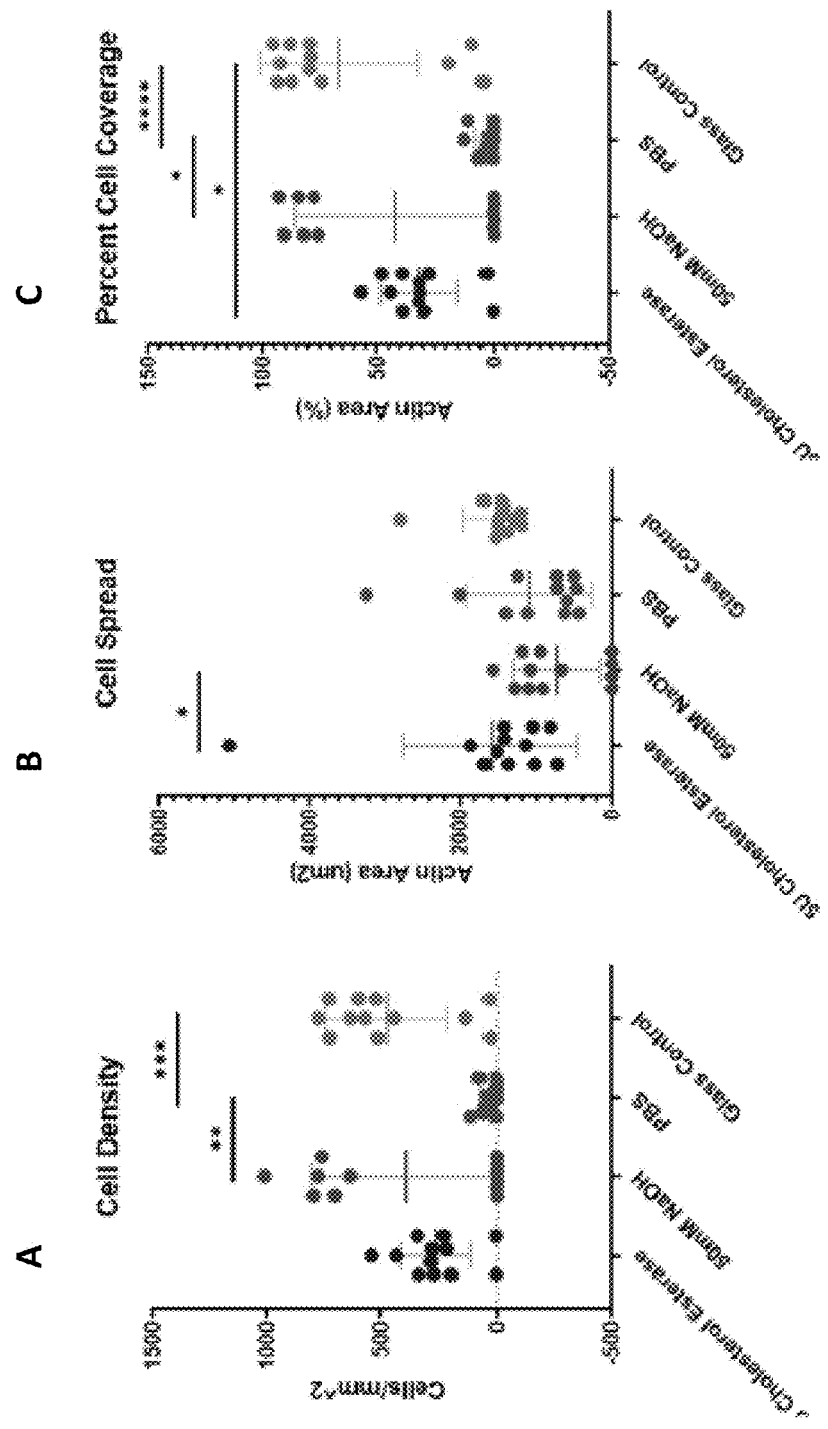
FIGS. 5A-5C are human lung fibroblast cells attached to printed object made of Ink A following treatment with esterase, NaOH, PBS and to glass control, after 4 days of culture.
Figure 6:
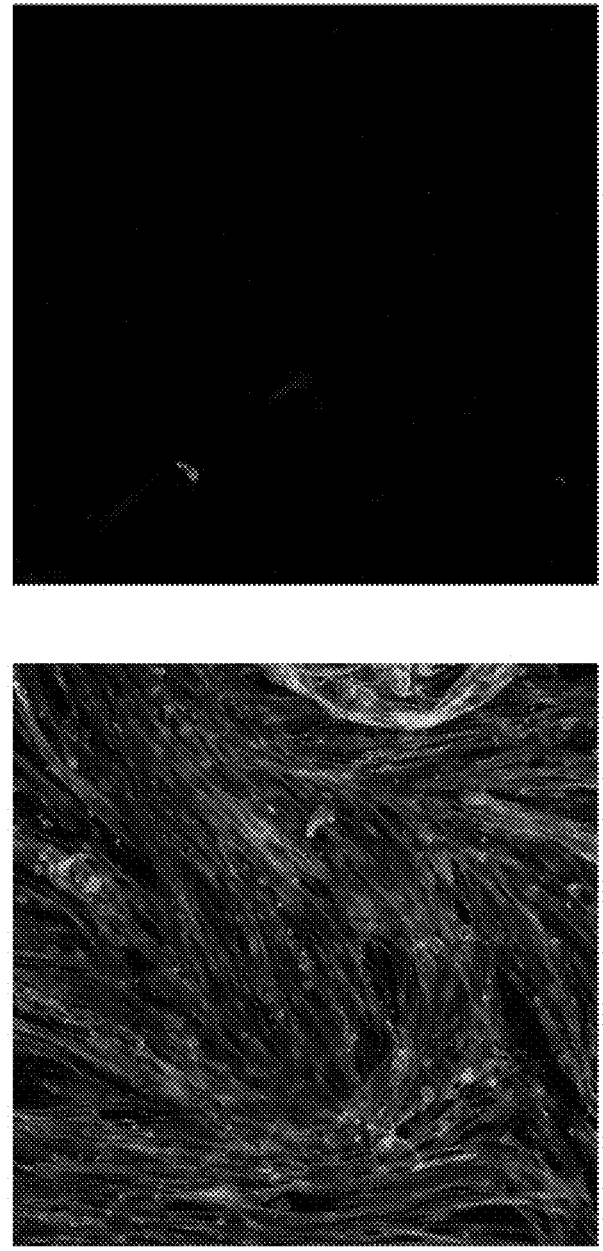
FIG. 6 is human lung fibroblast cells attached to printed object made of Ink A following treatment with NaOH (left) and PBS (right) after 4 days of culture.
Figures 7A, 7B, 7C:
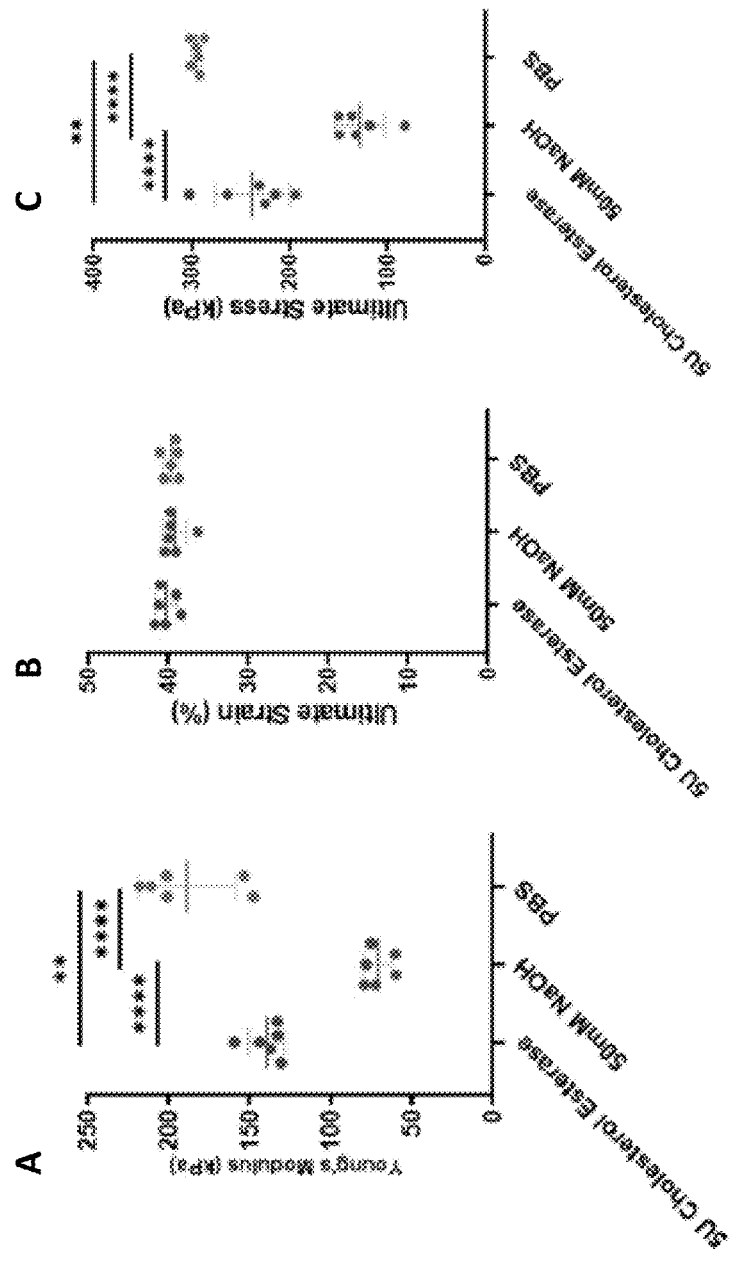
FIGS. 7A-7C is compression test results of printed discs made of Ink A treated with esterase, NaOH, or PBS.
Figures 8A, 8B, 8C:
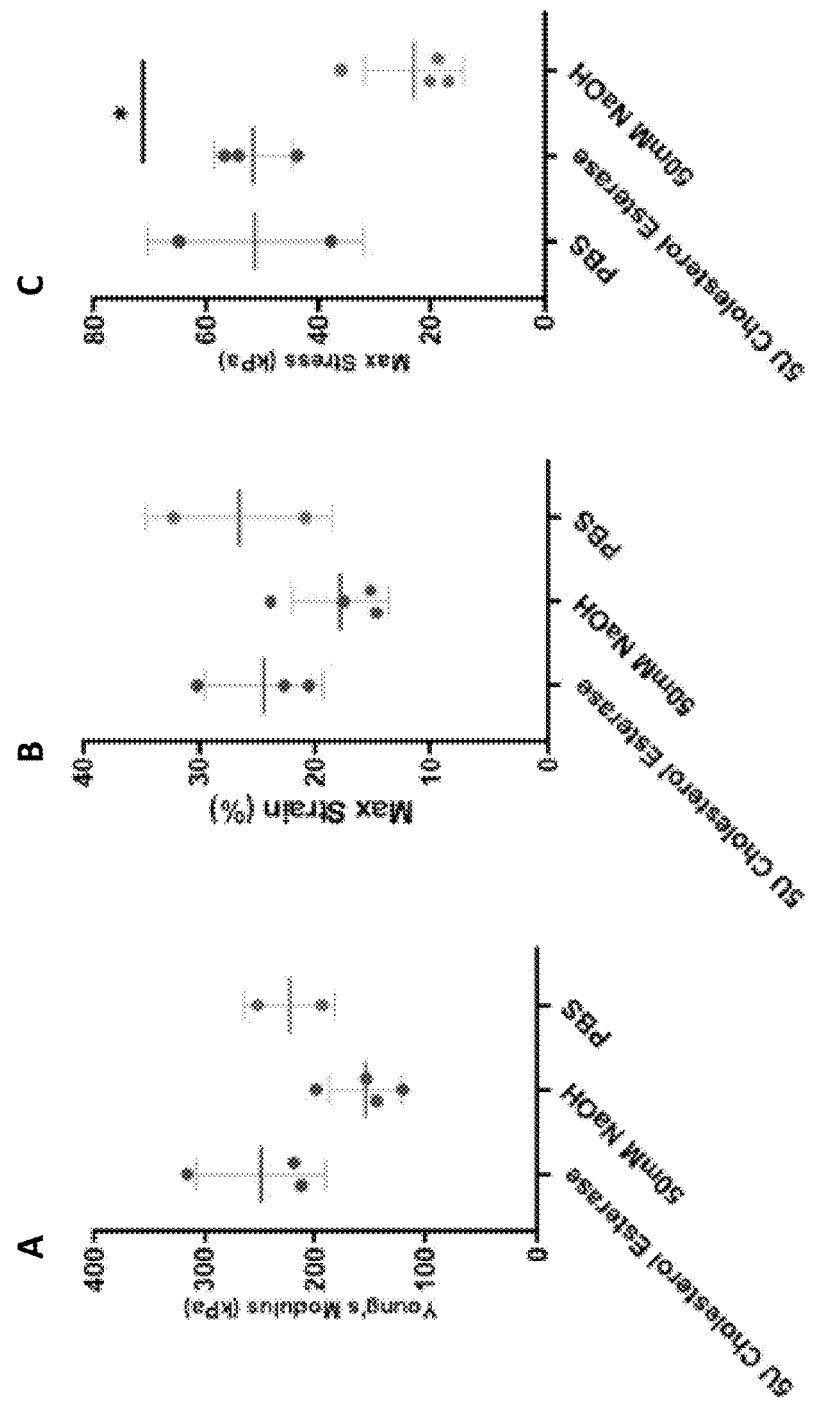
FIGS. 8A-8C show tensile test results of printed dog bones made of Ink A treated with esterase, NaOH, or PBS.
Figure 9:
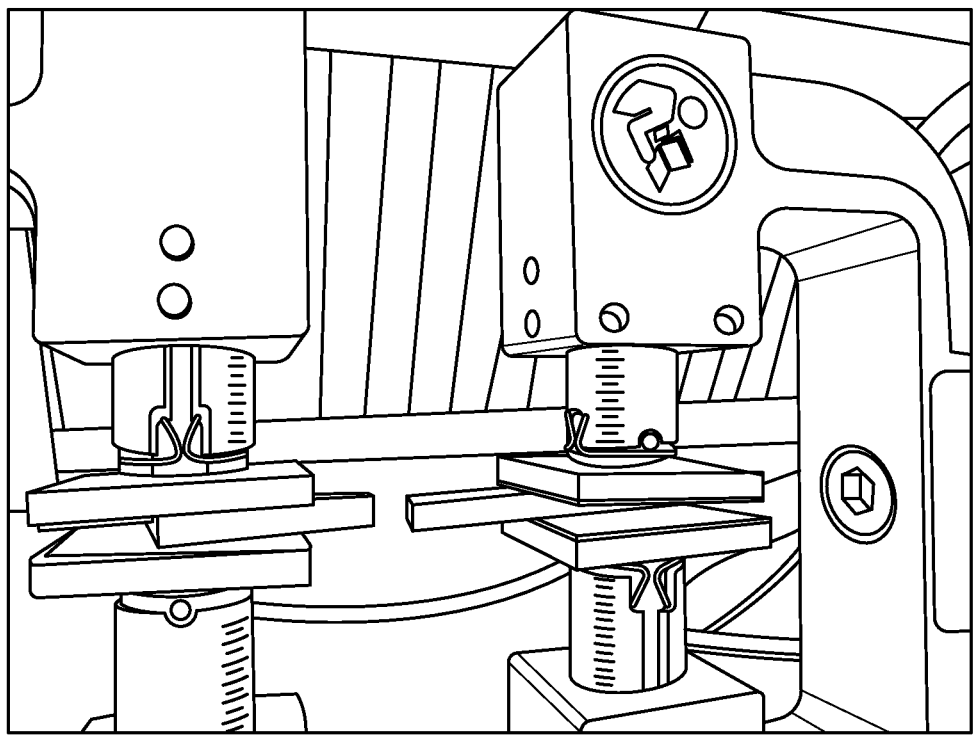
FIG. 9 shows an apparatus and sample object used in the tensile testing in Example 1 stretching printed object ink A after treatment with NaOH, to obtain the results in FIGS. 8A-8C.
Figure 10:
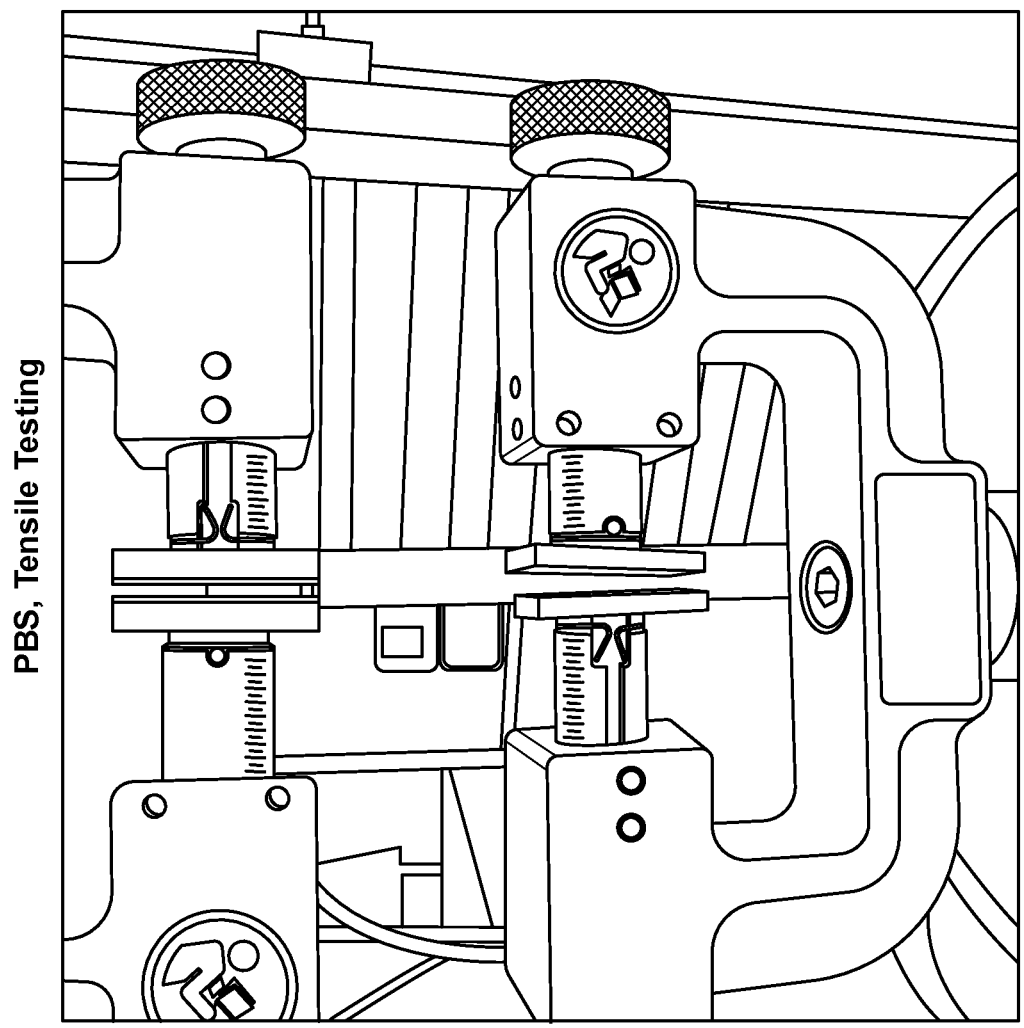
FIG. 10 shows an Apparatus and sample object used in the tensile testing in Example 1 stretching PBS treated sample of object printed with Ink A, to obtain the results in FIGS. 8A-8c.
Figure 11:
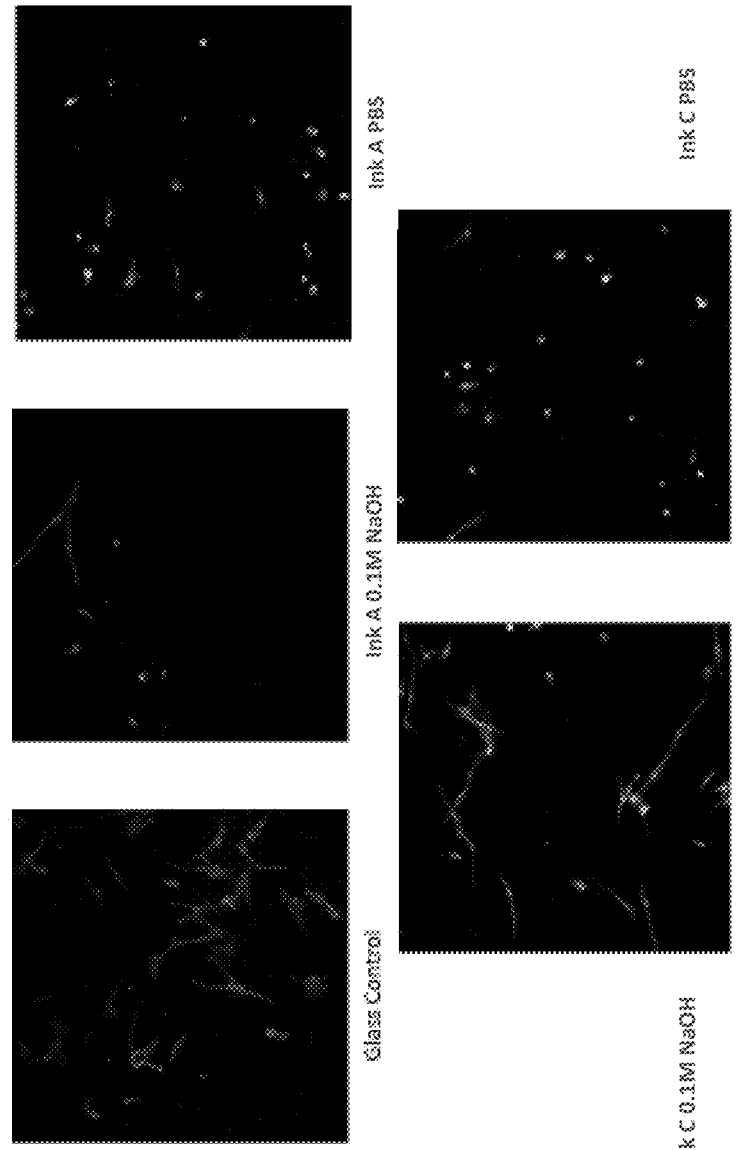
FIG. 11 shows human lung fibroblast cells attached to printed discs made of Ink A or C, treated with PBS or NaOH, and to glass control slides, after 1 day of culture.
Figure 12B:
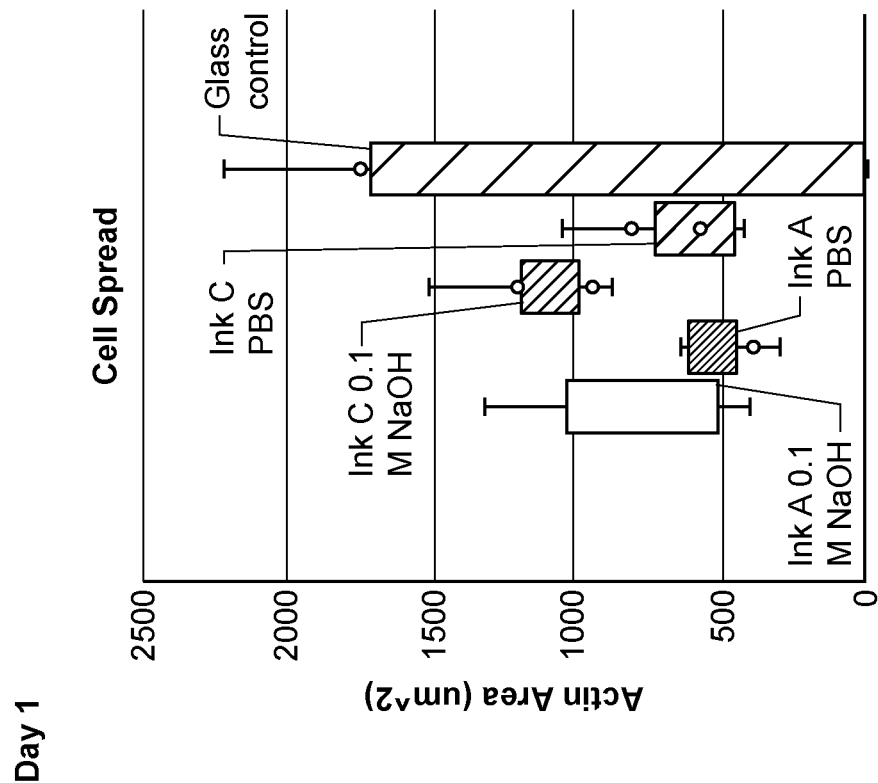
FIGS. 12A-12C show human lung fibroblast cells attached to printed dived made of Ink A and Ink C by treatment with esterase, NaOH, PBS, and to glass control, after 1 day of culture.
Figure 12A:
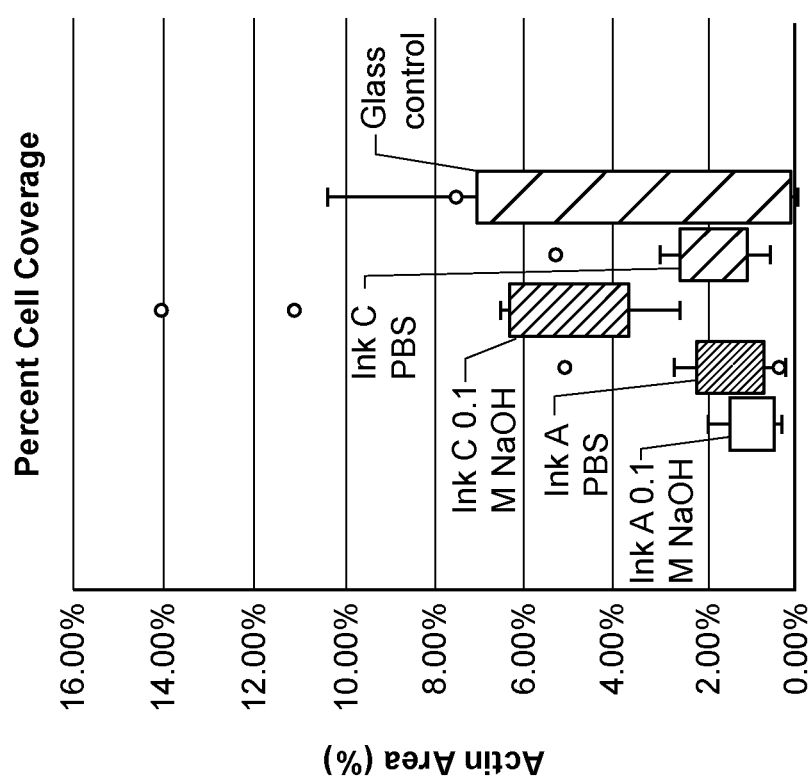
Figure 12C:
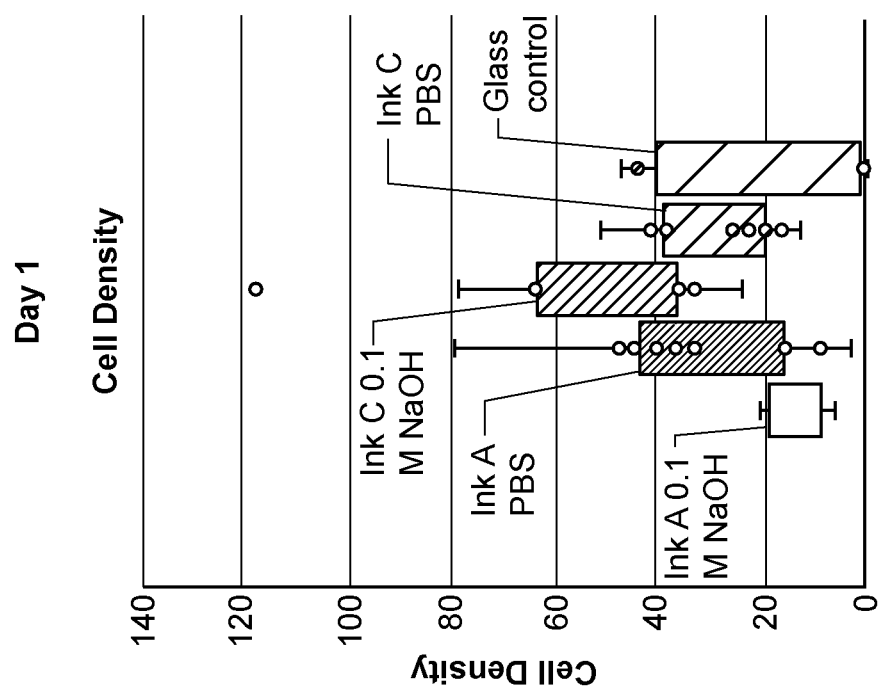
Figure 13:
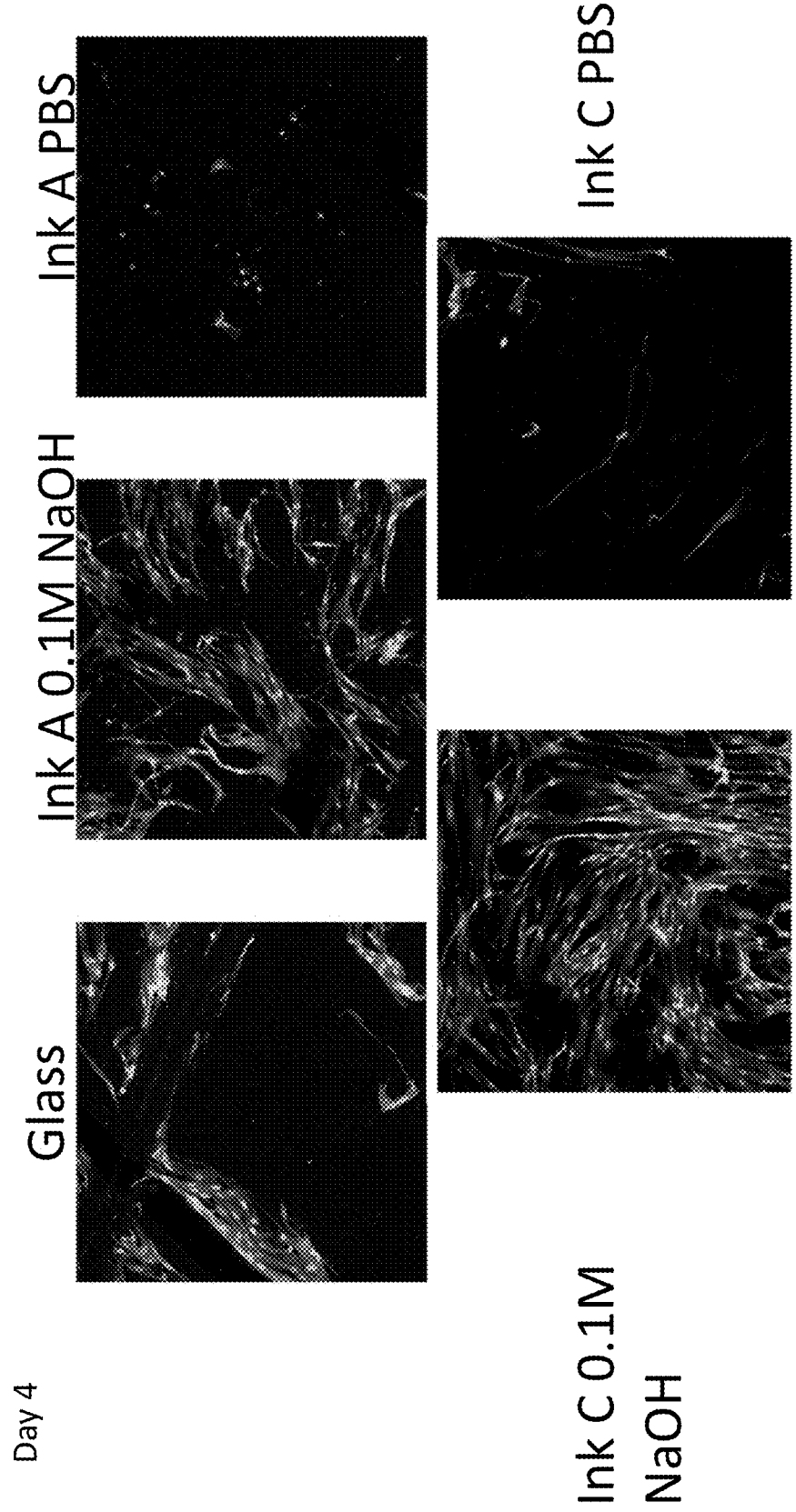
FIG. 13 shows human lung fibroblast cells cell attached to printed object made of Ink A and Ink C, treated with NaOH or PBS, after days 4 of culture.
Figures 14A, 14B, 14C:
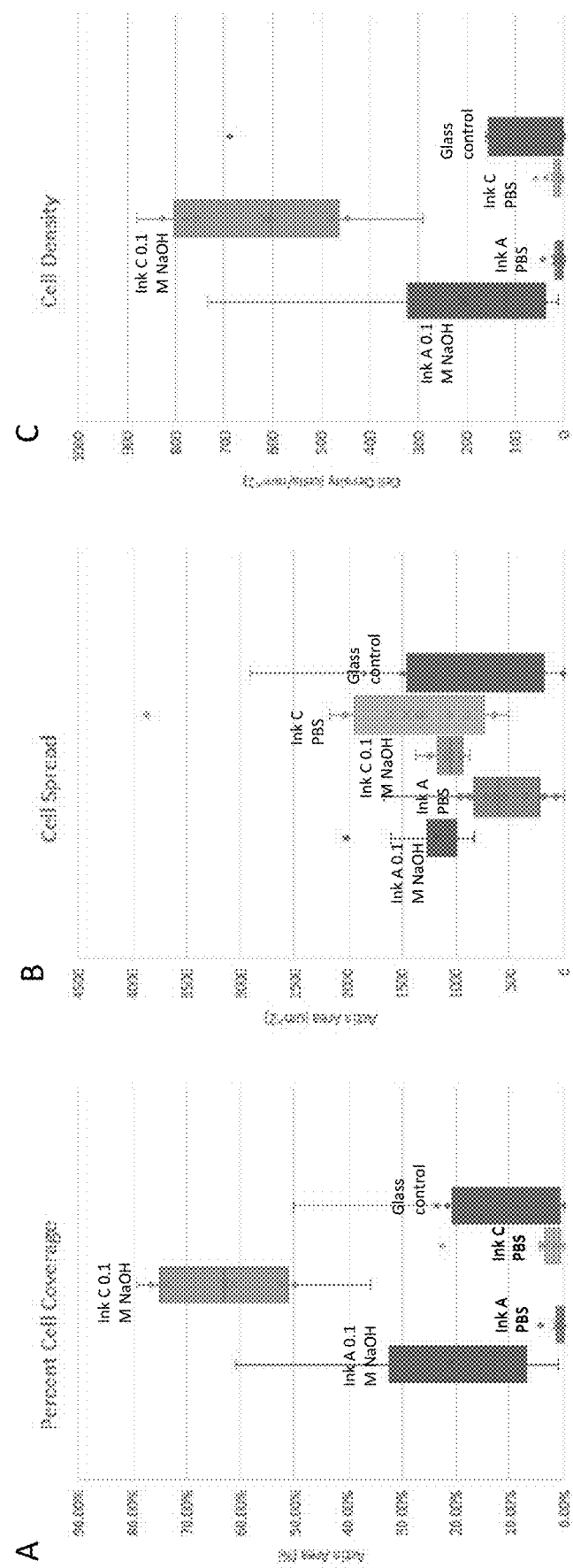
FIGS. 14A-14C show human lung fibroblast cells attached to printed discs made of Ink A and Ink C after treatment with esterase, NaOH, PBS, and to glass control, after 4 days of culture.
Figure 15A:
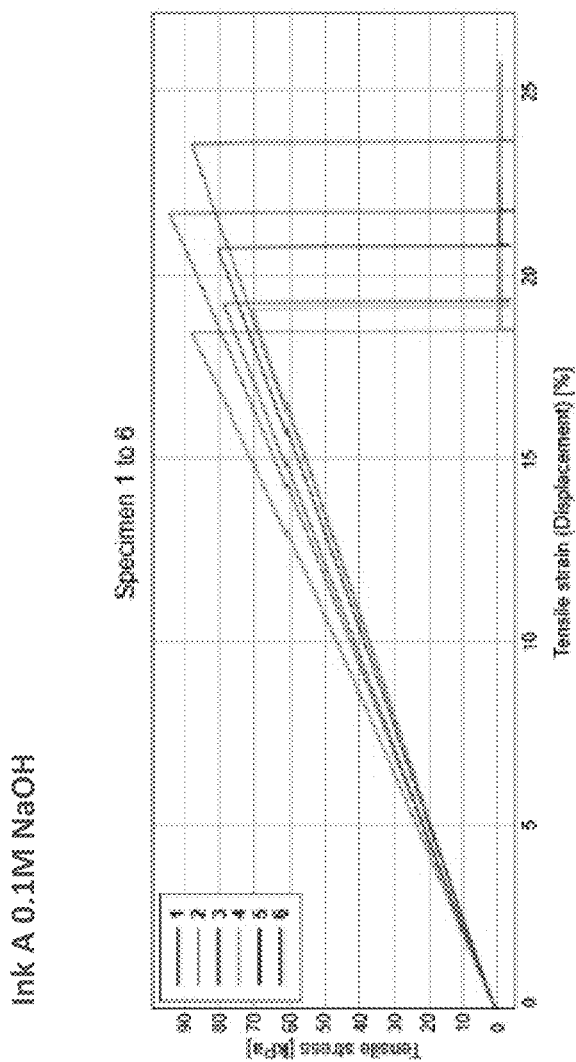
FIGS. 15A-15D show tensile strain displacement vs. tensile stress plots for printed dog bones made of Ink A treated with 0.1M NaOH (n=6) (FIG. 15A), Ink A treated with PBS (n=6) (FIG. 15B), Ink C treated with 0.1 M NaOH (n=4) (FIG. 15C), and Ink C treated with PBS (n=6) (FIG. 15D). The tensile strain displacement vs tensile stress plots were obtained using apparatus described in FIGS. 9 and 10.
Figure 15B:
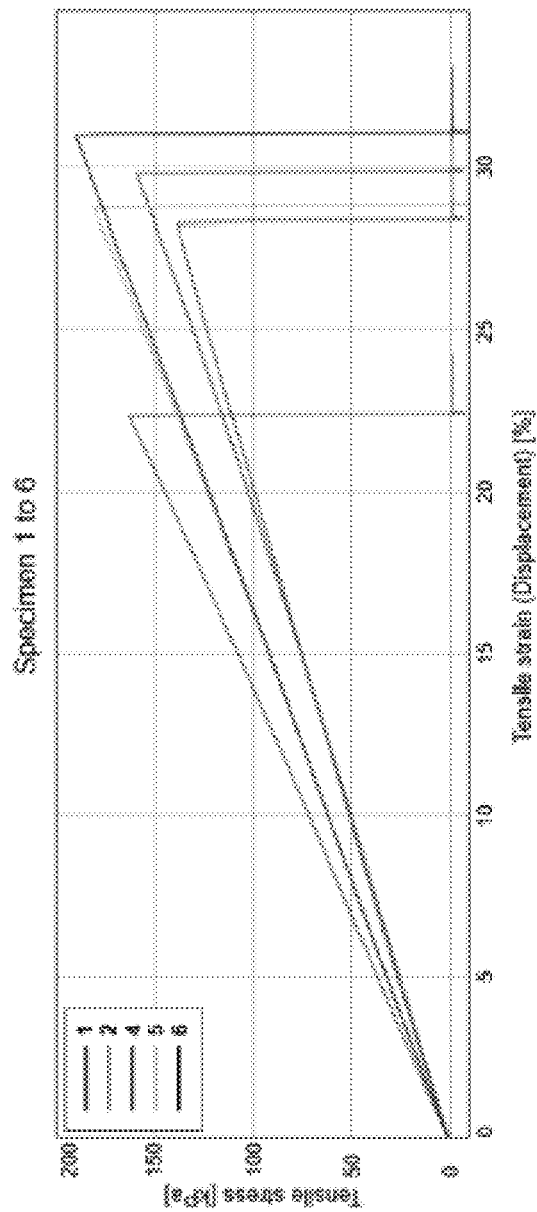
Figure 15C:
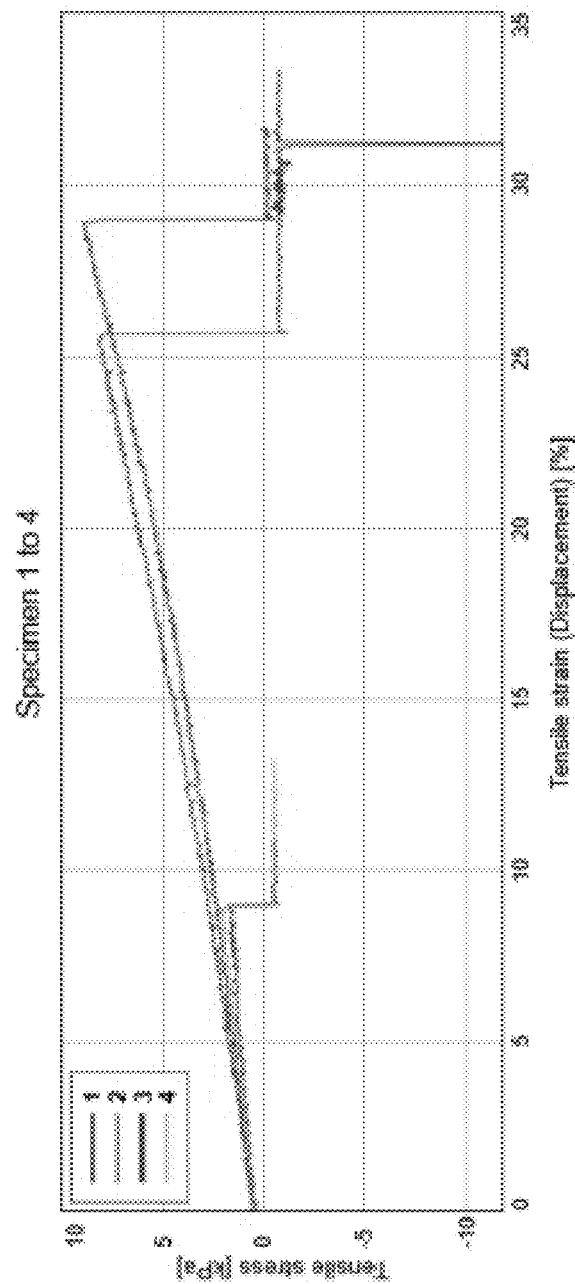
Figure 15D:
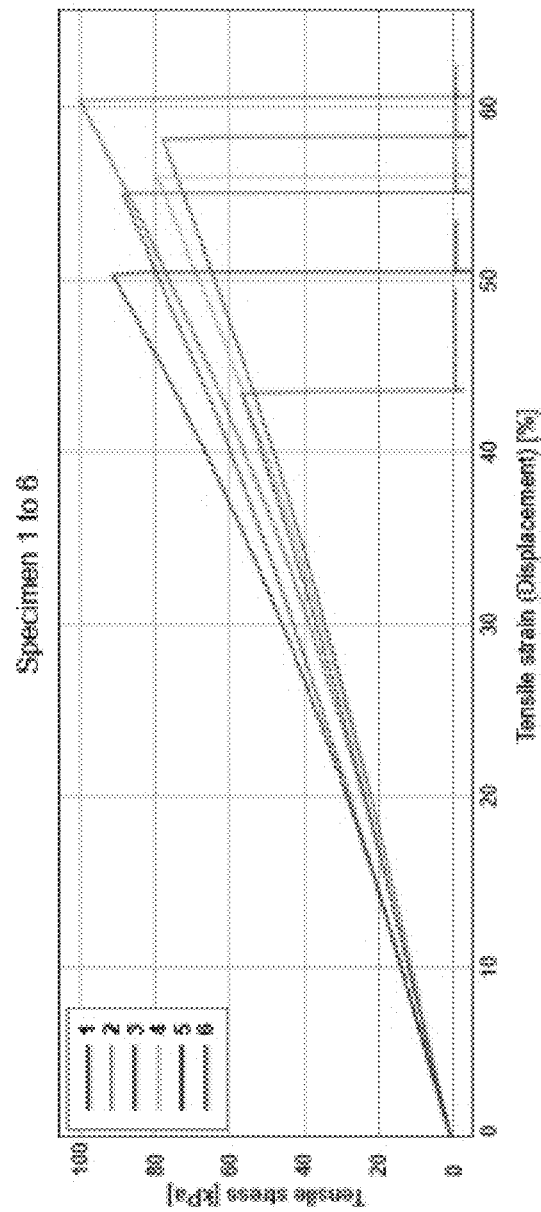
Figure 16:
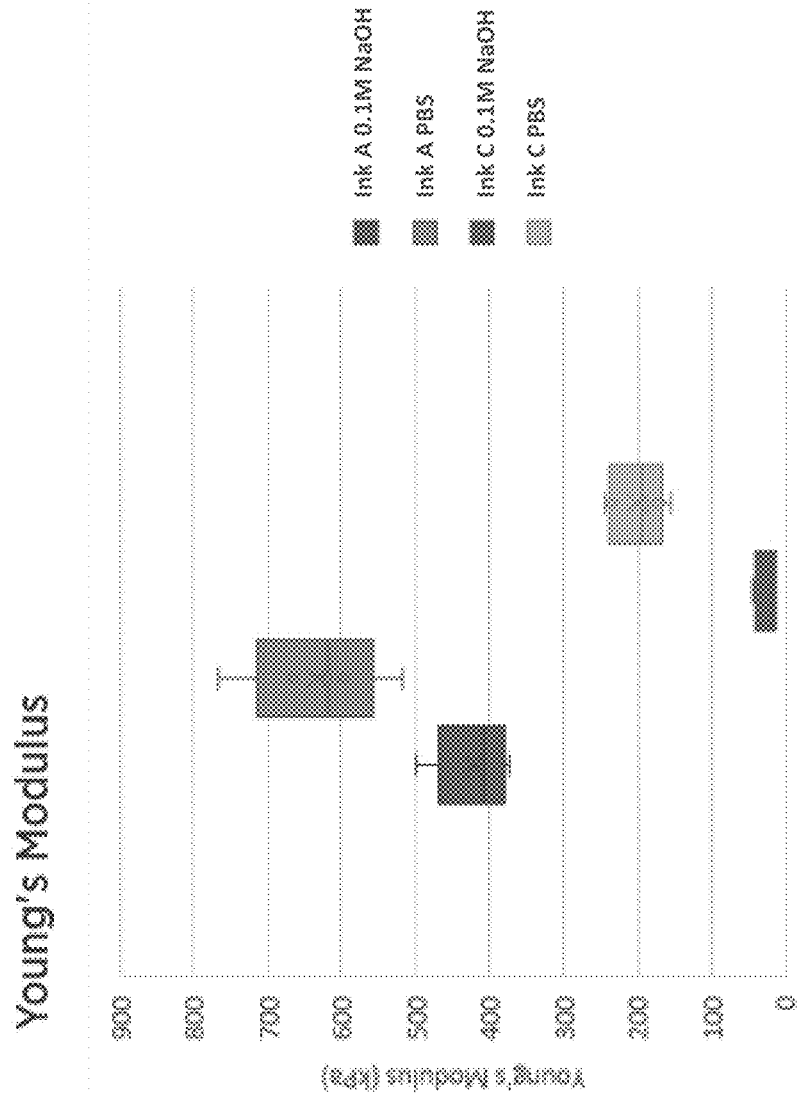
FIG. 16 shows the Young's modulus for printed dogbones made of Ink A and Ink C treated with NaOH or PBS. The Young's modulus were obtained using the tensile strains displacement vs tensile stress plots obtained in FIGS. 15A, 15B, 15C, and 15D.
Figures 17A, 17B:
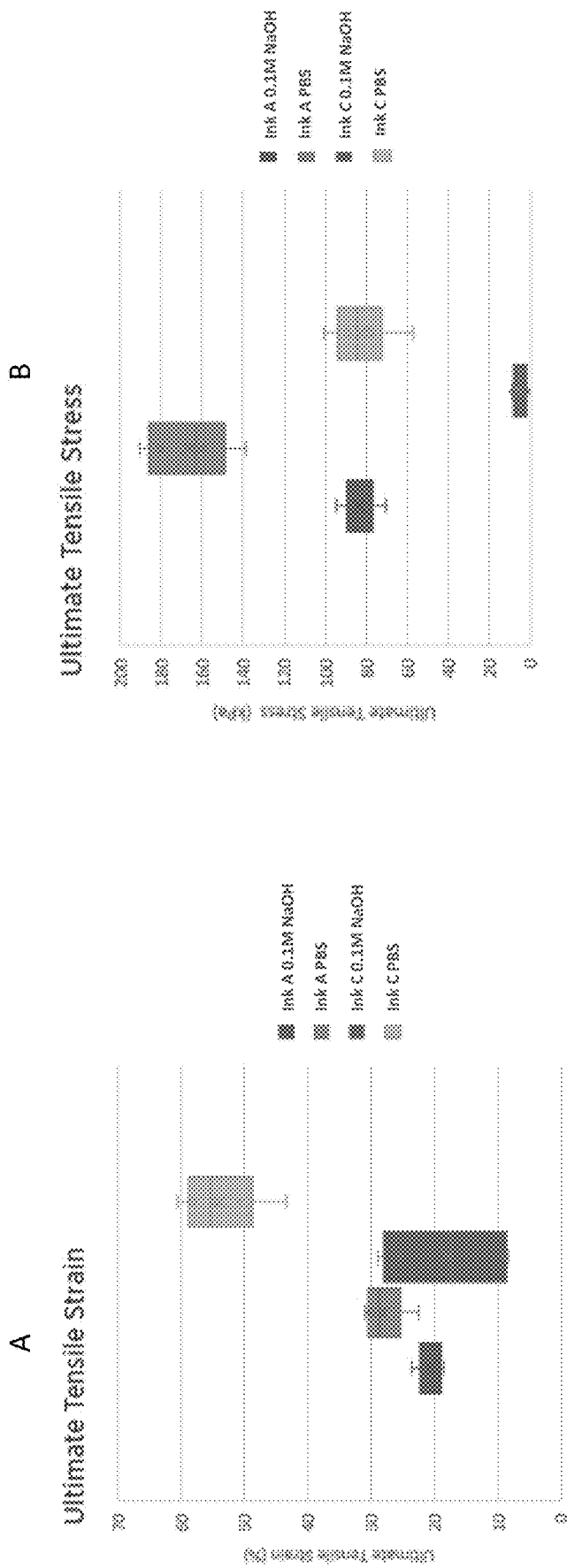
FIGS. 17A-17B shows the change tensile mechanical properties for Ink A and Ink C samples treated with NaOH or PBS.
Figure 18:
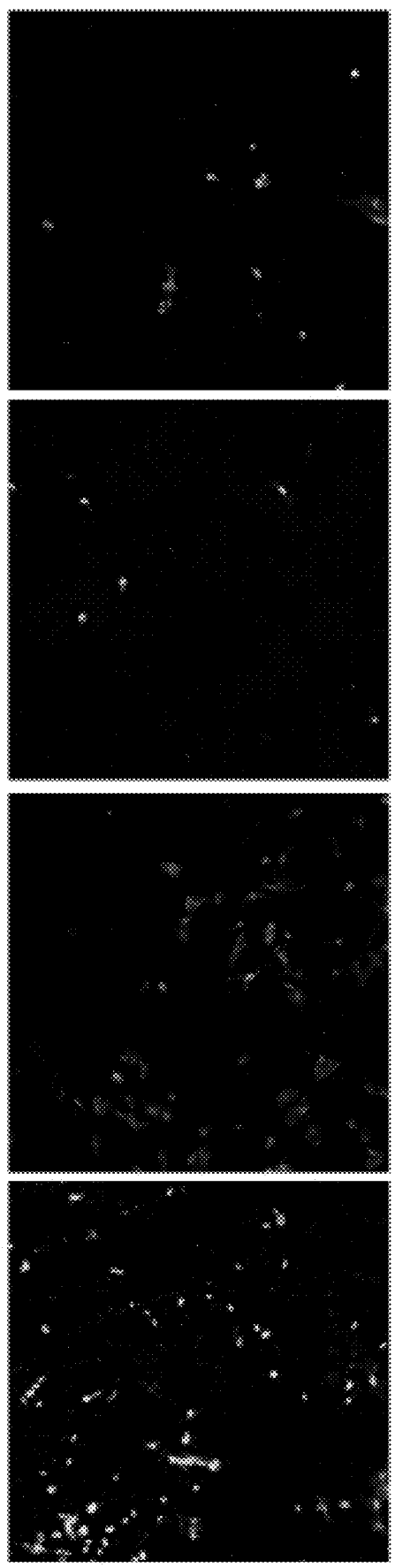
FIG. 18 shows attachment of human pulmonary artery endothelial cells to printed Fischer disc of Ink A, treated with NaOH, esterase, and PBS, and to glass control, after day 4.
Figures 19A, 19B, 19C:
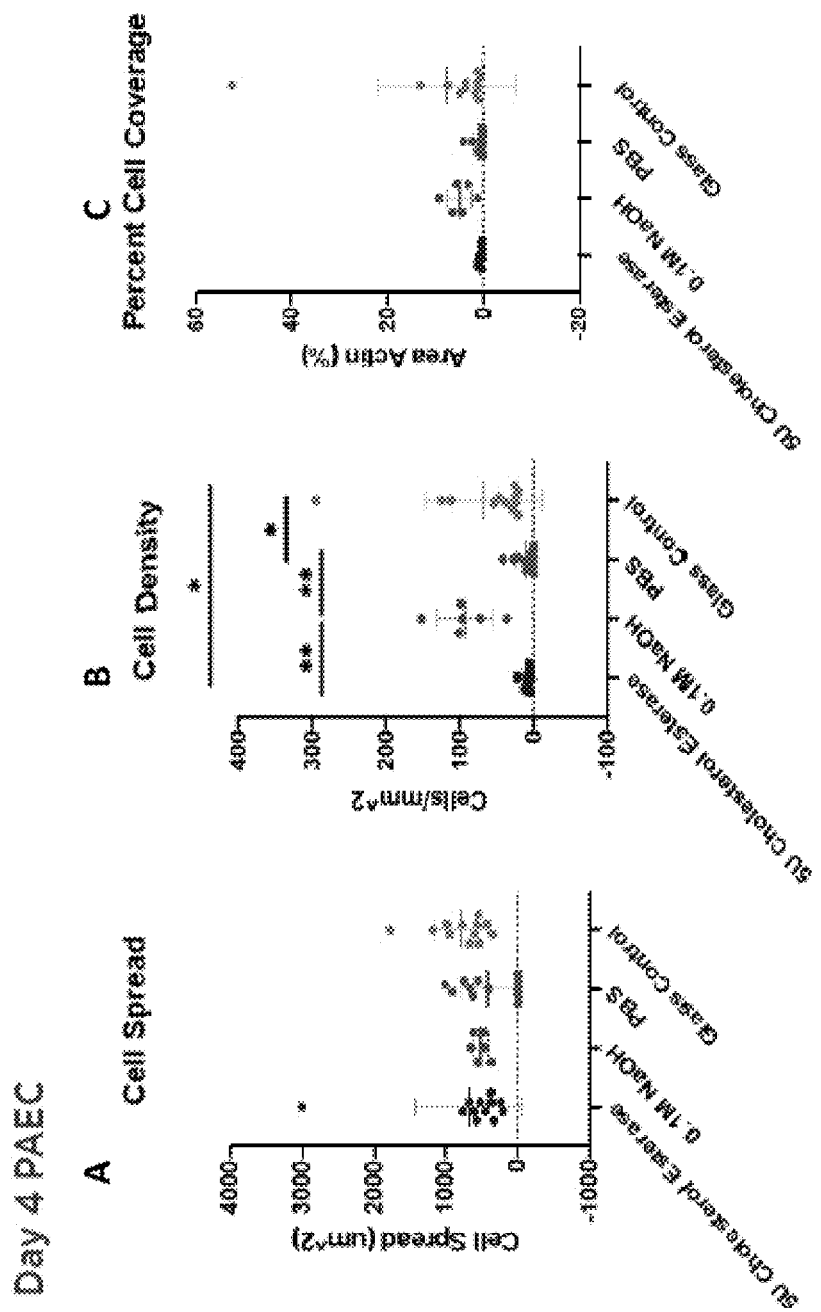
FIGS. 19A-19C show attachment of human pulmonary artery endothelial cells to printed Fischer disc made of Ink A treated with esterase, NaOH, PBS, or glass control, after 4 days of culture.
Figure 20:
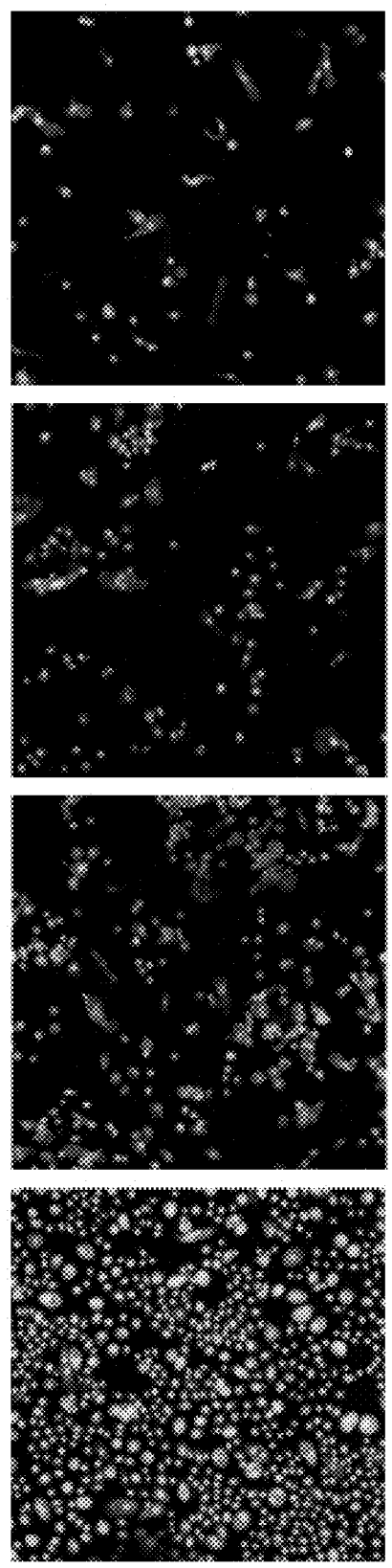
FIG. 20 shows attachment of human of small airway epithelial cells to printed Fischer disc made of Ink A, treated with NaOH, esterase, and PBS, and to glass control, after 4 days of culture.
Figures 21A, 21B, 21C:
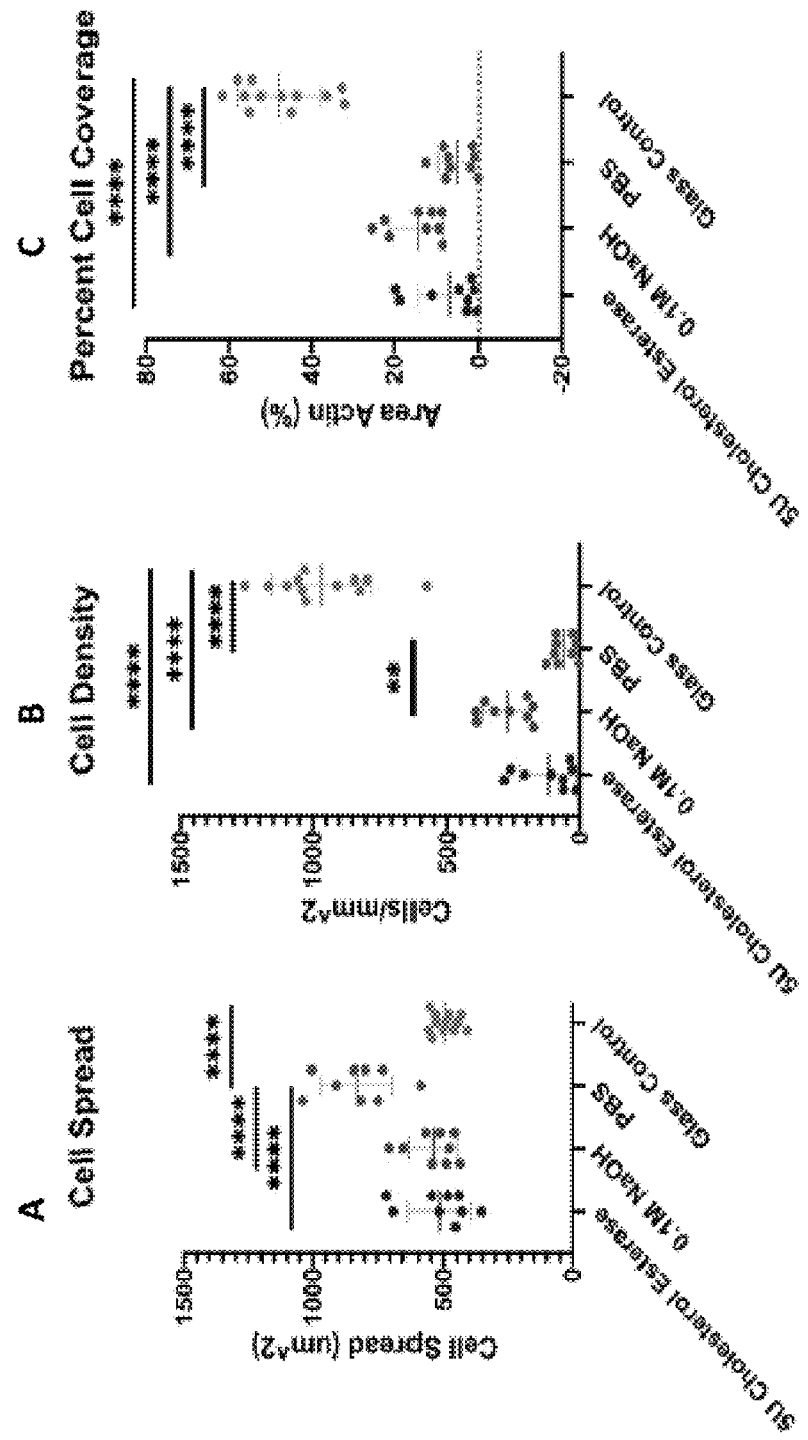
FIGS. 21A-21C show attachment of human of small airway epithelial cells to printed Fischer disc made of Ink A treated with esterase, NaOH, PBS, or glass control, after day 4.
Figure 22:
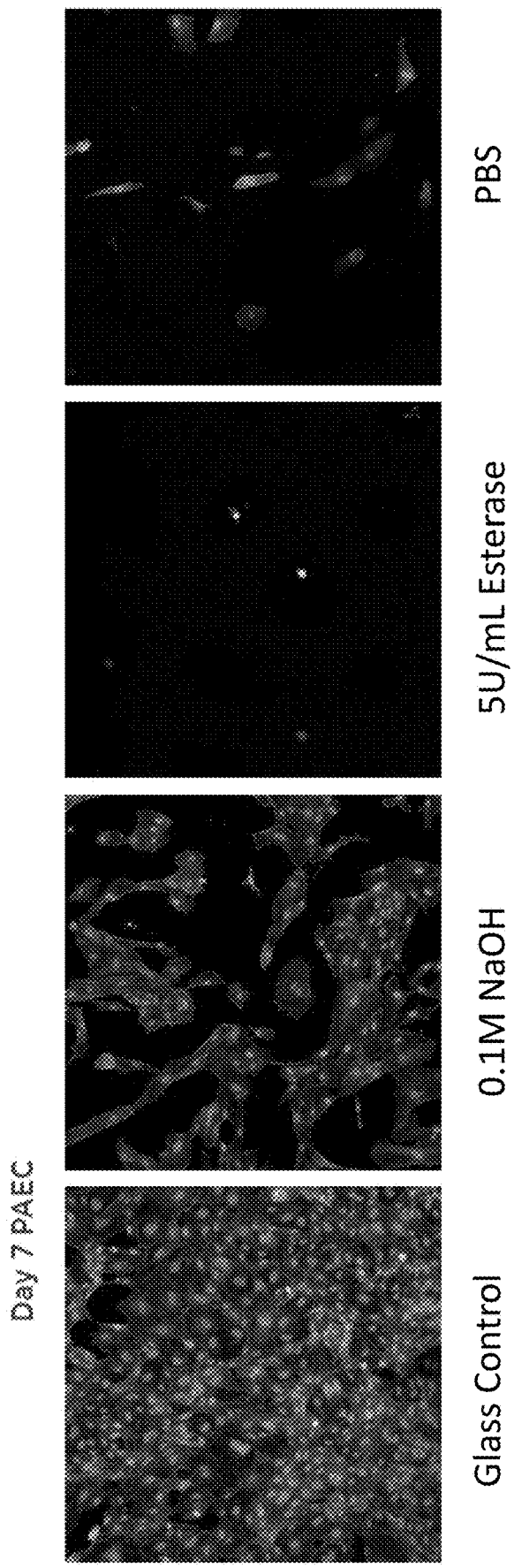
FIG. 22 shows attachment of human pulmonary artery endothelial cells to printed Fischer disc made of Ink A, treated with NaOH, esterase, and PBS, and to glass control, after 7 days of culture.
Figures 23A, 23B, 23C:
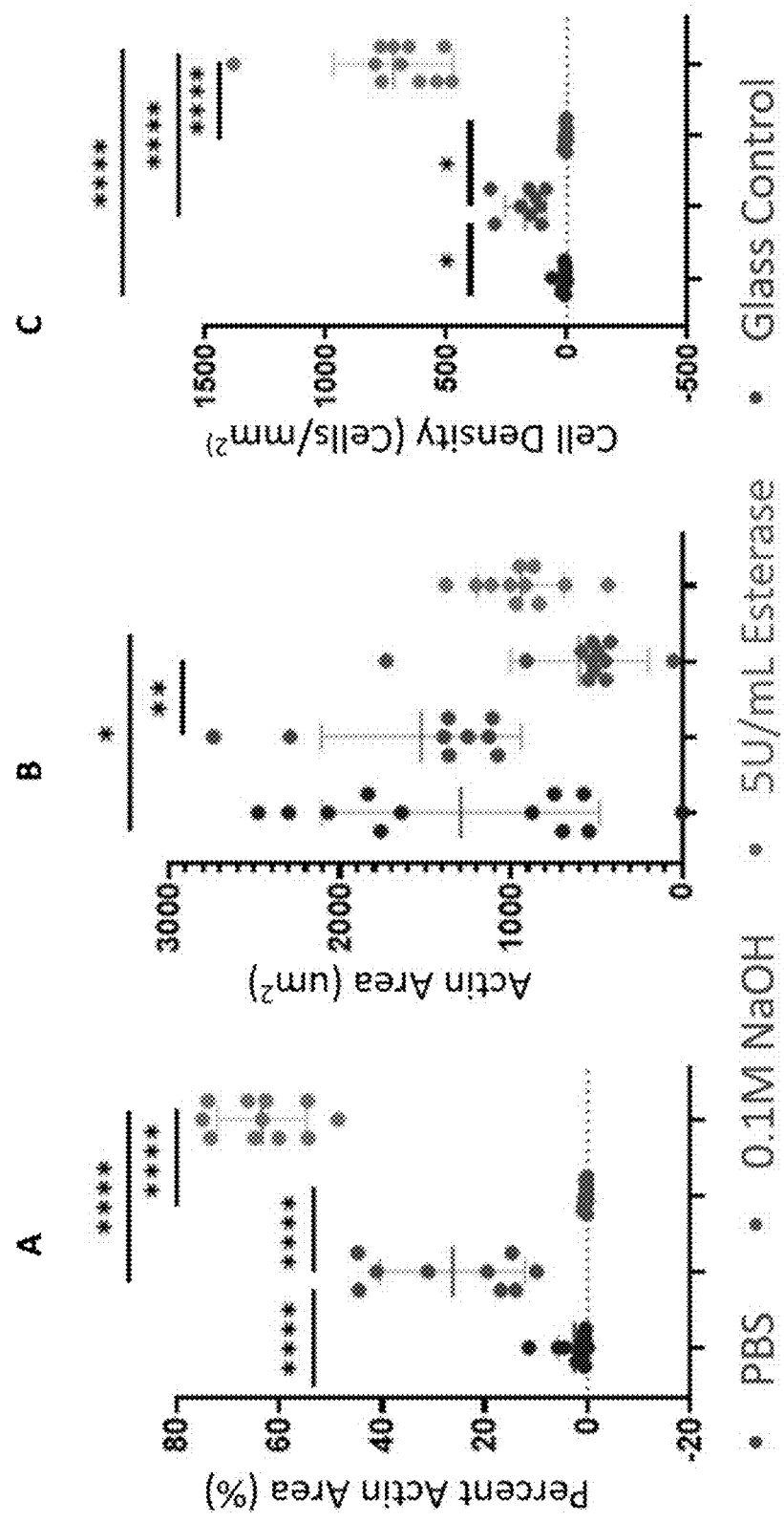
FIGS. 23A-23C shows attachment of human pulmonary artery endothelial cells to printed Fischer disc made of Ink A treated with esterase, NaOH, PBS, or glass control, after 7 days of culture.
Figures 25A, 25B, 25C:
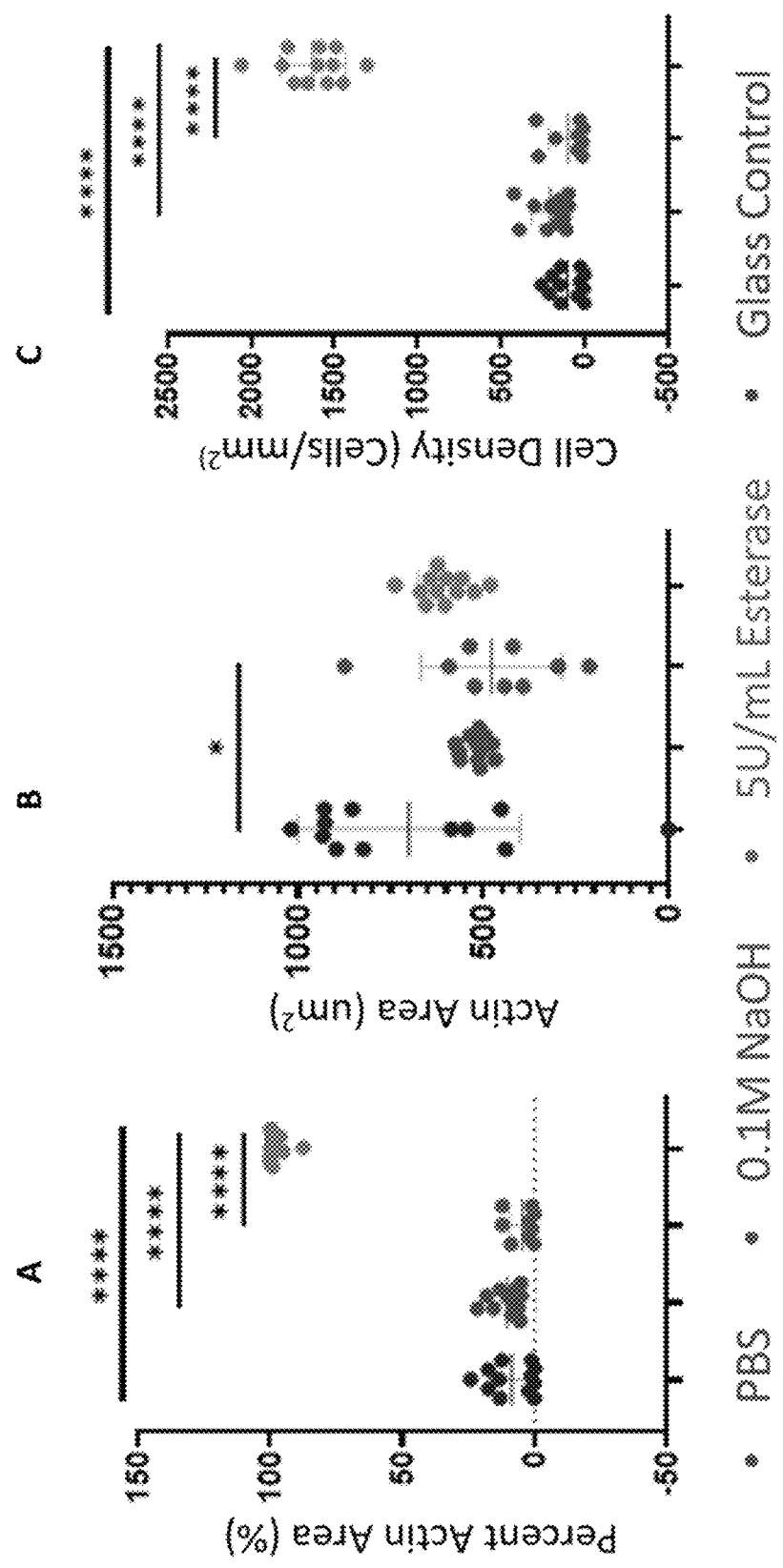
FIGS. 25A-25C shows attachment of human of small airway epithelial cells to printed Fischer disc made of Ink A treated with esterase, NaOH, PBS, or glass control, after day 7.
Figures 26A, 26B, 26C:
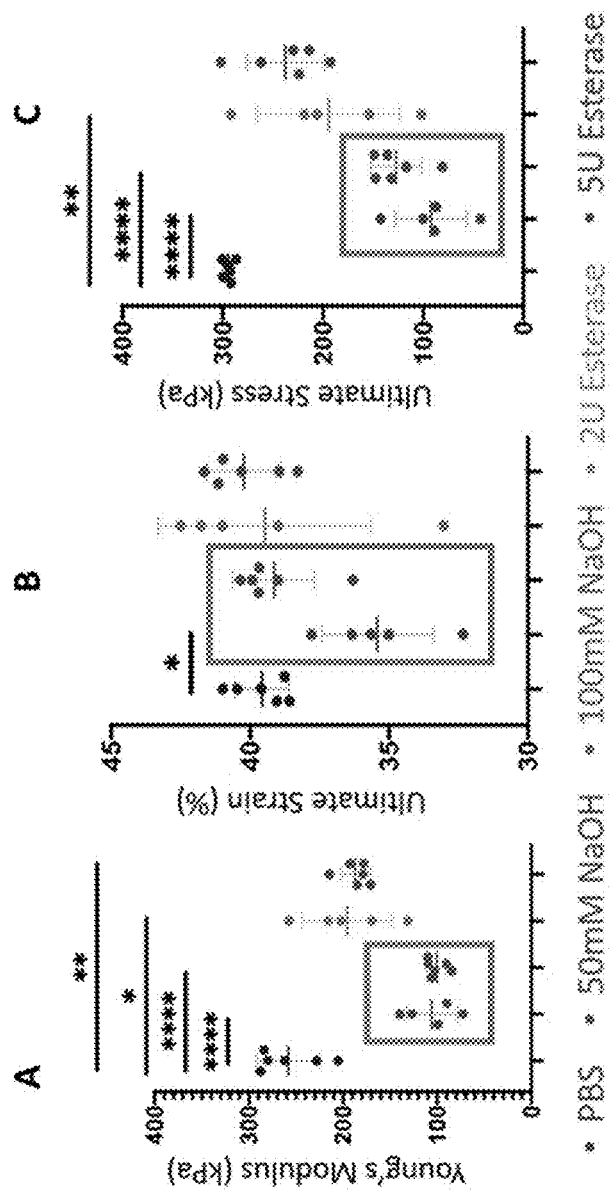
FIGS. 26A-26C shows compressive mechanical properties of a printed Fischer disc of Ink A in Example 4 without exposure to enzymes, with exposure to sodium hydroxide, and with exposure to cholesterol esterase.
Figure 27:
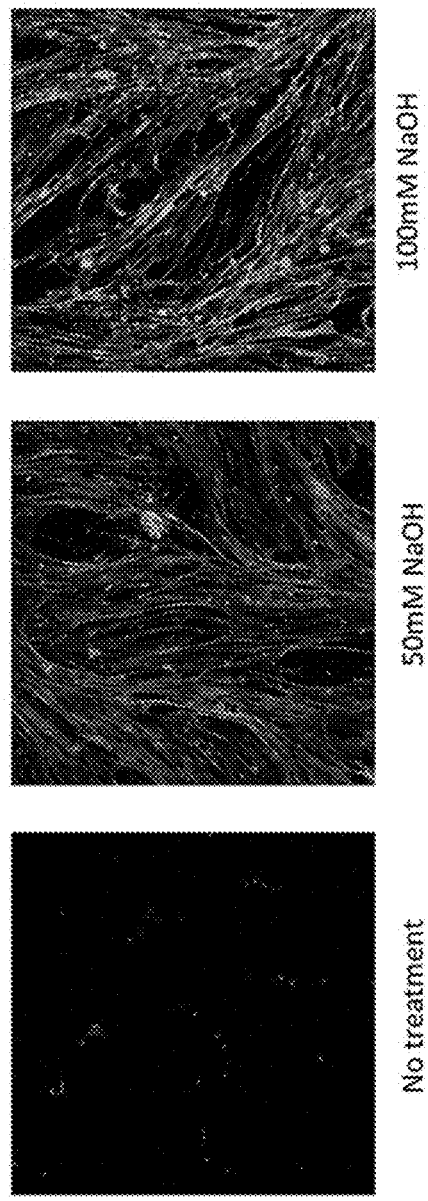
FIG. 27 shows an embodiment of human lung fibroblast cells seeded on a printed Fischer disc of Ink A in the examples without exposure to enzymes and with exposure to NaOH.
Figure 28:
FIG. 28 shows an embodiment of human lung fibroblast cells seeded on a printed Fischer disc of Ink A in the examples without exposure to enzymes and with exposure to cholesterol esterase.
Figure 29:
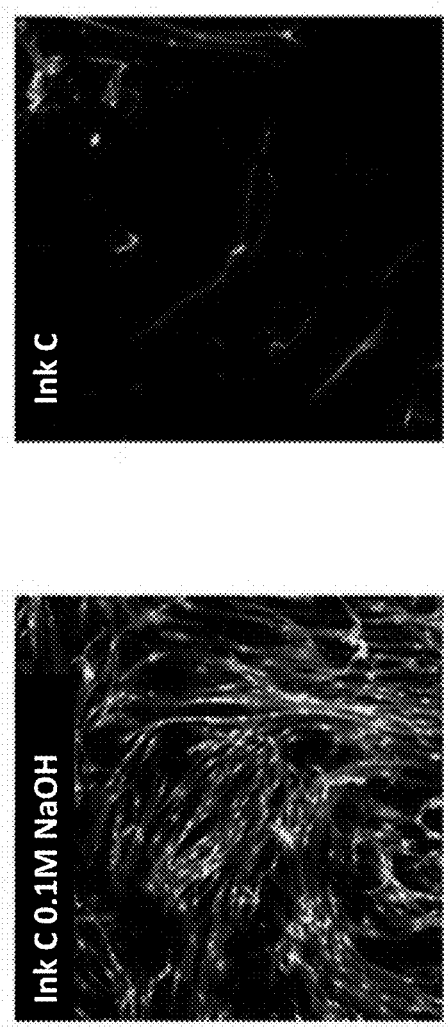
FIG. 29 shows an embodiment of human lung fibroblast cells seeded on a printed Fischer disc of Ink C in the examples without exposure to enzymes and with exposure to NaOH.

Applicant has discovered that printed objects such as polymeric scaffolds, made of an ink composition comprising polyethylene oxide diacrylates and protein based inks, demonstrate an increase in cell attachment and altered mechanical properties when exposed to sodium hydroxide or cholesterol esterase. Thus, methods in the disclosure may be used to 3D print non-bioactive 3D objects which may employ certain chemistries to render them bioactive and modulate their swelling and mechanical properties.

For 3D printed objects using these inks, Applicant has found that sodium hydroxide treatment of the object increased cell attachment with significant changes to the mechanical properties and swelling, while cholesterol esterase increased cell attachment to the object with minimal changes the mechanical properties and swelling. The extent of cross-linking was also able to be used to tune the properties of the materials. More crosslinked inks exhibited smaller decreases in mechanical properties for solid discs when subjected to NaOH and esterase treatments. 3D printed samples with larger channels and smaller wall thickness increase ultimate strain and decrease Young's modulus and ultimate stress upon treatment. The treatment of the 3D printed objects with NaOH resulted in increased cell attachment of Lung Fibroblast (LFN), Porcine Aorta Endothelial Cells (PAEC), and Small Airway Epithelial Cells (SAEC) as further detailed in the Examples.

Polymeric Scaffold Compositions

Certain embodiments of this disclosure include a composition, 3D printed object, or polymeric scaffold comprising one or more polymerized moieties of formula (I):

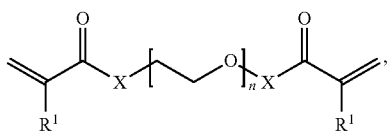

wherein:
each $R^1$ is independently selected from H or $CH_3$;
each X is independently selected from O or NH; and
n is from 1 to 500.

In some embodiments, one of the polymerized moieties comprises both $R^1$ being H. In some embodiments, one of the polymerized moieties comprises both $R^1$ being $CH_3$. In some embodiments, one of the polymerized moieties comprises both X being O. In some embodiments, one of the polymerized moieties comprises both X being NH. In some embodiments, one of the polymerized moieties comprises on X being O and the other X being NH. In some embodiments, n of each polymerized moiety is independently 1-10, 10-25, 25-50, 50-75, 75-100, or 100-150.

In some embodiments, the scaffold comprises polymerized poly(ethyelene glycol) di(meth)acrylate moieties, polymerized poly(ethyelene glycol) di(meth)acrylamide moieties, polymerized poly(ethyelene glycol) (meth)acrylate/(meth)acrylamide moieties, and mixtures thereof.

Different functional groups within these moieties include ethers, amides, and esters that react differentially. The ethers are subject to degradation via oxidation, esters are subject to hydrolysis, and the amides are biostable as shown in Scheme 1. PEGDA degrades primarily due to hydrolysis of the end group ester linkages rather than via oxidation of the ether backbone.

Scheme 1

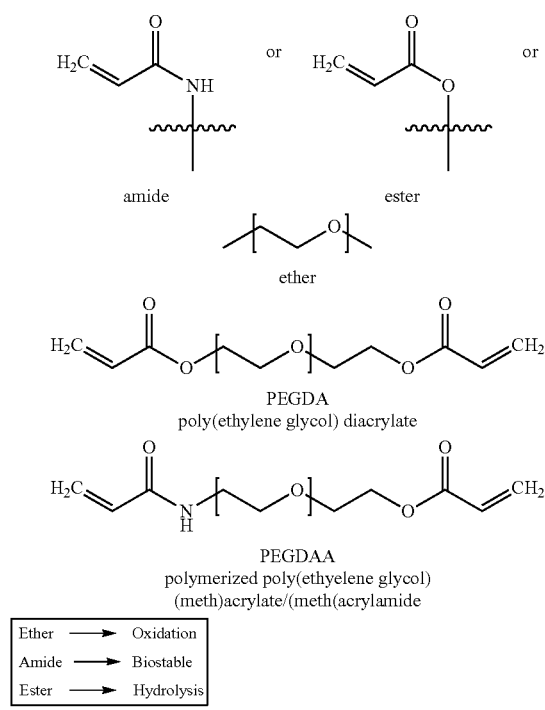

In some embodiments, the scaffold, object, or composition further comprises collagen and/or polymerized (meth) acrylated collagen (ColMA, for methacrylated collagen). In some embodiments, the (meth)acrylated collagen comprises collagen comprising (meth)acrylamides at sites corresponding to free amines, for example, to lysine. In some embodiments, the collagen comprising amines functionalized with (meth)acrylate moieties to have a (meth)acrylamide at the functionalized amine. In some embodiments, the degree of functionalization, or percent of amine groups of collagen functionalized, is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, any one or more of the polymerized moieties may be present at about 0% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 100%, by weight, based on the total weight of the scaffold, composition, or printed object.

In some embodiments, collagen and/or polymerized (meth)acrylated collagen may be present at about 0% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 100%, by weight, based on the total weight of the scaffold, composition, or printed object.

In certain embodiments, the scaffold is a 3D-printed scaffold. The skilled artisan would appreciate the methods of printing known in the art, and non-limiting examples include selective laser sintering (SLS) method, a fused deposition modeling (FDM) method, a 3D inkjet printing method, a digital light processing (DLP) method, and a stereo lithography method. In the fused deposition modeling (FDM) method, the Inks are deposited by an extrusion head, which follows a tool-path defined by a CAD file. The materials are deposited in layers as fine as 25 µm thick, and the part is built from the bottom up, one layer at a time. In some embodiments, the layers are from 10 µm to about 50 µm thick. Some 3D printers based on the fused deposition modeling method are equipped with dual print nozzle heads that can extrude two different materials, one being a building material and the other being a support, such as a pillar, material. The support material can be washed with water.

3D inkjet printing is effectively optimized for speed, low cost, high resolution, and ease-of-use, making it suitable for visualizing during the conceptual stages of engineering design through to early-stage functional testing. Complicated 3D articles in the ink-jet printing method are produced from ink compositions by jetting followed by UV/Vis light. The photo-curable ink in the ink-jet printing process may be jetted through several nozzles on the building platform with a pattern defined by a CAD file.

One of the most efficient technologies among 3D printing technologies is a digital light process (DLP) method or stereo lithography (SLA). In a 3D printer using the DLP or SLA method, the ink material is layered on a vat or spread on a sheet, and a predetermined area or surface of the ink is exposed to ultraviolet-visible (UV/Vis) light that is controlled by a digital micro-mirror device or rotating mirror. In the DLP method, additional layers are repeatedly or continuously laid and each layer is cured until a desired 3D article is formed. The SLA method is different from the DLP method in that ink is solidified by a line of radiation beam. Other methods of 3D printing may be found in 3D Printing Techniques and Processes by Michael Degnan, December 2017, Cavendish Square Publishing, LLC, the disclosure of which is hereby incorporated by reference.

In certain embodiments, the scaffold is substantially solid (e.g., does not comprise channels or is printed without a specific internal pattern). In other embodiments, the scaffold is not substantially solid. For example, when the scaffold is not substantially solid, then the scaffold can include, e.g., channels and walls defining those channels. In some embodiments, these channels and walls have been formed via 3D printing of the specific channels and walls. In certain embodiments that include channels, then channels have a width of about 200 to about 500 μm (e.g., about 200, 225, 250, 275, 300, 325, 350, 375, 400, 425, 450, 475 or 500 μm). It will be understood that some embodiments have more than one width of channel, and in some embodiments, at least 50, 60, 70, 80, 90, 95, 98, 99, or 100 percent of the channels have a width discussed in embodiments herein. In certain embodiments that include walls, then walls have a width of about 150 to about 400 μm (e.g., about 150, 175, 200, 225, 250, 275, 300, 325, 350, 375, or 400 μm). It will be understood that some embodiments have more than one width of walls, and in some embodiments, at least 50, 60, 70, 80, 90, 95, 98, 99, or 100 percent of the walls have a width discussed in embodiments herein. In some embodiments, the scaffold includes a substantially solid portion and a non-substantially solid. These embodiments include, e.g., a non-substantially solid portion that comprises channels and walls defining those channels, such as the above-described embodiments.

The polymeric scaffold of certain embodiments includes polymerized poly(ethylene glycol) di(meth)acrylate moieties, poly(ethyelene glycol)(meth)acrylamide moieties, polymerized poly(ethyelene glycol) (meth)acrylate/(meth)acrylamide moieties, or a mixture thereof. In some embodiments, the polymeric scaffold comprises polymerized poly(ethyelene glycol) diacrylate moieties. In some embodiments, the weight average molecular weight (Mw) of the poly(ethyelene glycol) di(meth)acrylate, poly(ethyelene glycol)(meth)acrylamide, or poly(ethyelene glycol) (meth)acrylate/(meth)acrylamide, is about 400 Da to about 20,000 Da (e.g., about 500 Da to about 10,000 Da or about 500 Da to about 5,000). In some embodiments, the Mw is about 400 Da, 500 Da, 600 Da, 700 Da, 800 Da, 900 Da, 1000 Da, 1100 Da, 1200 Da, 1300 Da, 1400 Da, 1500 Da, 1600 Da, 1700 Da, 1800 Da, 1900 Da, 2000 Da, 2100 Da, 2200 Da, 2300 Da, 2400 Da, 2500 Da, 2600 Da, 2700 Da, 2800 Da, 2900 Da, 3000 Da, 3100 Da, 3200 Da, 3300 Da, 3400 Da, 3500 Da, 3600 Da, 3700 Da, 3800 Da, 3900 Da, 4000 Da, 4100 Da, 4200 Da, 4300 Da, 4400 Da, 4500 Da, 4600 Da, 4700 Da, 4800 Da, 4900 Da, 5000 Da, 5100 Da, 5200 Da, 5300 Da, 5400 Da, 5500 Da, 5600 Da, 5700 Da, 5800 Da, 5900 Da, 6000 Da, 6100 Da, 6200 Da, 6300 Da, 6400 Da, 6500 Da, 7000 Da, 7500 Da, 8000 Da, 8500 Da, 9000 Da, 9500 Da, 10000 Da, 15000 Da, or 20000 Da.

In some embodiments, the scaffold, object, or composition of the disclosure comprises a cross linked polymer. In some embodiments, the polymer is about 0% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 100% cross-linked, based on the percentage of the cross-linkable moieties in the polymer. Cross linkable moieties may include, for example, (meth)acrylate groups.

In some embodiments, a scaffold, object, or composition of the disclosure comprises a plurality of substantially parallel pillars there through. Pillars may be created by rotating Fischer foam and slicing. Some of the triple period minimal surface can align to form straight-line solid tunnels which results in the pillar formation. The pillars may increase ultimate stress without effecting the ultimate strain or Young's modulus In some embodiments, the scaffold, ink or composition may further comprise additional polymerized moieties or other additives selected from the group consisting of at least one water-compatible organic polymer, alcohol-compatible organic polymer, other additives, and combinations thereof. The polymer may be homopolymeric, heteropolymeric (including, but not limited to, cross-polymers or co-polymers of any co-monomer distribution), and may be linear, branched, hyperbranched, dendrimeric, or crosslinked to any extent. Examples of suitable polymers include, but are not limited to, poly(ethylene glycol)-block-poly(ε-caprolactone), polycaprolactone, polyvinyl alcohol, gelatin, methylcellulose, hydroxyethyl methyl cellulose, hydroxypropyl methyl cellulose, polyethylene oxide, polyacrylamides, polyacrylic acid, polymethacrylic acid, salts of polyacrylic acid, salts of polymethacrylic acid, poly(2-hydroxyethyl methacrylate), polylactic acid, polyglycolic acid, polyvinyl-alcohol, polyanhydrides such as poly(methacrylic) anhydride, poly(acrylic) anhydride, polysebasic anhydride, collagen, poly(hyaluronic acid), hyaluronic acid-containing polymers and copolymers, polypeptides, dextran, dextran sulfate, chitosan, chitin, agarose gels, fibrin gels, soy-derived hydrogels and alginate-based hydrogels such as poly (sodium alginate), and combinations thereof. In some embodiments, the compositions further comprise polymerized hydroxypropyl acrylate (HPA), or lithium phenyl-2,4,6-trimethylbenzoylphosphinate (LAP).

In some embodiments, the additive comprises a photoinitiator. The photo initiator is not particularly limited. In some embodiments, it is such as to allow for onset times from 0-60 seconds. In some embodiments, the photo initiator comprises lithium phenyl-2,4,6-trimethylbenzoylphosphinate (LAP), trimethylbenzoyl based photoinitiators, diphenyl(2,4,6-trimethylbenzoyl)phosphine oxide (TPO nanoparticle) Irgacure class of photoinitiators, ruthenium, and riboflavin, or mixtures thereof.

In some embodiments, the scaffolds or compositions further include one or more additive UV visible dyes, for example, UV381A, UV381B, UV382A, or UV386A. The three digit number indicates wavelength which visualizes the dye. The photoactive dye may be a UV dye with absorbance spectra between 300 nm to 420 nm. The photoactive dye may have a wavelength range of 300 nm to 400 nm. The photoactive dye may be non-cytotoxic. The photoactive dye may include a benzyne ring in the molecular structure. The photoactive dye may be quinolone yellow, a UV dye, or a dye with a molecular structure similar thereto. The photoactive dye may be UV 386A dye.

In some embodiments, the scaffold or composition further comprises an additive immunosuppressant drug or biologic, for example, Prednisone, Tacrolimus (Prograf), Cyclosporine (Neoral), Mycophenolate Mofetil (CellCept), Imuran (Azathioprine), or Rapamune (Rapamycin, Sirolimus).

In some embodiments, any one or more of the aforementioned additional polymerized moieties or additives may be present, independently in each instance, at about 0% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 100%, by weight, based on the total weight of the scaffold, composition, or printed object.

In some embodiments, the composition or scaffold further comprises cells, which may be adhered to the scaffold. The cells may be selected from fibroblasts, endothelial cells, epithelial cells, and mixtures thereof. In some embodiments, the scaffold is a 3D-printed scaffold. In some embodiments, the polymeric scaffold is in the shape, substantially, of a disk, sphere, cylinder, prism, cube, rectangular prism, pyramid, tetrahedron, or cone. In some embodiments, the polymeric scaffold is substantially the same shape, size, and/or has the same relative dimensions of an organ or a fragment of an organ, for example, kidney, heart, liver, lung, spleen, brain, vessel, gallbladder, stomach, pancreas, bladder, skeletal bone, cartilage, skin, hair follicle, intestine, a muscle, larynx, or pharynx.

Methods

In one aspect, a method of modifying a polymeric scaffold disclosed herein in provided. The method may comprise contacting the scaffold with a hydrolysis agent or a proteolysis agent. In some embodiments, the modification of the scaffold increases affinity of the scaffold for cells.

In another aspect, a method of a method of increasing actin coverage of cells is provided. The method comprising contacting the cells with the polymeric scaffold disclosed herein. The cells may be selected from fibroblasts, endothelial cells, epithelial cells, and mixtures thereof.

The hydrolysis agent may be selected from a hydroxide or a hydroxide source (e.g., LiOH, NaOH, $Be(OH)_2$, $Mg(OH)_2$, KOH, $B(OH)_3$, $Fe(OH)_2$, $NH_4OH$, or $Al(OH)_3$). In some embodiments, the concentration of the hydrolysis agent in a solution thereof contacted to the scaffold, is about 1 mM to about 25 mM, about 25 mM to about 50 mM, about 50 mM to about 100 mM, about 100 mM to about 150 mM, about 150 mM to about 300 mM, about 300 mM to about 500 mM, about 500 mM to about 1 M, about 1 M to about 5 M, or about greater than 5 M.

In some embodiments, the hydrolysis agent may comprise a catalytic or metal additive. In some embodiments, the agent may comprise a complex or compound comprising Ce(IV), Co(II), Co(III), Cu(II), Fe(III), Ln(III), Ni(II), Mo(IV), Pd(II), Zn(II), Zr(IV), Eu(III), Hf(IV), Ce(III), Eu(III), La(III), Tb(III), Y(III) Lu(III), Tb(III), Tm(III), Yb(III), cerium(IV), $K_4Zn_4[Fe(CN)_6]_3 \cdot H_2O$, NiMo/γ-$Al_2O_3$, $Ni(NO_3)_2 \cdot 6H_2O$, $(NH_4)_6Mo_7O_{24} \cdot 7H_2O$, Y(III) in PI liposomes, and La(III) in PI-laden erythrocyte membranes.

The proteolysis agent may comprise an esterase, for example cholesterol esterase. In some embodiments, the agent comprises a hydrolase, collagenase, stromelysin, proteinase K, a peptidase (i.e., exopeptidases, endopeptidases, aminopeptidases, dipeptidases, carboxypeptidases, peptidyl dipeptidases, endopeptidases), a protease (i.e., aspartic proteases [i.e., pepsin and capthepsin D], cysteine proteases [i.e., Bromelain, Papain, ficain, rhinovirus 3C, TEV protease, and TVMVprotease], glutamic proteases, metalloproteases [i.e., Endoproteinase, asp-n, thermolysin, collagenase, and dipase], asparagine proteases, and serine proteases [i.e., Trypsin, chymotrypsin, enterokinase, WNV protease, Endoproteinase, Elastase, Subtilisin, Proteinase K, Thrombin, and Factor Xa) threonine proteases, proteinases, or gelatinase. In some embodiments, the proteolysis agent comprises an active esterase hydrolase, collagenase, stromelysin, or gelatinase fragment; an esterase hydrolase, collagenase, stromelysin, or gelatinase derivative; or a functional equivalent of the esterase hydrolase, collagenase, stromelysin, or gelatinase. In some embodiments, the proteolysis agent is in a solution contacted with the scaffold and the concentration of the proteolysis agent in the solution is about 0.1 U to about 1 U, about 1 U to about 2.5 U, about 2.5 U to about 5 U, about 5 U to about 7.5 U, about 7.5 U to about 10 U, about 10 U to about 15 U, or about greater than 15 U, wherein U is U/mL.

In some embodiments, the contacting is for about 1 hr to about 2.5 hr, about 2.5 hr to about 5 hr, about 5 hr to about 7.5 hr, about 7.5 hr to about 10 hr, about 10 hr to about 24 hr, about 24 hr to about 2 days, about 2 days to about 4 days, about 4 days to about 8 days, about 8 days to about 12 days, about 12 days to about 30 days, or greater than about 30 days.

Definitions

The term "poly(ethyelene glycol) (meth)acrylate/(meth) acrylamide" as used herein refers to a moiety comprising a poly(ethyelene glycol) (PEG) moiety substituted at one end of the PEG moiety with (meth)acrylate and at the other end with (meth)acrylamide. For example a compound of the formula:

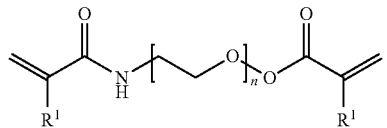

wherein each $R^1$ is independently H or $CH_3$.

The term "polymerized collagen-methacrylamide," or "ColMA" as used herein, refers to polymerized collagen protein wherein amines of the protein have been substituted with acryl groups to have an acrylamide moiety. For example, the lysine and hydroxylysine residues of collagen may have amine groups thereof reacted with (meth)acrylic anhydride to produce (meth)acrylamide moieties on the collagen.

"Hydroxypropyl acrylate" (HPA), as used herein, may refer to 1-hydroxy propyl acrylate, 2-hydroxypropyl acrylate, or 3-hydroxypropyl acrylate. When HPA is polymerized it may refer to a polymer comprising mixtures of any of the aforementioned hydroxypropyl acrylates.

"LAP," as used herein refers to lithium phenyl-2,4,6-trimethylbenzoylphosphinate, the photoinitiator which allows the bioink to polymerize during 3D printing.

"Degree of functionalization," as used herein in references to (meth)acrylated collagen (ColMA)

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively. The term "or" is inclusive unless modified, for example, by "either." Thus, unless context or an express statement indicates otherwise, the word "or" means any one member of a particular list and also includes any combination of members of that list. Other than in the examples, or where otherwise indicated, all numbers expressing quantities of ingredients or reaction conditions used herein should be understood as modified in all instances by the term "about."

The term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about." The term "about" is used herein to provide literal support for the exact number that it precedes, as well9 as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only and is not intended to limit the scope of the present invention, which is defined solely by the claims. In order that the present disclosure can be more readily understood, certain terms are first defined. Additional definitions, all numerical designations, e.g., pH, percentages, temperature, time, concentration, and molecular weight, including ranges, are approximations which are varied (+) or (−) by increments of 1, 5, or 10%. It is to be understood, although not always explicitly stated that all numerical designations are preceded by the term "about." It also is to be understood, although not always explicitly stated, that the reagents described herein are merely exemplary and that equivalents of such are known in the art and are set forth throughout the detailed description.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the disclosure.

As used herein, the term "treatment" or "treating" means treatment of a scaffold, ink, printed object, or composition with, an agent that alters its physical or biological properties, for example, a hydrolysis agent such as NaOH or a proteolysis agent.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention. When an embodiment is defined by one of these terms (e.g., "comprising") it should be understood that this disclosure also includes alternative embodiments, such as "consisting essentially of" and "consisting of" for said embodiment.

"Substantially" or "essentially" means nearly totally or completely, for instance, 95%, 96%, 97%, 98%, 99%, or greater of some given quantity.

Embodiments described herein are further illustrated by, though in no way limited to, the following working examples.

EXAMPLES

Example 1: Biological and Mechanical Assessment of Post Processed Scaffolds Using Accelerated Hydrolysis and Proteolysis The composition of the formulation tested in the present example was Ink A. The formulations for Inks A-D are as shown below:
Ink A: ColMA (degree of functionalization 100), PEGDA3400, PEGDA 575.
Ink B: PEGDA3400, PEGDA 575.
Ink C: ColMA (degree of functionalization 50), PEGDA3400, PEGDA 575
Ink D: ColMA (degree of functionalization 30), PEGDA3400, HPA.

Procedure:
1. 24 disks were printed using above condition and stored in DPBS−/− overnight at 37° C.
2. Prospect samples were incubated to proper solution in the rocker and stored at 37° C. in TC room DELI incubator for 8 hours
   a. Solution Ratio
      I. 2.5 mL of solution per disk (0.0142 mL/mm$^2$)
      II. 5 mL of solution per dog bone
   b. Rotational Rocker
      I. Speed=45 rpm
      II. Rotation=90°
3. After incubation, remove the samples and place into a 24 well plate with DPBS−/−.
4. Samples are washed with DPBS−− three times (10 min) at RT and stored in 5X P/S (in PBS) solution for 1 hour.
5. The samples were transferred to 24 well plate for cell seeding.
6. Follow attached protocol for cell seeding, fixing and staining and Follow attached protocols for image acquisition using confocal microscopy.
7. Repeat same procedure for 72 hour samples Testing Procedure:
1. 24 discs and 12 dog bones were printed using above condition and stored in DPBS−/− at room temperature overnight
2. Weight the discs. If there is leftover resin in the discs, blot with a kimwipe prior to weighing
3. Prospect samples were incubated to proper solution in the rocker and stored at 37° C. in TC room DELI incubator for 8 hours
   a. Solution Ratio
      I. 2.5 mL of solution per disk (0.0142 mL/mm$^2$)
      II. 5 mL of solution per dog bone
   b. Rotational Rocker
      I. Speed=45 rpm
      II. Rotation=90°
4. After incubation, remove the disks and place into a 24 well plate with DPBS−/− and remove the dog bones and place in petri dishes. Ensure that the disks and dog bones is completely covered with DPBS−/−
5. Weight the discs. If there is leftover resin in the discs, blot with a kimwipe prior to weighing 6. Test the compressive assessment of the disk using the DMA850 (Waters, TA Instruments, New Castle, DE) mechanical analyzer.

7. Test the tensile assessment of the dog bone using the tensile test protocol listed below was used.

DMA850 Protocol

Preparing the molds: All the samples for compression and tensile test were casted into the PDMS molds. The laser cut machine was used to cut the negative mold in desired size and geometry. The polycarbonate negative molds were placed at the bottom petri dishes and the PDMS solution made of resin and hardener with ratio of 1:10 (W/W %) was poured into the petri dishes. The petri dishes were kept in desiccator for 1 hr for degassing the PDMS. Then, the petri dishes are moved to oven for curing the PDMS for 1 hr at 80° C.

Preparing the samples: The formulation solutions must be gently added to each PDMS reservoir using 1000 μl pipette. The volume of each reservoir for compression samples and tensile samples are 260 μl and 240 μl. Place the PDMS molds in the center of UV-crosslinker at wavelength of 365 nm for 2 min to cure the samples.

Curing: Place the PDMS molds in the center of UV-crosslinker at wavelength of 365 nm for 2 min to cure the samples.

Tensile Test Protocol (Tensile Test)

Figure 48:
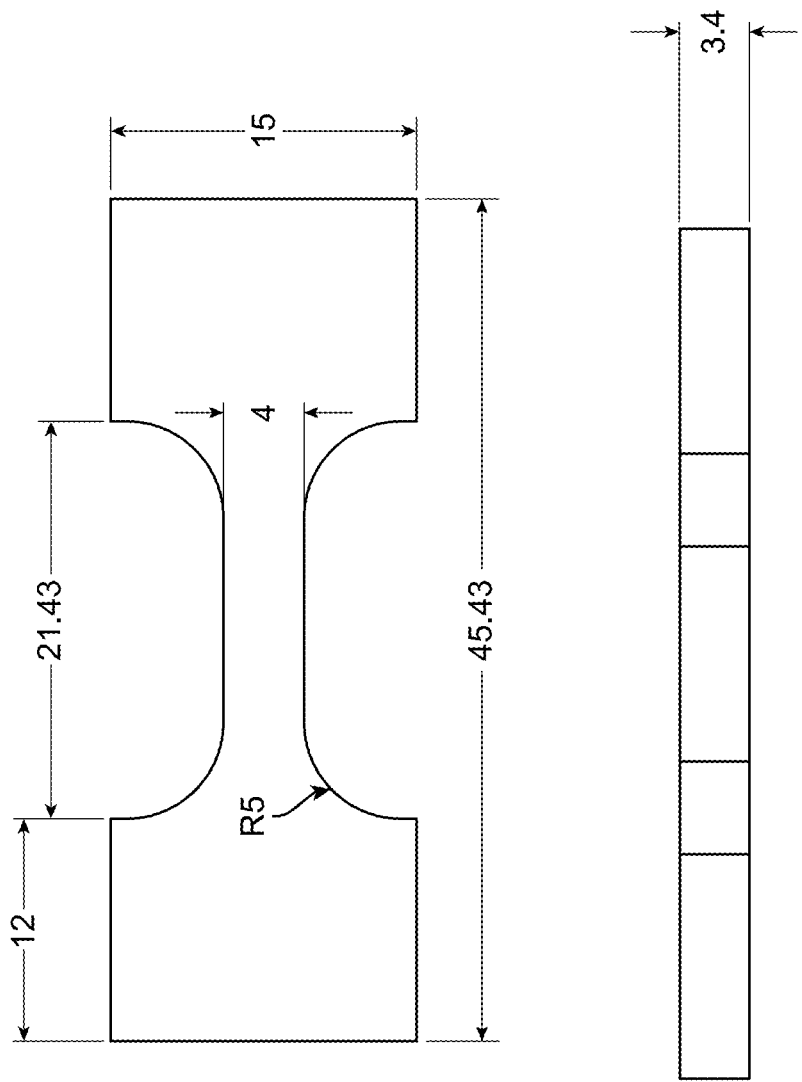
FIG. 48 shows a dogbone sample for tensile testing according to the examples.

Specimen is cut in dog bone geometry as shown in FIG. 48 and tested according to ASTM D1708-13; Standard Test Method for Tensile Properties of Plastics by Use of Microtensile Specimens. Specimens must be rinsed in DPBS (no Mg, no Ca):

Option 1: Minimum of 2 hours at 37° C.
Option 2: Overnight soak is preferred. 37° C.

Figures 49A, 49B:
FIGS. 49A-49B show dogbone sample in tensile strength test.

A very small portion of the tab should be visible from each of the grips as shown in FIG. 49A. If the sample is slightly bowed, this is most likely due to a portion of the material being squeezed out of the grips. As the sample extends to the pre-load the slack will be removed. Minimal bowing is preferred but may not be totally avoided as the grips must be tight enough to prevent the sample from slipping out. One should then zero the displacement. Leave the residual force—this is an actual force either pushing or pulling on the specimen Specimen should be extended until the programmed pre-load is achieved. Once this load is reached, the strain value will be auto-balanced and data will be plotted on a graph. Acceptable Failure mode—specimen must fail in the neck region, not at the grip interface as shown in FIG. 49B.

Results: For mechanical assessment, both the 5 U/mL cholesterol esterase and 50 mM NaOH had decreased in Young's modulus and ultimate stress for DMA compression testing. Since the dog bone broke above the porous region, the ultimate tensile stress and strain can not be suggested. There was no significant difference for the Young's modulus for all groups for tensile testing.

For the biological assessment, the 50 mM NaOH treatment groups is not significantly different from the glass control for all variables at Day 4. The 5 U/mL cholesterol esterase is not significantly difference from the PBS control for all variables at Day 4.

There is no difference in the cell spread because the 50 mM NaOH and glass control both created a dense network with overlapping actin fibers. There is high variability between samples treated with 50 mM NaOH at Day 4. This is suggested that the cells peeled off resulting in the minimal cell attachment.

Example 2: Biological and Mechanical Assessment by Post Processing Treatments on Ink C and Ink A The objective of this example is to evaluate the biological and mechanical properties of Ink C under accelerated hydrolysis using alkaline conditions and compare to Ink A as described in Example 1.

Three testing conditions were used:
Ctrl (DPBS−/−)
100 mM NaOH (in D.I. $H_2O$)
Glass cover slips (positive control)

Procedure:
1. 16 disks per bioink were printed using above condition and washed 3× in DPBS−/−
2. Prospect samples were incubated to proper solution in the rocker and stored at 37° C. in TC room DELI incubator for 4 hours
  a. Solution Ratio
    I. 2.5 mL of solution per disk (0.0142 mL/mm$^2$)
  b. Rotational Rocker
    I. Speed=45
    II. Rotation=90
3. After incubation, remove the samples and place into a 24 well plate or petri dish with DPBS−/−. Ensure that the hydrogel is completely covered with DPBS−/−
4. Samples will be washed with DPBS−− three times (10 min) at RT and store in 5× P/S (in PBS) solution for 1 hour
5. Transfer the allocated samples to 24 well plate for cell seeding. Ensure the hydrogel have the base layer facing down within the well plate for proper cell seeding
6. Cell seed, fix and stain
  a. Need to decrease seeding density to 10,000 cells/well
  b. The staining solution for the 3D printed disks needs to be increased to 1 mL due to swelling
  c. Add 1 mL/well of cell suspension solution to 24 well-plate discs
7. Acquire images as in Example 1

Mechanical Assessment Procedure:
Two Testing Conditions:
Ctrl (DPBS−/−)
100 mM NaOH (in D.I. $H_2O$)

Procedure:
1. 12 dog bones per bioink were printed using above condition and stored in DPBS−/− at room temperature overnight
2. Prospect samples were incubated to proper solution in the rocker and stored at 37° C. in TC room DELI incubator for 4 hours
  a. Solution Ratio
    I. 18.725 mL of solution per dog bone (0.0142 mL/mm$^2$)
  b. Rotational Rocker
    I. Speed=45
    II. Rotation=90
3. After incubation, remove the dog bones and place into a petri dish with DPBS−/−s. Ensure that the dog bones are completely
4. Test the tensile assessment of the dog bone using the tensile test protocol described above.

Swelling Ratio
Two Testing Conditions:
Ctrl (DPBS−/−)
100 mM NaOH (in D.I. $H_2O$)

Procedure:
1. 8 disks per bioink were printed using above condition and washed 3× in DPBS−/−

2. Prospect samples were incubated to proper solution in the rocker and stored at 37° C. in TC room DELI incubator for 4 hours
 a. Solution Ratio
  I. 2.5 mL of solution per disk (0.0142 mL/mm$^2$)
 b. Rotational Rocker
  I. Speed=45
  II. Rotation=90
3. Weigh the disk. Blot dry if necessary to remove excess liquid
4. Place sample into a 24 well plate with DPBS-/-. Ensure that the hydrogel is completely covered with DPBS-/-
5. Store plate at 37° C. for 24 hours
6. Weigh the disk. Blot dry if necessary to remove excess liquid
7. If swelling had not stabilized after 24 hours, continue taking weights at more time points Results: The treatment increased the cell attachment and decreased the mechanical properties of Ink C. These are the similar results demonstrated in Ink A. The mechanical properties were so significant decreased that it results in compromised mechanical integrity of Ink C.

Example 3: PAECs and SAECs Biological Assessment of Ink A Undergoing Accelerated Hydrolysis The objective of this study was to evaluate the biocompatibility of PAEC and SAEC with Ink A that have undergone accelerated hydrolysis by sodium hydroxide and cholesterol esterase Biological Assessment
Five Testing Conditions:
Ink A PBS
Ink A 0.1M NaOH
Ink A 5 U/mL Cholesterol Esterase
Procedure:
1. 48 discs were printed using above condition and washed 3× in DPBS-/-
2. Prospect samples were incubated to proper solution in the rocker and stored at 37° C. in TC room DELI incubator
 a. Incubation Time
  I. 4 hours=PBS, 0.1M NaOH
  II. 6 hours=Cholesterol Esterase
 b. Solution Ratio
  I. 2.0 mL of solution per disk (0.0114 mL/mm$^2$)
 c. Rotational Rocker
  I. Speed=45
  II. Rotation=90
3. After incubation, remove the samples and place into a 24 well plate or petri dish
4. Samples will be washed with DPBS-- three times at RT and store in 5×P/S (in PBS) solution overnight at 37 C
5. Follow protocol below for cell seeding, fixing and staining.
 a. Need seeding density to 20,000 cells/well for PAECs and 40,000 cells/well for SAECs
 b. Add 1 mL/well of cell suspension solution to 24 well-plate discs to thawed cryopreserved samples.
6. Acquire images as in Example 1.
7. Repeat same procedure for 7D samples
Seeding, Fixing, Staining Protocol

| Abbreviations used: | meaning |
|---|---|
| LFN | lung fibroblasts, normal |
| DPBS-- | dulbecco's phosphate buffered saline (no Ca$^{2+}$ or Mg$^{2+}$) |
| DPBS++ | dulbecco's phosphate buffered saline (with Ca$^{2+}$ and Mg$^{2+}$) |
| GM | growth media |

Following crosslinking (or PBS wash if no crosslinking required), discs should be transferred to a 50 mL conical (all 8 discs from a single print can go into one dish) for DPBS++ washes. Discs should be washed twice for at least 30 minutes (can be longer than 20 min, but 2 washes are required regardless of wash time) on the rotator at 37° C. at speed 60 rotation 90.

Discs should be placed in 5× Anti-Anti solution (100× Antibiotic Antimycotic diluted in DPBS) overnight on rotator (speed 60 rotation 90) in 37° C. incubator overnight. Swap out 5× Anti-anti for 2 PBS washes (also on rotator—speed 60 rotation 90) for at least 30 minutes each.

Using an optical 96 well plate, fill 3 wells with 200 µL of wash each. Take the average 384 nm absorbance of the washes from those 3 wells using the SpectraMax i3x (or equivalent. If running multiple prints through washes at the same time, multiple washes can be assessed on the same plate. No wash should have a 384 nm absorbance above 0.1. If any batch has a wash with a 384 nm absorbance above 0.1, repeat the washes and re-test.

Seeding LFN onto 3DP discs: Place Trypsin-EDTA, Trypsin Neutralizing Solution, and LFN GM into 37° C. beads bath. While media are warming, prepare control coverslips. Use sterile forceps to transfer 4 glass 18 mm coverslips to a 24-well plate (prepare 1 plate per time point). If also using 'leaching' study controls, place an additional 4 glass coverslips/column for each ink leave lids off of well plates, close bio safety cabinet, and turn on UV light for 15 minutes to ensure coverslips are sterile (the packaging they come in is not technically sterile). Finish washing 3D discs and organize into 48 well plates if not done already. Note 1: Each time point should have an ~ equal mixture of discs from each print iteration to reduce the variability that can come from different printers/wash cycles/etc. Note 2: Organize the samples by fixation day. A minimum of 4 samples/day is recommended.

After second DPBS wash and confirmation that trace dye/PI is not left at an acceptable level, add 500 µL of LFN GM to each well (3D discs as well as glass coverslip controls). For Leaching study controls, use sterile scalpel to cut 2 discs in half to transfer to the wells with glass coverslips. Note: the discs should not be transferred to the wells until the coverslips have been seeded.

Transfer flask(s) of LFN from 37° C. incubator into biosafety cabinet (or pull the required amount of LFN from the cryo tank and thaw in the beads bath).

For flask cells: Aspirate out media with a clean serological aspirator tip, and add enough DPBS-- to wash the bottom of the flask. Aspirate out DPBS, add enough Trypsin-EDT to coat the cells. Cap the flask, place back in the incubator for 2-4 minutes to allow cells to detach. While cells trypsinize bring a 15 mL conical into the hood to transfer cell suspension to, and bring a 1.5 mL sterile microcentrifuge tube for cell counting. Add 10 µL of Trypan blue to microcentrifuge tube Check cell detachment on phase microscope—if cells are detached, bring into the biosafety cabinet to proceed. Add equal volume of trypsin neutralizing solution as trypsin-EDTA to the flask. Use the serological pipet to continue to 'wash' any remaining cells off of the bottom of the flask (5-8 times), transfer to the 15 mL conical.

Cells may be counted here prior to centrifugation; if counting cells prior to centrifuging: pipet cell suspension up and down 5+ more times to ensure cells are evenly distributed if counting cells after centrifuging: after aspirating waste from cell pellet; resuspend cells in ~5 mL of media; pipet vigorously 10-20 times to break up cell pellet before counting.

Transfer 10 µL of cell suspension to 1.5 mL microcentrifuge tube with trypan blue, transfer 10 µL of cells mixture with Trypan blue to each side of a Luna cell counting slide.

For Cryo Cells: Pull required # cells from the cryo tank (assume 60-70% viability to calculate # required vials). Place cryo tubes in beads bath—thaw as quickly as possible—remove as soon as last trace of ice is gone. Add 10 µL of Trypan blue to microcentrifuge tube. Resuspend cryocells in at least an equal volume of media (in a 15 mL conical). After resuspending thawed cells by pipetting up and down 10-20 times; pull 10 µL of cell suspension and add to the microcentrifuge tube with Trypan Blue; transfer 10 µL of cells mixture with Trypan blue to each side of a Luna cell counting slide. Cap the 15 mL centrifuge tube with cell suspension and place in a swinging bucket holder in the centrifuge. Spin for 5 minutes at 150 G.

Count cells using the Luna Slide Counter while cell suspension is in centrifuge (if you prefer to do this after centrifugation that is fine as well). Multiply the viable cell/mL average by the total volume of cell suspension to determine the total cell number: Cells are seeded at 10,500/$cm^2$ for biocompatibility screens; 10,000 cells/well for the discs in the 48 well plate; 20,000 cells/well for the controls in the 24 well plate.

Cells may be resuspended as follows: Resuspend centrifuged cells to a density of $1\times10^6$ cells/mL. Transfer the required amount of cells for the experiment to a new tube, and add media so the cells are suspended at a density of $1\times10^5$ cells/mL. Add 100 µL/well to 48 well-plate discs and 200 µL/well to 24 well-plate controls to give a final seeding of 10,000/well in 48 well plate and 20,000/well in controls (10,500/$cm^2$ in all samples). Ensure cells are added at the top of the wells so they sink down onto the disc or coverslip. Make sure to use the serological pipet to mix the cell suspension regularly to prevent settling during seeding process (once every 15 to 20 samples). Move the well plates back and forth, side to side, and swirl before transferring to the incubator. Refresh media every 2-3 days (500 µL/well)

Fixation and Staining: Prepare a 10% Formalin solution in the chemical fume hood. Prepare 300 µL/well for glass controls and 500 µL/well for 3D discs. Add 0.1% TritonX100 (1:1000) to the 10% Formalin solution. Warm the conical of 10% Formalin and a bottle of DPBS++ in the 37° C. beads bath—warm for 15-20 minutes. Note: DPBS++ helps cell attachment because calcium and magnesium ions are required for cell attachment to a material After fixation components are warmed, perform the DPBS++ wash. Add 300 µL/well of 10% Formalin+0.1% TritonX100 to controls and 500 µL/well to 3D discs. Incubate for 15 minutes at room temperature. Manually aspirate the fixative into a waste container, and wash samples with DPBS-- (3×5 minute washes). After washing, remaining steps can be performed outside of the chemical fume hood.

Prepare the staining solution to be 1:20,000 SytoxOrange; 3:400 Phalloidin 488 200 µL/well for 24 well plate; 500 µL/well for 3d discs. Add staining solution to the wells after $3^{rd}$ DPBS-- wash. Cover samples with aluminum foil to prevent photobleaching during staining; place on rocker at 60 RPM for 45 minutes to 1 hour. After staining, perform 3×5 minute DPBS-- washes. Samples can remain in last wash (continue to protect from light with foil) while being stored at 4° C. prior to image acquisition.

Results: The sodium hydroxide increase the cell attachment of PAEC and SAEC on Ink A. Cholesterol esterase showed no increase in either PAEC or SAEC cell attachment compared to PBS. There was no increase in SAEC cell attachment from day 4 to day 7 for sodium hydroxide, cholesterol esterase, and PBS. There was an increase in PAEC cell attachment from day 4 to day 7 for sodium hydroxide and glass control.

Example 4: Inks Tested for Changes in Mechanical Properties after NaOH or Esterase Treatment and Cell Attachment Properties The following inks were used to create embodiments of the represent disclosure. Each ink also includes a photo initiator, an ultraviolet (UV) absorbing dye, and DI water.

Figures 30A, 30B, 30C:
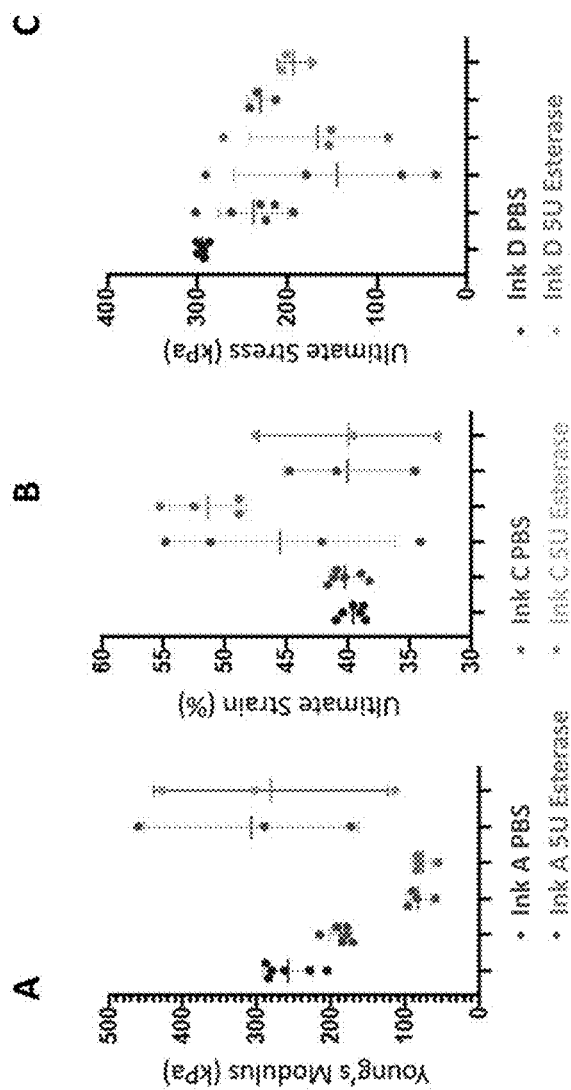
FIGS. 30A-30C shows compressive mechanical properties of a printed object of Ink A, C and D in the examples without exposure to enzymes and with exposure to cholesterol esterase.

FIG. 30 shows compressive mechanical properties of a printed object of Ink A, C and D in the examples without exposure to enzymes and with exposure to cholesterol esterase. FIG. 30A shows Young's modulus, FIG. 30B shows ultimate strain, FIG. 30C shows ultimate stress. Obtained using the DMA850 tensile testing device as described in the Examples.

Figure 31:
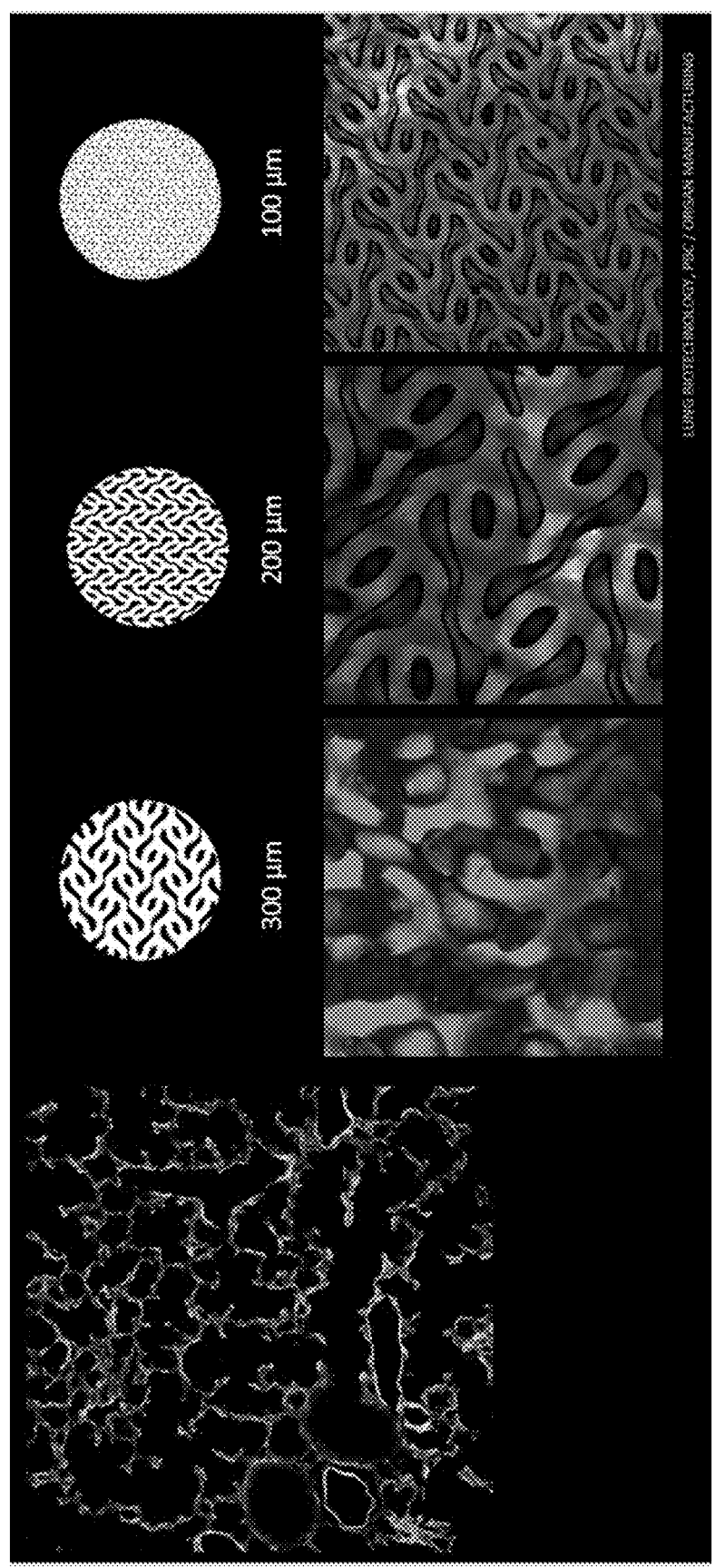
FIG. 31 shows scanning electron microscopy images of the surface network of Fischer discs Ink A with varying channel thicknesses.
Figures 32A, 32B, 32C:
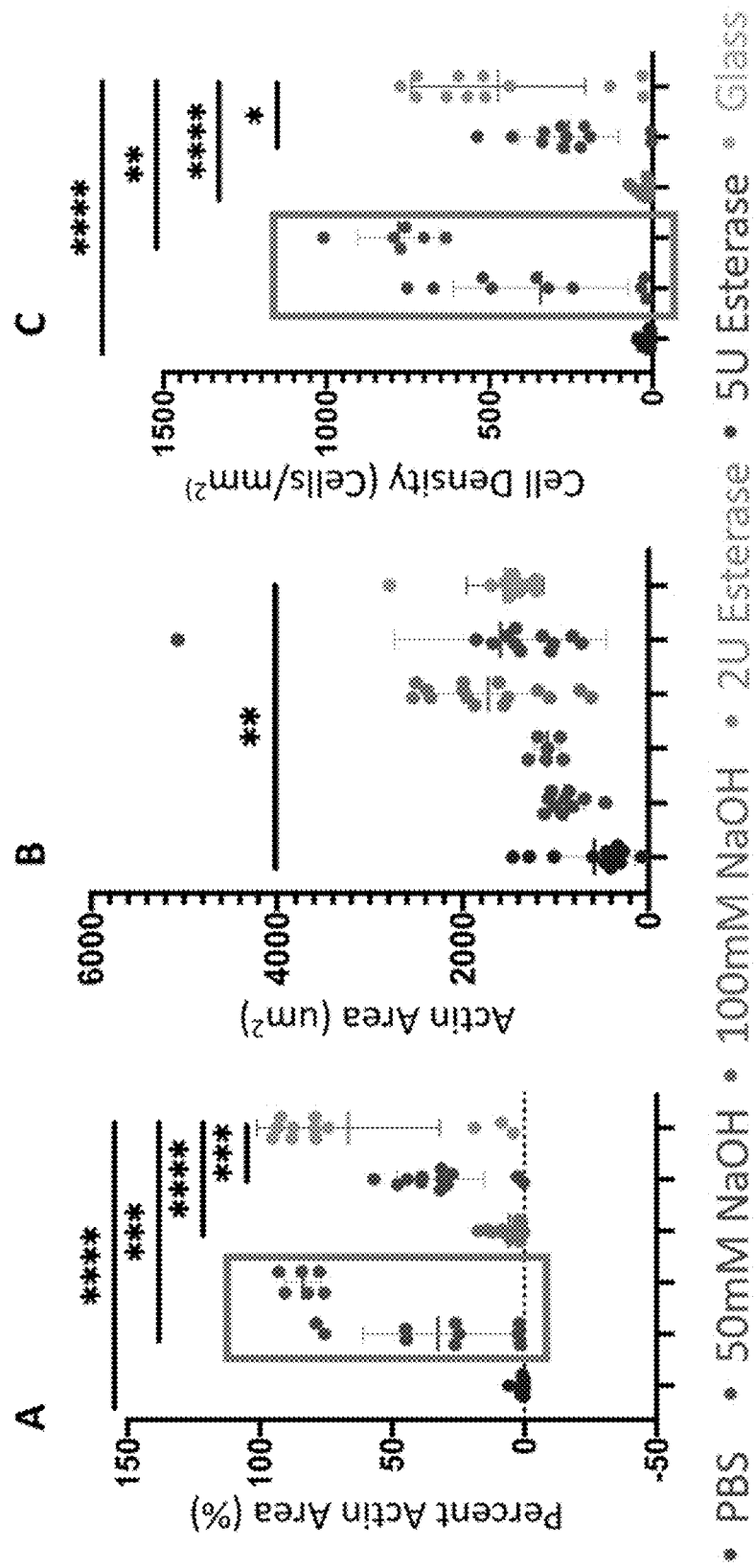
FIGS. 32A-32C show sodium hydroxide increases of human lung fibroblast cell attachment more than cholesterol esterase on Ink A Fischer discs. Cells were seeded according to the same procedure described in Example 2: Procedure, steps 1-7, except that 2 mL of solution per disc was used rather than 2.5 ml/disc.
Figures 33A, 33B, 33C:
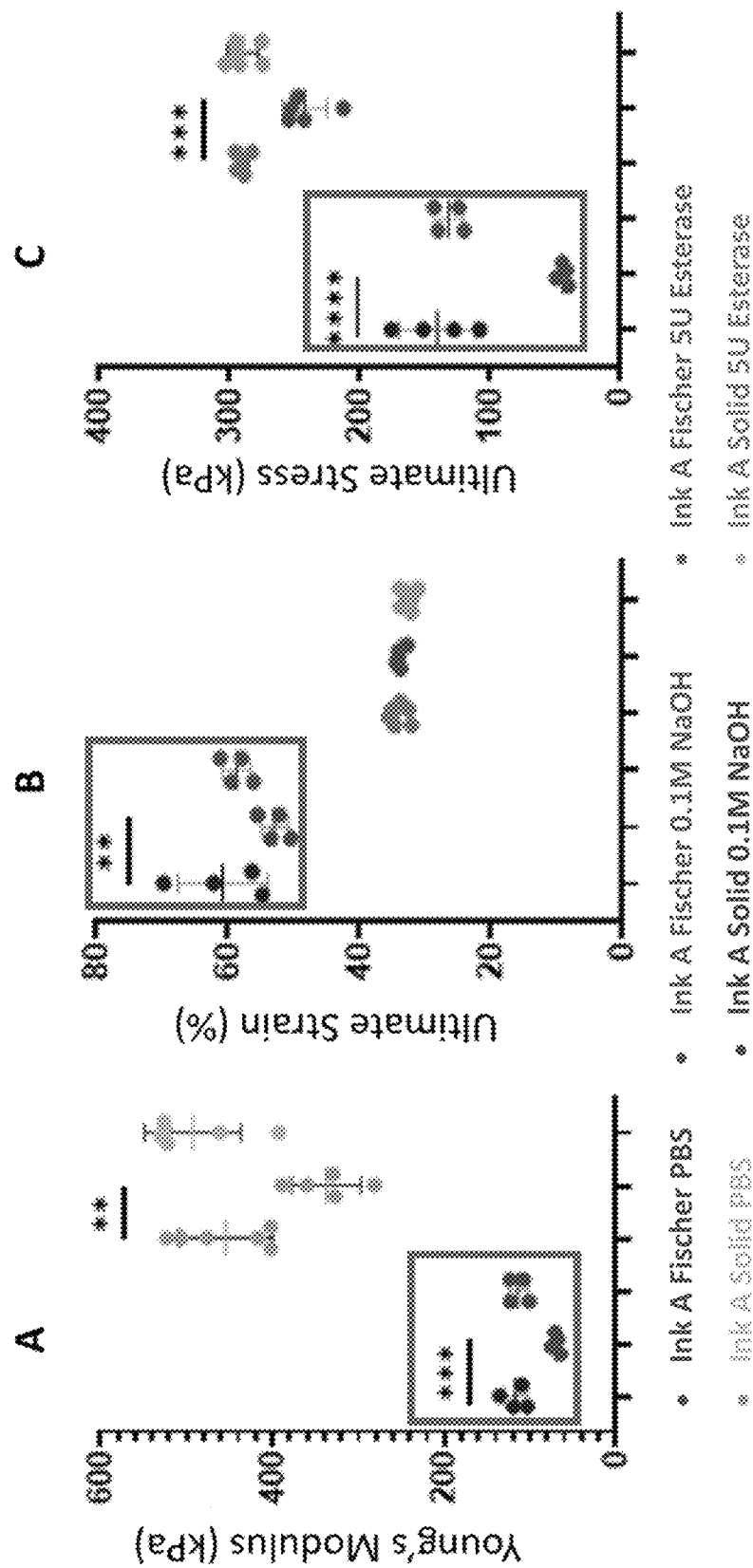
FIGS. 33A-33C shows hydrolysis, through sodium hydroxide or cholesterol esterase, decreases compressive mechanical properties more when there are channels for more crosslinked inks. The properties were tested according to the Mechanical assessment procedure described in Example 2.
Figure 34:
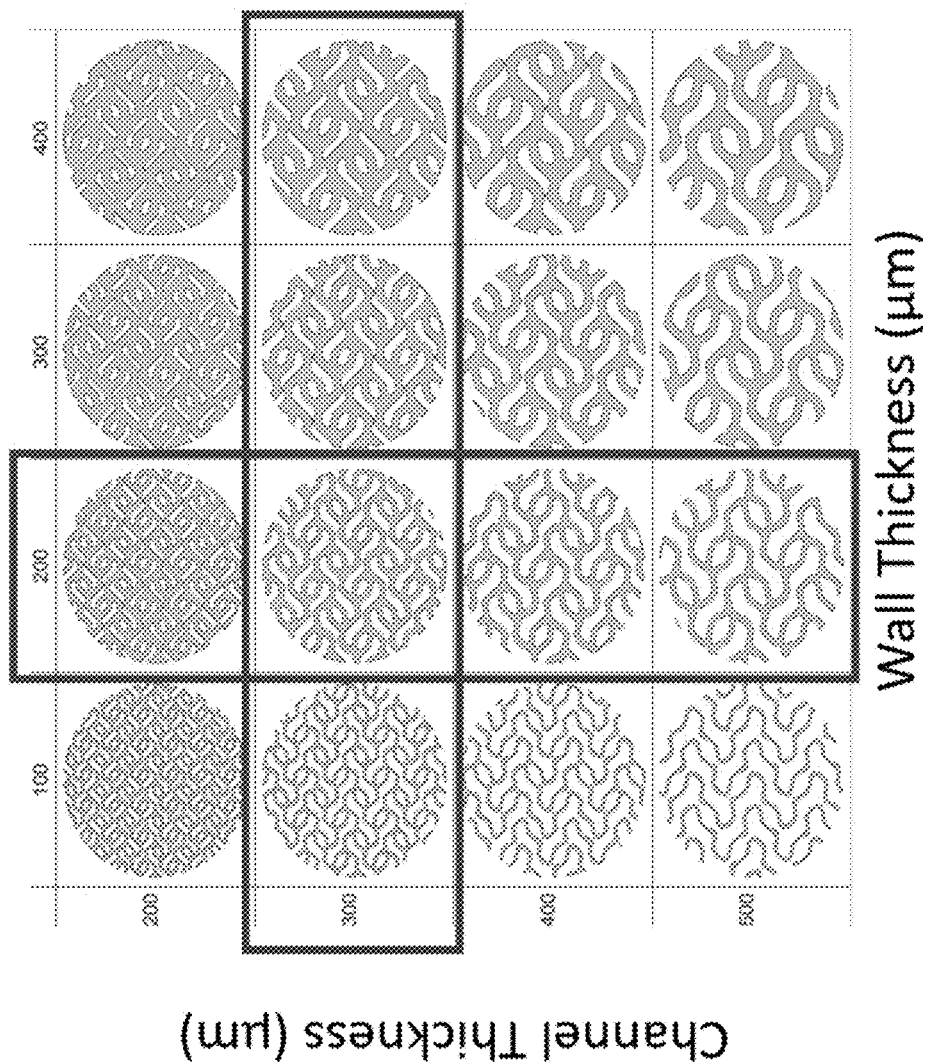
FIG. 34 shows varying wall thickness and channel thickness of Fischer scaffolds. The red boxes indicate the wall and channel thickness of scaffold that are investigated.
Figures 35A, 35B, 35C, 35D:
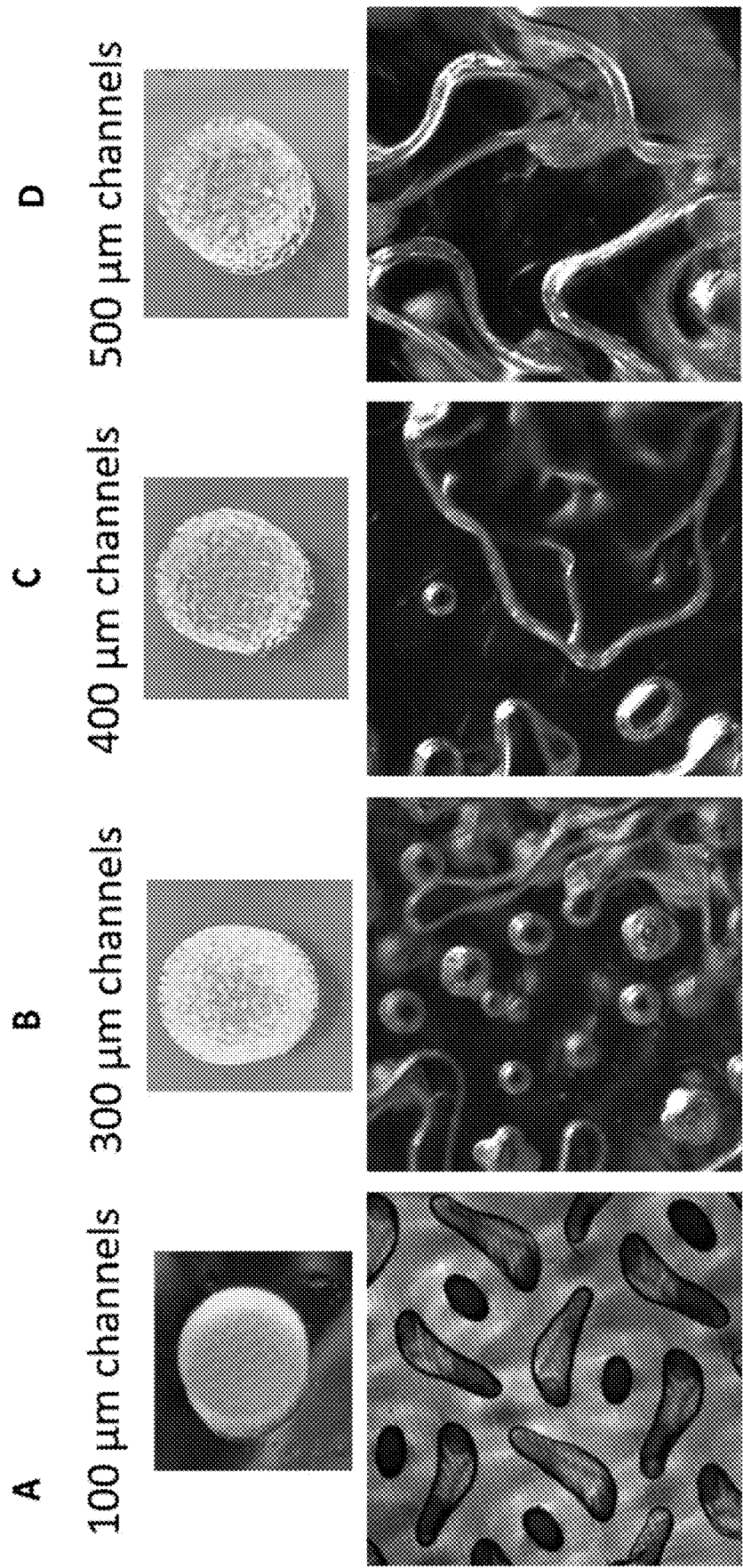
FIGS. 35A-35D show bright field images of Ink A Fischer discs representative of scaffolds of the disclosure having 100 µm (FIG. 35A), 300 µm (FIG. 35B), 400 µm (FIG. 35C), and 500 µm (FIG. 35D) channels. 300 µm channels are required for correct printing with Ink A Fischer discs.
Figures 37A, 37B, 37C:
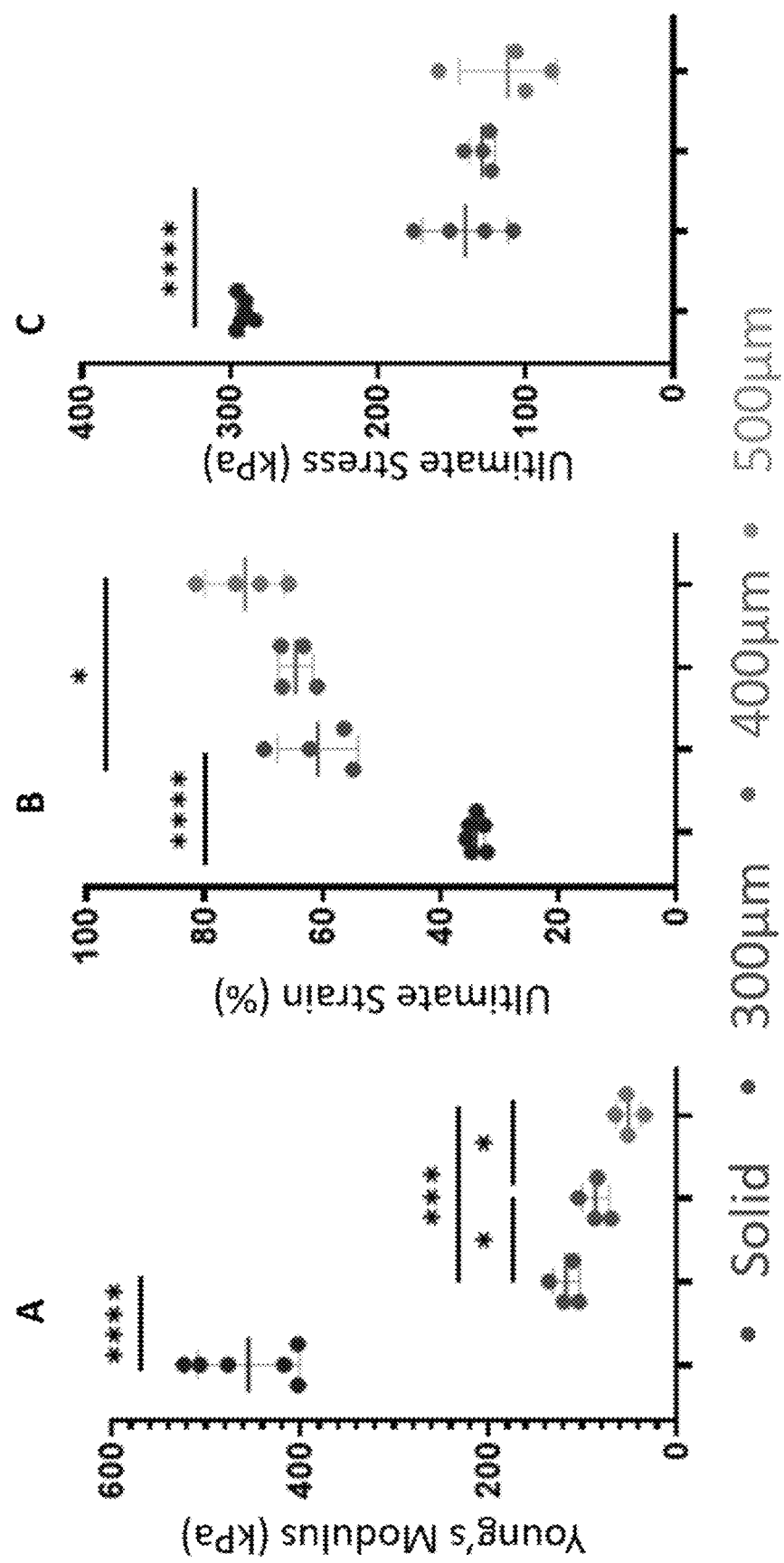
FIGS. 37A-37C show compressive mechanical properties of printed Fischer disc that are solid, 300 µm channels, 400 µm channels, and 500 µm channels.
Figures 38A, 38B, 38C:
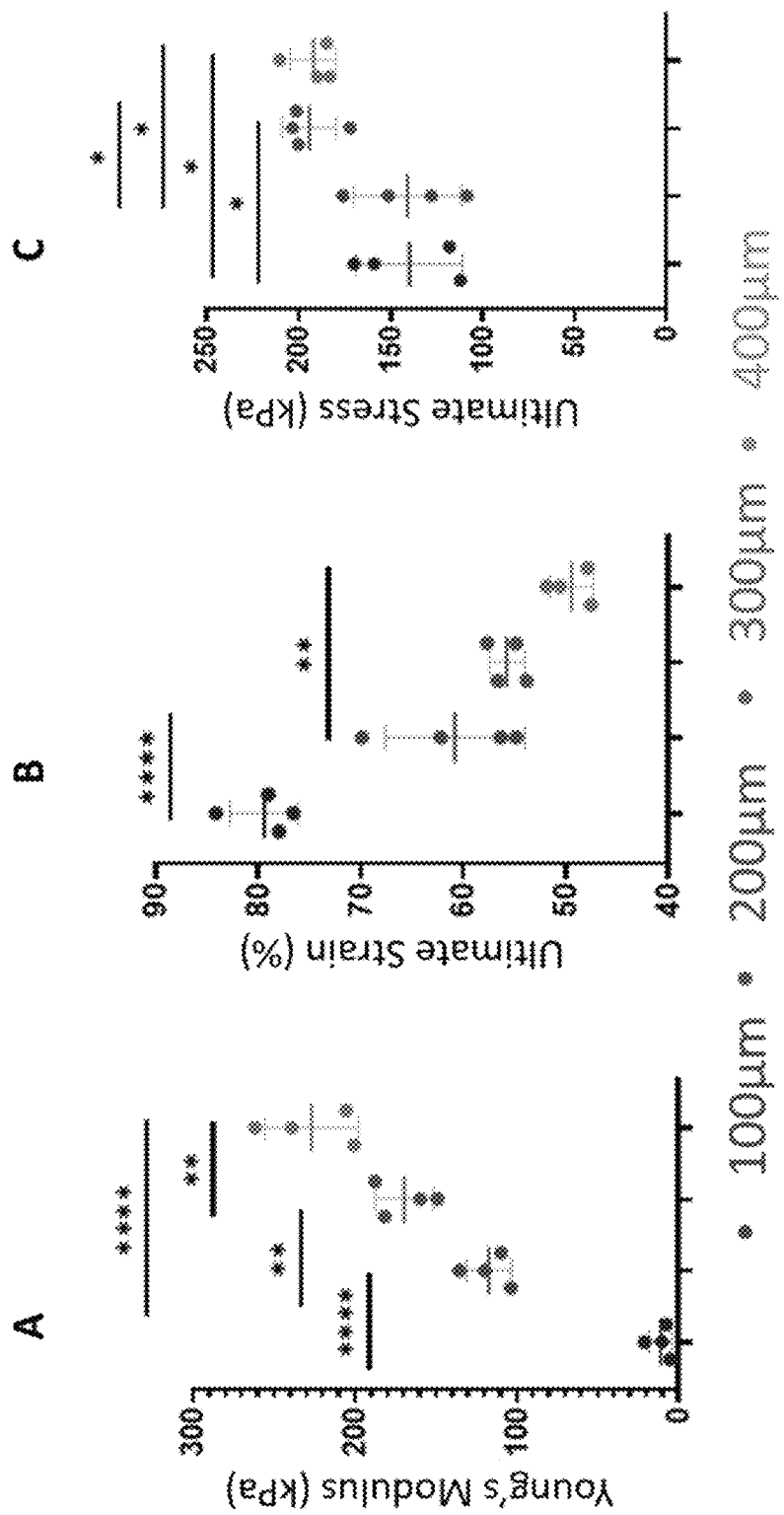
FIGS. 38A-38C show compressive mechanical properties of printer Fischer discs of Ink A with 100 µm, 200 µm, 300 µm, and 400 µm walls.
Figures 39A, 39B:
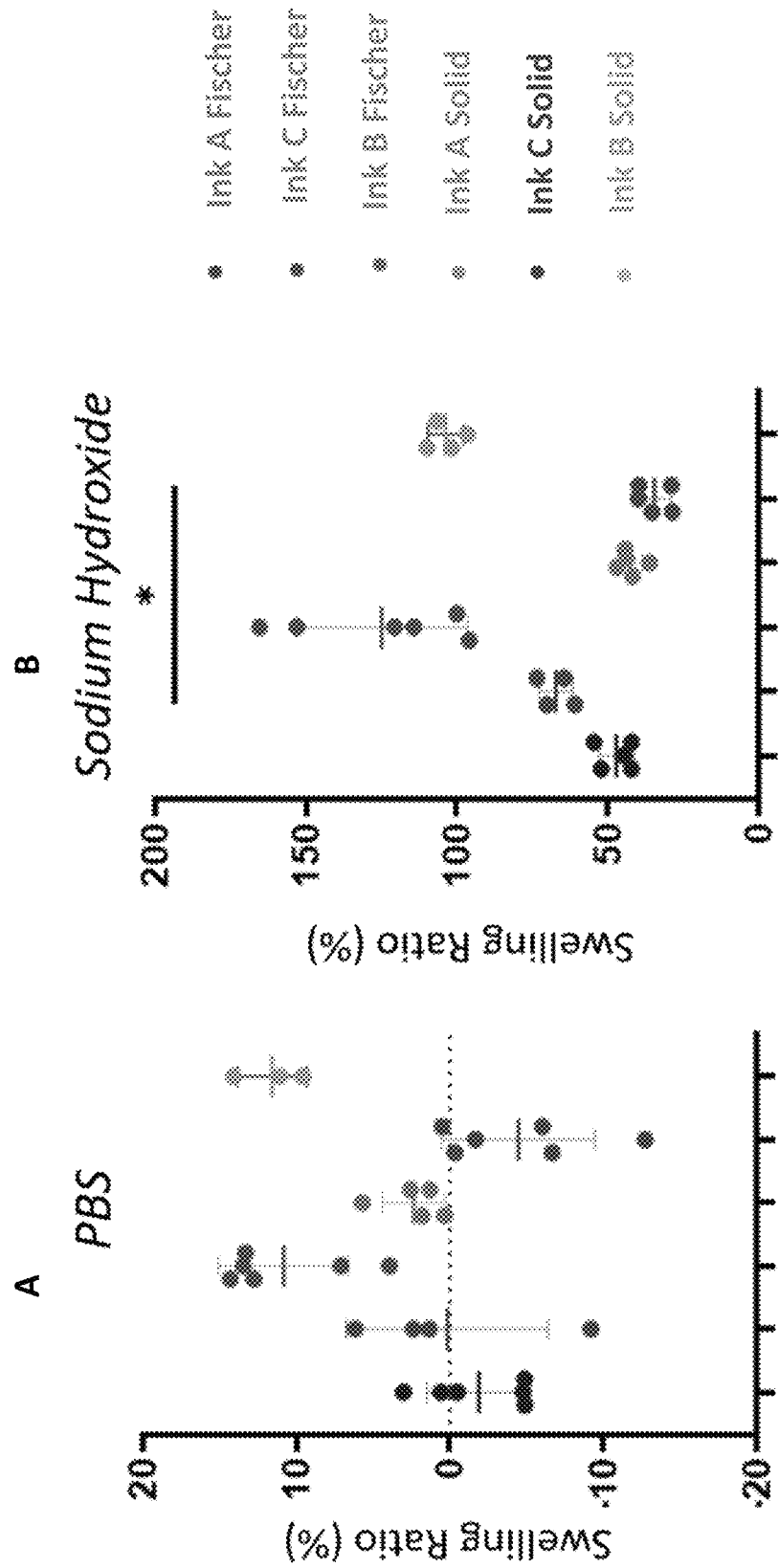
FIGS. 39A-39B show swelling ratio printed discs of multiple ink compositions treated with PBS (FIG. 39A) or NaOH (FIG. 39B).
Figures 40A, 40B, 40C:
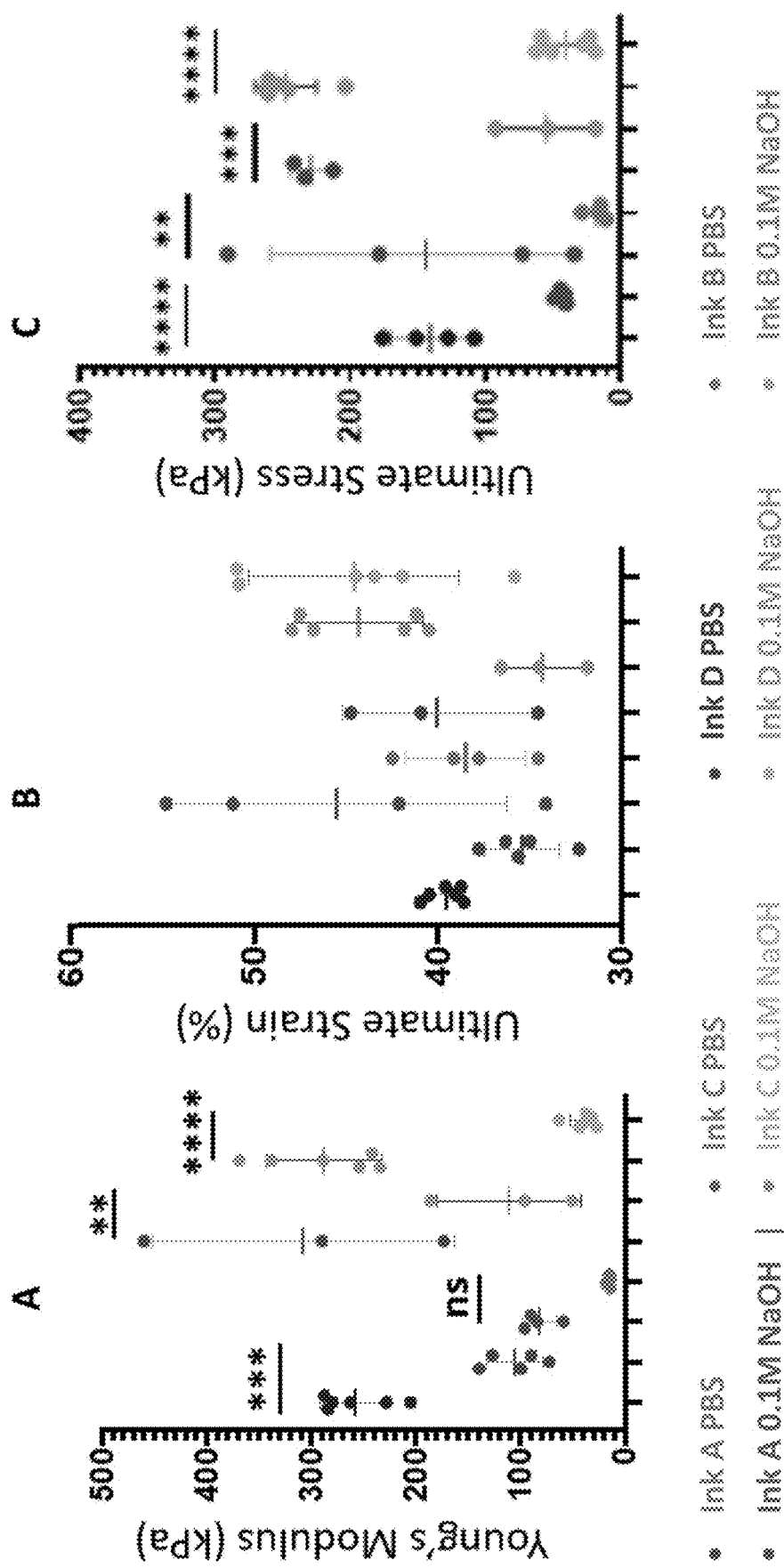
FIGS. 40A-40C show sodium hydroxide decreases compressive mechanical properties of Fischer discs for multiple inks.
Figures 41A, 41B, 41C:
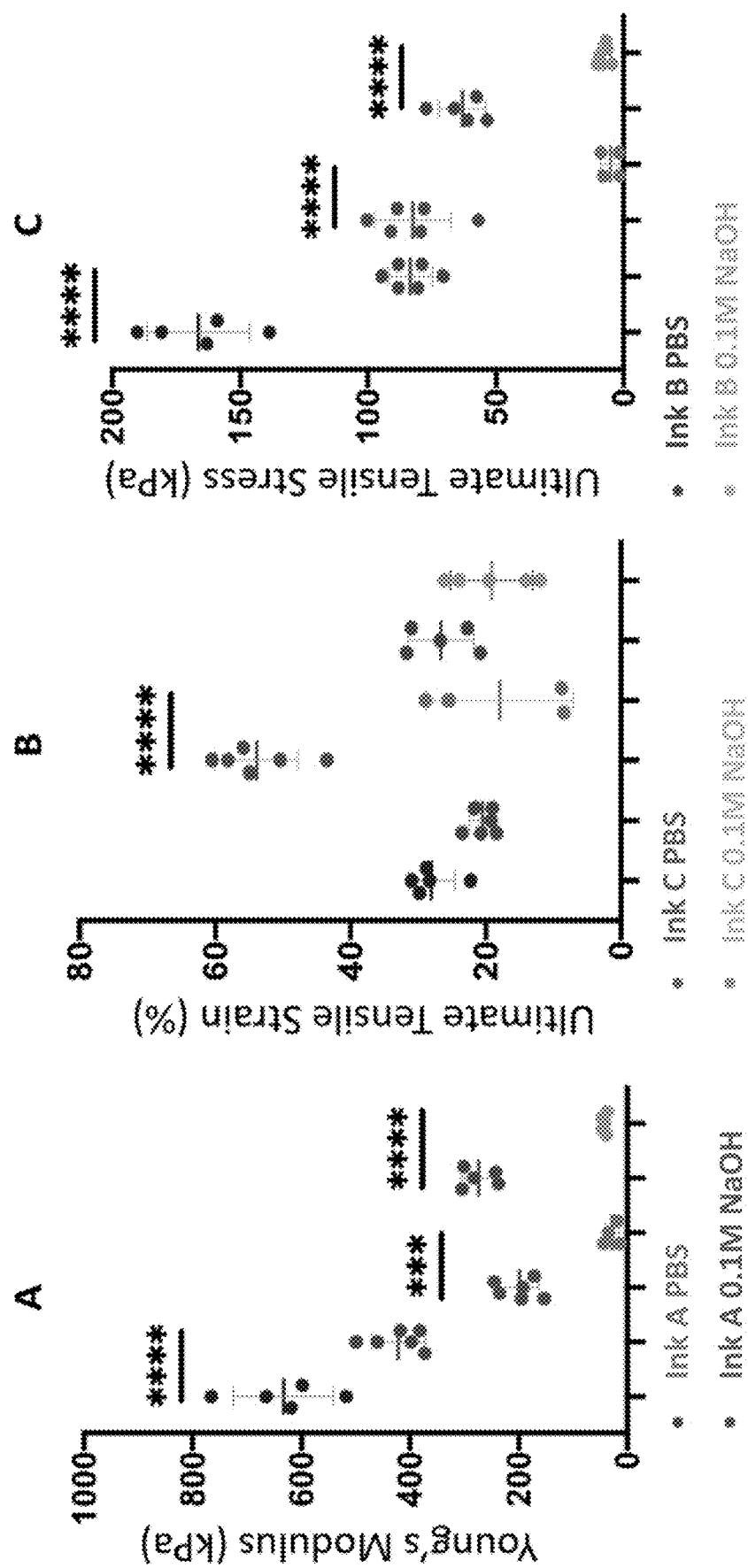
FIGS. 41A-41C show sodium hydroxide decreases tensile mechanical properties of Fischer dog bones for multiple inks.
Figures 42A, 42B, 42C:
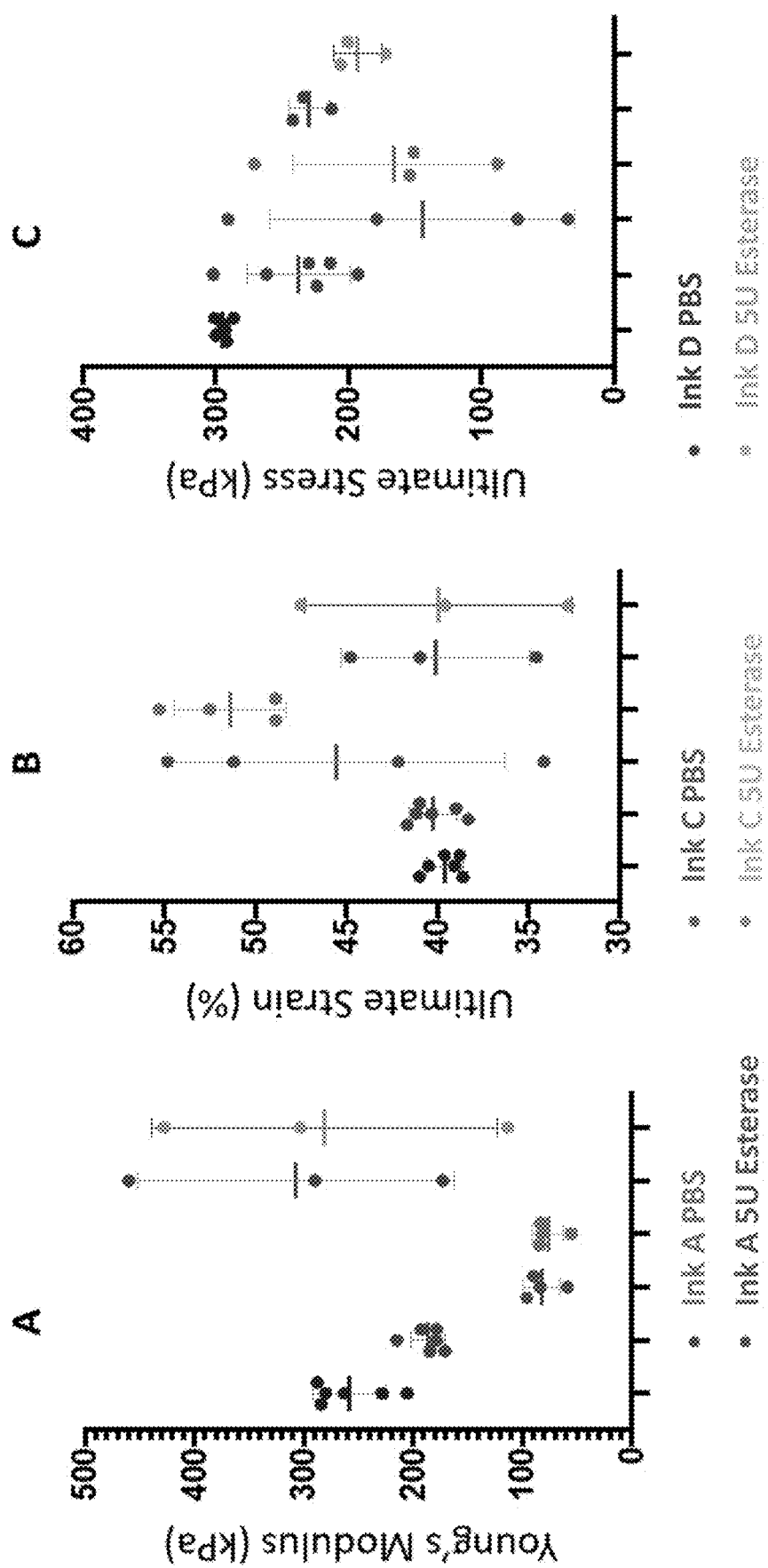
FIGS. 42A-42C show cholesterol esterase decreases compressive mechanical properties of Fischer discs for multiple inks.
Figures 43A, 43B, 43C:
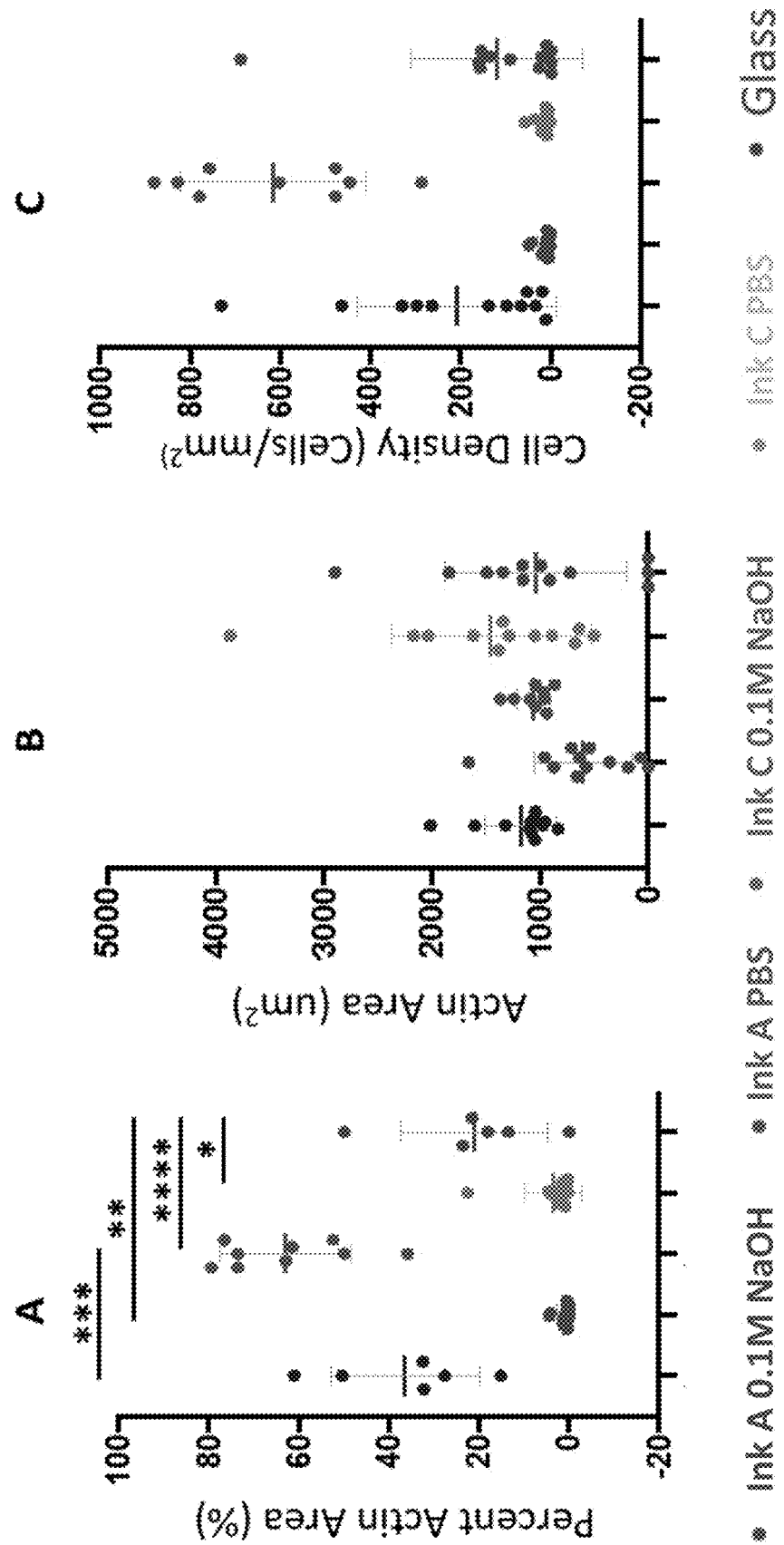
FIGS. 43A-43C show sodium hydroxide increases LFN cell attachment more for less crosslinked inks.
Figures 45A, 45B, 45C, 45D:
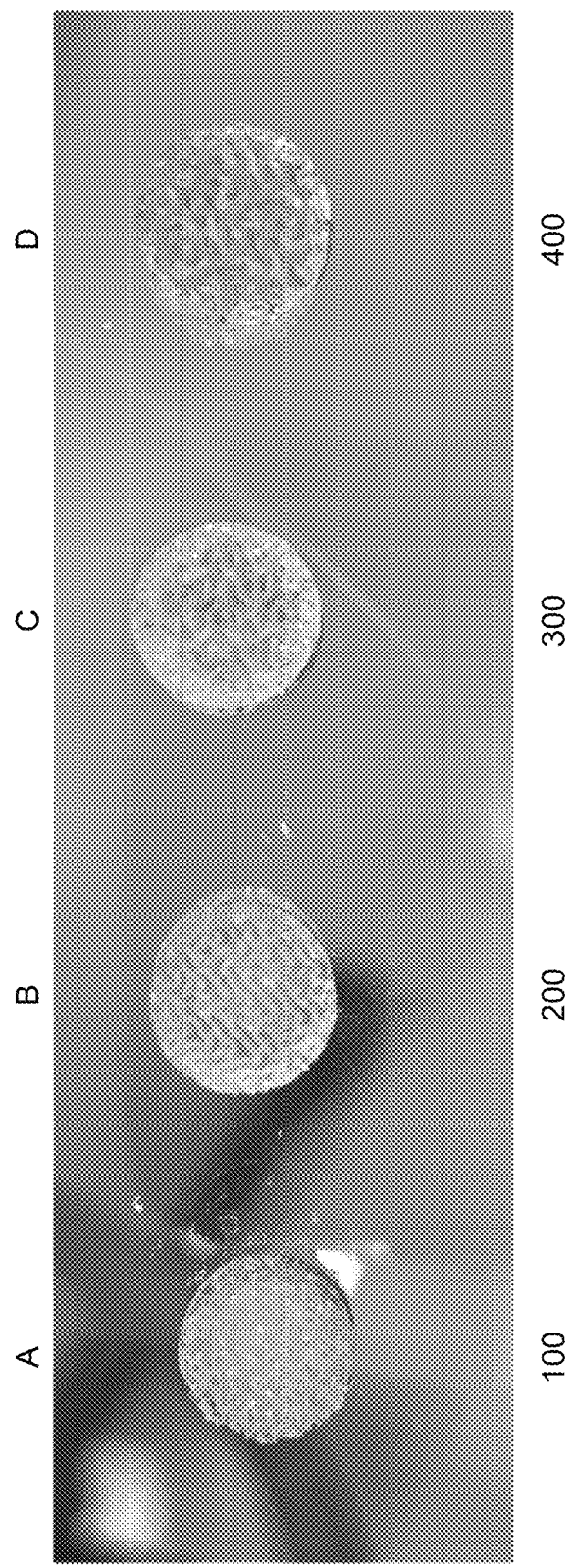
FIGS. 45A-45D show representative images of printed Fischer discs of Ink A with 100 µm walls (FIG. 45A), 200 µm walls (FIG. 45B), 300 µm walls (FIG. 45C), and 400 µm walls (FIG. 45D). 200 µm walls are required for correct printing with Ink A Fischer discs.

FIG. 31 shows scanning electron microscopy images of the surface network of Fischer discs Ink A with varying channel thicknesses.

Figures 46A, 46B, 46C:
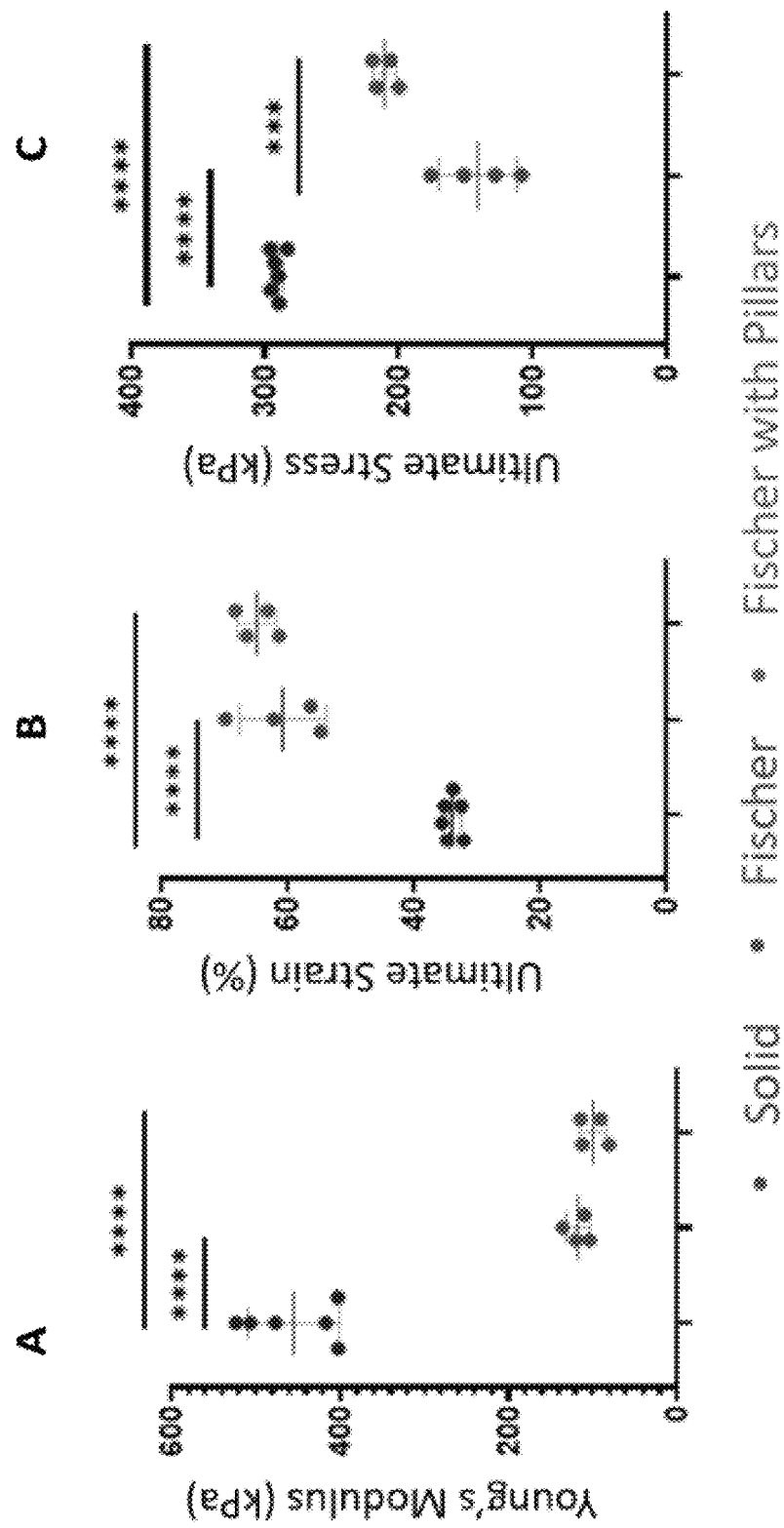
FIGS. 46A-46C show vertical pillars decreased Young's modulus (FIG. 46A) but increase Ultimate stress (FIG. 46C) on Ink A Fischer discs. Ultimate strain is shown in FIG. 46B. The properties were tested according to the Mechanical assessment procedure described in Example 2.
Figures 47A, 47B, 47C:
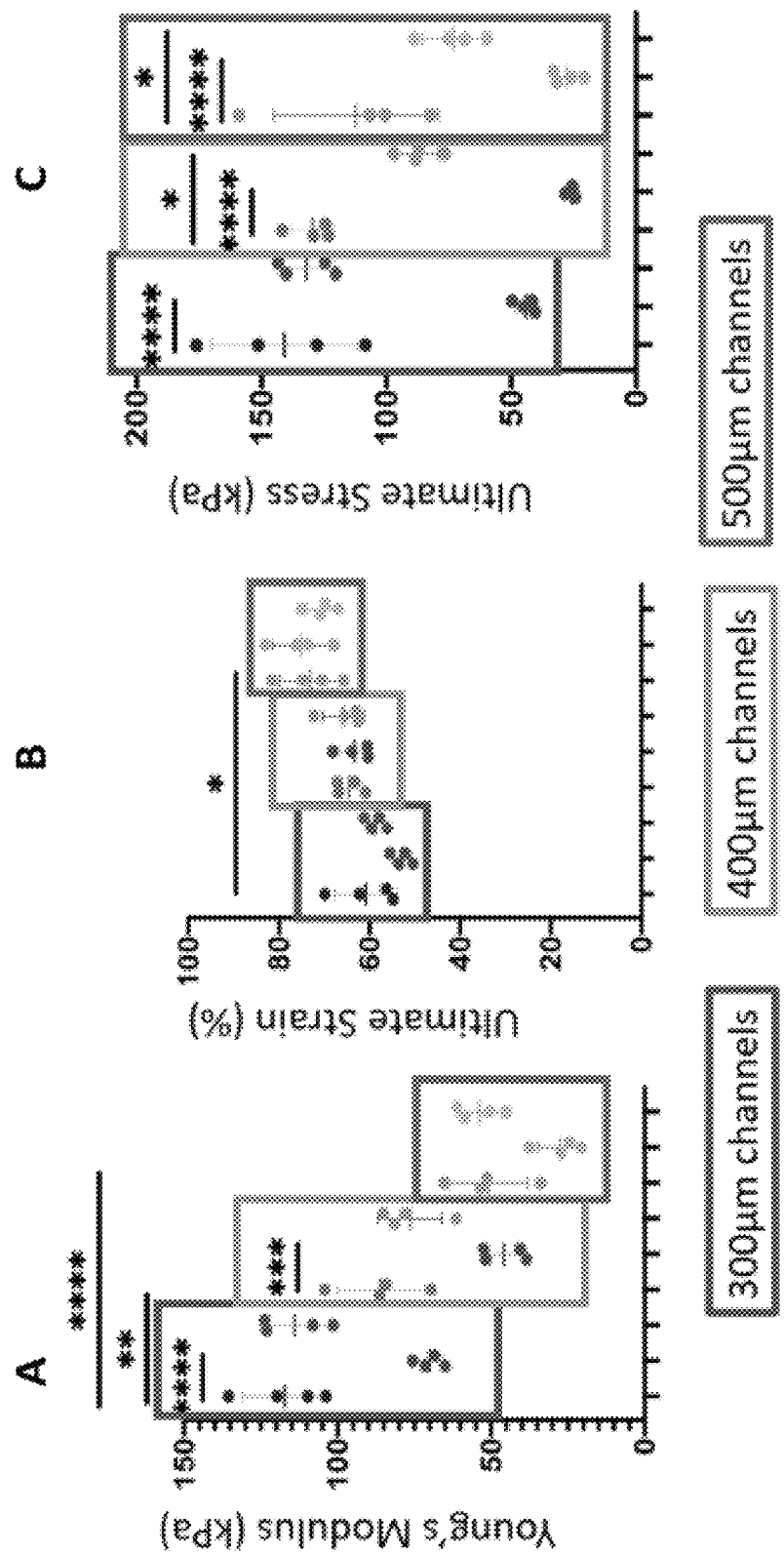
FIGS. 47A-47C show the effects of hydrolytic enzyme treatment of fisher discs with containing channel sizes on compressive Young's modulus in FIG. 47A, compressive ultimate strain in FIG. 47B, and compressive ultimate stress in FIG. 47C, of varying channel thickness of material to by hydrolyzed. The properties were tested according to the Mechanical assessment procedure described in Example 2.

Example 5: 3D Printed Objects with Pillars 3D printed objects with pillars were tested accordingly to the procedure of Example 2. Young's modulus, ultimate stress, and ultimate strain where the assessed. FIG. 46 shows vertical pillars decreased Young's modulus (FIG. 46A) but increase Ultimate stress (FIG. 46C) on Ink A Fischer discs. Ultimate strain is shown in FIG. 46B.

The present application incorporates by reference in their entirety each of the following documents: (a) U.S. provisional application No. 63/185,293 filed May 6, 2021 titled "USE OF FUNCTIONALIZED AND NON-FUNCTIONALIZED ECMS, ECM FRAGMENTS, PEPTIDES AND BIOACTIVE COMPONENTS TO CREATE CELL ADHESIVE 3D PRINTED OBJECTS" and U.S. non-provisional and/or PCT application(s) under the same title filed on May 6, 2022; (b) U.S. provisional application No. 63/185,300 filed May 6, 2021 titled "CONTROLLING THE SIZE OF 3D PRINTING HYDROGEL OBJECTS USING HYDROPHILIC MONOMERS, HYDROPHOBIC MONOMERS, AND CROSSLINKERS" and U.S. non-provisional and/or PCT application(s) under the same title filed on May 6, 2022; (c) U.S. provisional application No. 63/185,305 filed May 6, 2021 titled "PHOTOCURABLE REINFORCEMENT OF 3D PRINTED HYDROGEL OBJECTS" and U.S. non-provisional and/or PCT application(s) under the same title filed on May 6, 2022; (d) U.S. provisional application No. 63/185,299 filed May 6, 2021 titled "ADDITIVE MANUFACTURING OF HYDROGEL TUBES FOR BIOMEDICAL APPLICATIONS" and U.S. non-provisional and/or PCT application(s) under the same title filed on May 6, 2022; (e) U.S. provisional application No. 63/185,298 filed May 6, 2021 titled "MICROPHYSIOLOGICAL 3-D PRINTING AND ITS APPLICATIONS" and U.S. non-provisional and/or PCT application(s) under the same title filed on May 6, 2022.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety. Further embodiments are set forth in the following claims.

What is claimed is:

1. A method of modifying a polymeric scaffold comprising polymerized poly(ethylene glycol) di(meth)acrylate moieties, polymerized poly(ethylene glycol) di(meth)acrylamide moieties, polymerized poly(ethylene glycol) (meth)acrylate/(methacrylamide) moieties, or mixtures thereof, the method comprising:
provyding the polymeric scaffold;
contacting the polymeric scaffold with a hydrolysis agent comprising NaOH and a proteolysis agent comprising cholesterol esterase; and
after contacting the polymeric scaffold with the hydrolysis agent and the proteolysis agent, contacting the polymeric scaffold with lung cells,
wherein contacting the polymeric scaffold with the hydrolysis agent and the proteolysis agent increases lung cell attachment to the polymeric scaffold and reduces a Young's modulus of the polymeric scaffold.

2. The method of claim 1, wherein the polymeric scaffold comprises polymerized poly(ethyelene glycol) diacrylate moieties.

3. The method of claim 2, wherein the polymerized poly(ethylene glycol) diacrylate moieties comprise PEGDA3400, PEGDA575, or a mixture thereof.

4. The method of claim 1, wherein the polymeric scaffold further comprises polymerized collagen.

5. The method of claim 1, wherein the polymeric scaffold further comprises polymerized hydroxypropyl acrylate (HPA).

6. The method of claim 1, wherein the polymeric scaffold further comprises a polymerized UV initiator.

7. The method of claim 1, wherein the concentration of the hydrolysis agent is about 1 mM to about 25 mM, about 25 mM to about 50 mM, about 50 mM to about 100 mM, about 100 mM to about 150 mM, about 150 mM to about 300 mM, about 300 mM to about 500 mM, about 500 mM to about 1 M, about 1 M to about 5 M, or about greater than 5 M.

8. The method of claim 1, wherein the scaffold is contacted with the hydrolysis agent for about 1 min to about 30 min, about 30 min to about 1 hr, about 1 hr to about 2.5 hr, about 2.5 hr to about 5 hr, about 5 hr to about 7.5 hr, about 7.5 hr to about 10 hr, about 10 hr to about 24 hr, about 24 hr to about 2 days, about 2 days to about 4 days, about 4 days to about 8 days, about 8 days to about 12 days, about 12 days to about 30 days, or greater than about 30 days.

9. The method of claim 1, wherein the concentration of the proteolysis agent is about 0.1 U/mL to about 1 U/mL, about 1 U/mL to about 2.5 U/mL, about 2.5 U/mL to about 5 U/mL, about 5 U/mL to about 7.5 U/mL, about 7.5 U/mL to about 10 U/mL, about 10 U/mL to about 15 U/mL, or about greater than 15 U/mL.

10. The method of claim 1, wherein the scaffold is contacted with the proteolysis agent for about 1 hr, about 1 hr to about 2.5 hr, about 2.5 hr to about 5 hr, about 5 hr to about 7.5 hr, about 7.5 hr to about 10 hr, about 10 hr to about 24 hr, about 24 hr to about 2 days, about 2 days to about 4 days, about 4 days to about 8 days, about 8 days to about 12 days, about 12 days to about 30 days, or greater than about 30 days.

11. The method of claim 1, wherein the scaffold is a 3D-printed scaffold.

12. The method of claim 1, wherein the scaffold comprises channels and walls.

13. The method of claim 12, wherein the channels have a width of about 200 μm to about 500 μm.

14. The method of claim 12, wherein the walls have a width of about 150 μm to about 400 μm.

15. A polymeric scaffold produced by the method of claim 1.

16. A method of increasing the affinity of a polymeric scaffold for cells, the polymeric scaffold comprising polymerized poly(ethylene glycol) di(meth)acrylate moieties, polymerized poly(ethylene glycol) di(meth)acrylamide moieties, polymerized poly(ethyelene glycol) (meth)acrylate/(methacrylamide) moieties, or mixtures thereof,
wherein the method comprises providing the polymeric scaffold and contacting the polymeric scaffold with a hydrolysis agent comprising NaOH and a proteolysis agent comprising cholesterol esterase; and
after contacting the polymeric scaffold with the hydrolysis agent and the proteolysis agent, contacting the polymeric scaffold with lung cells,
wherein contacting the polymeric scaffold with the hydrolysis agent and the proteolysis agent increases lung cell attachment to the polymeric scaffold and reduces a Young's modulus of the polymeric scaffold.

* * * * *